(12) United States Patent
Shirk et al.

(10) Patent No.: US 6,218,185 B1
(45) Date of Patent: Apr. 17, 2001

(54) PIGGYBAC TRANSPOSON-BASED GENETIC TRANSFORMATION SYSTEM FOR INSECTS

(75) Inventors: Paul D Shirk, Gainesville, FL (US); Malcolm J. Fraser, Jr., Granger; Teresa A. Elick, Warsaw, both of IN (US); Omaththage P. Perera, Gainesville, FL (US)

(73) Assignees: The United States of America as represented by the Secretary of Agriculture, Washington, DC (US); University of Notre Dame, Notre Dame, IN (US); University of Florida, Gainesville, FL (US)

( * ) Notice: Subject to any disclaimer, the term of this patent is extended or adjusted under 35 U.S.C. 154(b) by 0 days.

(21) Appl. No.: 08/844,274

(22) Filed: Apr. 18, 1997

Related U.S. Application Data

(60) Provisional application No. 60/016,234, filed on Apr. 19, 1996.

(51) Int. Cl.⁷ .............................. C12N 5/10; C12N 15/09; C12N 15/85
(52) U.S. Cl. ................. 435/455; 435/320.1; 435/462; 435/465; 435/466; 535/23.1
(58) Field of Search .............................. 800/2; 435/320.1, 435/348, 455, 462, 465, 466; 536/23.1

(56) References Cited

PUBLICATIONS

O'Brochta et al., "Transposable elements and gene transformation in non–drosophilid insects", Insect Biochem. Molec. Biol. 26(8–9): 739–753, 1996.*

Cary, L. C., "Analyses of Trichplusia ni transposon IFP2 insertions within the FP–locus of nuclear polyhedrosis viruses", Ph.D. dissertation, Univ. of Notre Dame (172 pages), 1989.*

Fraser et al., "Assay for movement of Lepidopteran transposon IFP2 in insect cells using a baculovirus genome as the target", Virol. 211 (2): 397–407, Aug. 1995.*

Lidholm et al., "The transposable element mariner mediates germline transformation in Drosophila melanogaster", Genetics 134: 859–868, 1993.*

Ashburner M. (Drosophila, a Laboratory Handbook, CSH, 1989, pp. 1024, 1035, 1051).*

Crampton J. M. (Symp. R. Entomol. Soc. London, 1992, vol. Date 1991, 16th, 3–20).*

Unsal et al. (Journal of Molecular Biology, (1995) 248, 812–823).*

Cary, L. (Dissertation Abstracts International, (1989) vol. 50, No. 12B, p. 5451), Abstract only.*

Wang, et al. (Insect Molecular Biology, (1993) vol. 1, No. 3, pp. 109–116).*

Karess et al. (Cell, vol. 38, 135–146, Aug. 1984).*

\* cited by examiner

*Primary Examiner*—Scott D. Priebe
(74) *Attorney, Agent, or Firm*—M. Howard Silverstein; John D. Fado; Gail E. Poulos

(57) ABSTRACT

The present invention is directed to nucleic acid and amino acid sequences for transformation constructs containing piggyBac or tagalong transposable elements. These constructs allow for the precise excision and insertion of heterologous DNA into a host cell.

28 Claims, 62 Drawing Sheets

```
                10         20         30         40         50
        CCCTAGAAAG ATAGTCTGCG TAAAATTGAC GCATGCATTC TTGAAATATT
                60         70         80         90        100
        GCTCTCTCTT TCTAAATAGC GCGAATCCGT CGCTGTTTGC AATTTAGGAC
               110        120        130        140        150
        ATCTCAGTCG CCGCTTGGAG CTCGGCTGAG GCGTGCTTGT CAATGCGGTA
               160        170        180        190
        AGTGTCACTG ATTTTGAACT ATAACGACCG CGTGAGTCAA AATGACGCAT
               200        210        220        230        240
        GATTATCTTT TACGTGACTT TTAAGATTTA ACTCATACGA TAATTAATAT 250        260        270        280        290
        TGTTATTTCA TGTTCTACTT ACGTGATAAC TTATTATATA TATATTTTCT
               300        310        320         330        340
        TGTTATAGAT ATCGTGACTA ATATATAATA AA ATG GGA TGT TCT TTA GAC
                                           Met Gly Cys Ser Leu Asp

GAT GAG CAT ATC CTC TCT GCT CTT CTG CAA GGC GAT GAC GAG CTT
        Asp Glu His Ile Leu Ser Ala Leu Leu Gln Gly Asp Asp Glu Leu

GTT GGT GAG GAT TCT GAC AGT GAA ATA TCA GAT CAC GTA AGT GAA
        Val Gly Glu Asp Ser Asp Ser Glu Ile Ser Asp His Val Ser Glu

GAC GTC CAG AGC GAT ACA GAA GAA GCG TTT ATA GAT GAG GTA CAT
        Asp Val Gln Ser Asp Thr Glu Glu Ala Phe Ile Asp Glu Val His

GAA GTG TCA GCC AAC GTC AAG CGT AGT GAA ATA TTA GAC GAA CAA
        Glu Val Ser Ala Asn Val Lys Arg Ser Glu Ile Leu Asp Glu Gln

AAT GTT ATT GAA CAA CCA GGT TCT TCA TTG GCT TCT AAC AGA ATC
```

FIG. 5a

```
                Asn Val Ile Glu Gln Pro Gly Ser Ser Leu Ala Ser Asn Arg Ile

TTG ACC TTG CCA CAG AGG ACT ATT ACA GGT AAG AAT AAA CAT TGT
                Leu Thr Leu Pro Gln Arg Thr Ile Arg Gly Lys Asn Lys His Cys
   5
                TGG TCA ACT TCA AAG TCC ACG AGC GGT AGC CGA GTC TCT GCA CTG
                Trp Ser Thr Ser Lys Ser Thr Ser Gly Ser Arg Val Ser Ala Leu

AAC ATT GTC AGA TCT CAA AGA GGT CCG ACG CGT ATG TGC CGC AAT
  10            Asn Ile Val Arg Ser Gln Arg Gly Pro Thr Arg Met Cys Arg Asn

ATA TAT GAC CCA CTT TTA TGC TTC AAA CTA TTT TTT ACT GAT GAG
                Ile Tyr Asp Pro Leu Leu Cys Phe Lys Leu Phe Phe Thr Asp Glu

15            ATA ATT TCG CAA ATT GTA AAA TGG ACA AAT GCT GAG ATA TCA TTG
                Ile Ile Ser Gln Ile Val Lys Trp Thr Asn Ala Glu Ile Ser Leu
                AAA CGT CGG GAA TCT ATG ACA GGT GCT ACA TTT CGT GAC ACG AAT
                Lys Arg Arg Glu Ser Met Thr Gly Ala Thr Phe Arg Asp Thr Asn

20            GAA GAT GAA ATC TAT GCT TTC TTT GGT ATT CTG GTA ATG ACA GCA
                Glu Asp Glu Ile Tyr Ala Phe Phe Gly Ile Leu Val Met Thr Ala

GTG AGA AAA GAT AAC CAC ATG TCC ACA GAT GAC CTC TTT GGA TCG
                Val Arg Lys Asp Asn His Met Ser Tyr Val Ser Val Met Ser Leu
  25
                ATC TTT GTC AAT GTG TAC GTC TCT GTA ATG AGT CTG TGG ATC GTT
                Thr Asp Asp Leu Phe Gly Ser Ile Phe Val Asn Val Trp Ile Val

TTG GAT TTT TTG ATA CGA TGT CTT AGA ATG GAT GAC AAA AGT ATA
  30            Leu Asp Phe Leu Ile Arg Cys Leu Arg Met Asp Asp Lys Ser Ile

CGG CCC ACA CTT CGA GAA AAC GAT GTA TTT ACT CCT GTT AGA AAA
                Arg Pro Thr Leu Arg Glu Asn Asp Val Phe Thr Pro Val Arg Lys

35            ATA TGG GAT CTC TTT ATC CAT CAG TGC ATA CAA AAT TAC ACT CCA
```

FIG. 5b

```
      Ile Trp Asp Leu Phe Ile His Gln Cys Ile Gln Asn Tyr Thr Pro

GGG GCT CAT TTG ACC ATA GAT GAA CAG TTA CTT GGT TTT AGA GGA
      Gly Ala His Leu Thr Ile Asp Glu Gln Leu Leu Gly Phe Arg Gly
 5
      CGG TGT CCG TTT AGG ATG TAT ATC CCA AAC AAG CCA AGT AAG TAT
      Arg Cys Pro Phe Arg Met Tyr Ile Pro Asn Lys Pro Ser Lys Tyr

GGA ATA AAA ATC CTC ATG ATG TGT GAC AGT GGT ACG AAG TAT ATG
 10   Gly Ile Lys Ile Leu Met Met Cys Asp Ser Gly Thr Lys Tyr Met

ATA AAT GGA ATG CCT TAT TTG GGA AGA GGA ACA CAG ACC AAC GGA

Ile Asn Gly Met Pro Tyr Leu Gly Arg Gly Thr Gln Thr Asn Gly
 15

GTA CCA CTC GGT GAA TAC TAC GTG AAG GAG TTA TCA AAG CCT GTG
      Val Pro Leu Gly Glu Tyr Tyr Val Lys Glu Leu Ser Lys Pro Val

20
      CAC GGT AGT TGT CGT AAT ATT ACG TGT GAC AAT TGG TTC ACC TCA
      His Gly Ser Cys Arg Asn Ile Thr Cys Asp Asn Trp Phe Thr Ser

ATC CCT TTG GCA AAA AAC TTA CTA CAA GAA CCG TAT AAG TTA ACC
 25   Ile Pro Leu Ala Lys Asn Leu Leu Gln Glu Pro Tyr Lys Leu Thr

ATT GTG GGA ACC GTG CGA TCA AAC AAA CGC GAG ATA CCG GAA GTA
      Ile Val Gly Thr Val Arg Ser Asn Lys Arg Glu Ile Pro Glu Val

30   CTG AAA AAC AGT CGC TCC AGG CCA GTG GGA ACA TCG ATG TTT TGT
      Leu Lys Asn Ser Arg Ser Arg Pro Val Gly Thr Ser Met Phe Cys

TTT GAC GGA CCC CTT ACT CTC GTC TCA TAT AAA CCG AAG CCA GCT
      Phe Asp Gly Pro Leu Thr Leu Val Ser Tyr Lys Pro Lys Pro Ala
 35
```

FIG. 5c

```
    AAG ATG GTA TAC TTA TTA TCA TCT TGT GAT GAG GAT GCT TCT ATC
    Lys Met Val Tyr Leu Leu Ser Ser Cys Asp Glu Asp Ala Ser Ile

AAC GAA AGT ACC GGT AAA CCG CAA ATG GTT ATG TAT TAT AAT CAA
 5  Asn Glu Ser Thr Gly Lys Pro Gln Met Val Met Tyr Tyr Asn Gln

ACT AAA GGC GGA GTG GAC ACG CTA GAC CAA ATG TGT TCT GTG ATG
    Thr Lys Gly Gly Val Asp Thr Leu Asp Gln Met Cys Ser Val Met

10  ACC TGC AGT AGG AAG ACG AAT AGG TGG CCT ATG GCA TTA TTG TAC
    Thr Cys Ser Arg Lys Thr Asn Arg Trp Pro Met Ala Leu Leu Tyr

GGA ATG ATA AAC ATT GCC TGC ATA AAT TCT TTT ATT ATA TAC AGC
    Gly Met Ile Asn Ile Ala Cys Ile Asn Ser Phe Ile Ile Tyr Ser
15
    CAT AAT GTC AGT AGC AAG GGA GAA AAG GTT CAA AGT CGC AAA AAA
    His Asn Val Ser Ser Lys Gly Glu Lys Val Gln Ser Arg Lys Lys

20  TTT ATG AGA AAC CTT TAC ATG AGC CTG ACG TCA TCG TTT ATG CGT
    Phe Met Arg Asn Leu Tyr Met Ser Leu Thr Ser Ser Phe Met Arg

AAC CGT TTA GAA GCT CCT ACT TTG AAG AGA TAT TTG CGC GAT AAT
    Asn Arg Leu Glu Ala Pro Thr Leu Lys Arg Tyr Leu Arg Asp Asn
25
    ATC TCT AAT ATT TTG CCA AAT GAA GTG CCT GGT ACA TCA GAT GAC
    Ile Ser Asn Ile Leu Pro Asn Glu Val Pro Gly Thr Ser Asp Asp

AGT ACT GAA GAG CCA GTA ATG AAA AAA CGT ACT TAC TGT ACT TAC
30  Ser Thr Glu Glu Pro Val Met Lys Lys Arg Thr Tyr Cys Thr Tyr

TGC CCC TCT AAA ATA AGG CGA AAG GCA AAT GCA TCG TGC AAA AAA
    Pro Ser Lys Ile Arg Arg Cys Lys Ala Asn Ala Ser Cys Lys Lys

35  TGC AAA AAA GTT ATT TGT CGA GAG CAT AAT ATT GAT ATG TGC CAA
```

FIG. 5d

```
Cys Lys Lys Val Ile Cys Arg Glu His Asn Ile Asp Met Cys Gln

AGT TGT TTC TGG ACT GAC TAATAAG TATAATTTGT TTCTATTATG
Ser Cys Phe Trp Thr Asp
TATAAGTTAA GCTAATTACT TATTTTATAA TACAACATGA CTGTTTTTAA
AGTACAAAAT AAGTTTATTT TTGTAAAAGA GAGAATGTTT AAAAGTTTTG
TTACTTTAGA AGAAATTTTG AGTTTTGTT TTTTTTAAT AAATAAATAA
ACATAAATAA ATTGTTTGTT GAATTTATTA TTAGTATGTA AGTGTAAATA
TAATAAAACT TAATATCTAT TCAAATTAAT AAATAAACCT CGATATACAG
ACCGATAAAA ACACATGCGT CAATTTTACG CATGATTATC TTTAACGTAC
GTCACAATAT GATTATCTTT CTAGGG
```

FIG. 5e

```
  1 TCGCGCGTTT CGGTGATGAC GGTGAAAACC TCTGACACAT
    GCAGCTCCCG GAGACGGTCA
 61 CAGCTTGTCT GTAAGCGGAT GCCGGGAGCA GACAAGCCCG
    TCAGGGCGCG TCAGCGGGTG
121 TTGGCGGGTG TCGGGGCTGG CTTAACTATG CGGCATCAGA
    GCAGATTGTA CTGAGAGTGC
181 ACCATATGCG GTGTGAAATA CCGCACAGAT GCGTAAGGAG
    AAAATACCGC ATCAGGCGCC
241 ATTCGCCATT CAGGCTGCGC AACTGTTGGG AAGGGCGATC
    GGTGCGGGCC TCTTCGCTAT
301 TACGCCAGCT GGCGAAAGGG GGATGTGCTG CAAGGCGATT
    AAGTTGGGTA ACGCCAGGGT
361 TTTCCCAGTC ACGACGTTGT AAAACGACGG CCAGTGCCAA
    GCTTTGTTTA AAATATAACA
421 AAATTGTGAT CCCACAAAAT GAAGTGGGGC AAAATCAAAT
    AATTAACTAG TGTCCGTAAA
481 CTTGTTGGTC TTCAACTTTT TGAGGAACAC GTTGGACGGC
    AAATCGTGAC TATAACACAA
541 GTTGATTTAA TAATTTTAGC CAACACGTCG GGCTGCGTGT
    TTTTTGCGCT CTGTGTACAC
601 GTTGATTAAC TGGTCGATTA AATAATTTAA TTTTTGGTTC
    TTCTTTAAAT CTGTGATGAA
661 ATTTTTTAAA ATAACTTTAA ATTCTTCATT GGTAAAAAAT
    GCCACGTTTT GCAACTTGTG
721 AGGGTCTAAT ATGAGGTCAA ACTCAGTAGG AG
    TTTTATCC AAAAAAGAAA ACATGATTAC
781 GTCTGTACAC GAACGCGTAT TAACGCAGAG TGCAAAGTAT
    AAGAGGGTTA AAAAATATAT
841 TTTACGCACC ATATACGCAT CGGGTTGATA TCGTTAATAT
    GGATCAATTT GAACAGTTGA
901 TTAACGTGTC TCTGCTCAAG TCTTTGATCA AAACGCAAAT
    CGACGAAAAT GTGTCGGACA
961 ATATCAAGTC GATGAGCGAA AAACTAAAAA GGCTAGAATA
    CGACAATCTC ACAGACAGCG
1021 TTGAGATATA CGGTATTCAC GACAGCAGGC TGAATAATAA
```

FIG. 6a

```
                AAAAATTAGA AACTATTATT
        1081 TAACCCTAGA AAGATAATCA TATTGTGACG TACGTTAAAG
        ATAATCATGC GTAAAATTGA
        1141 CGCATGTGTT TTTATCGGTC TGTATATCGA GGTTTATTTA
        TTAATTTGAA TAGATATTAA
        1201 GTTTTATTAT ATTTACACTT ACATACTAAT AATAAATTCA
        ACAAACAATT TATTTATGTT
        1261 TATTTATTTA TTAAAAAAAA ACAAAAACTC AAAATTTCTT
        CTAAAGTAAC AAAACTTTTA
        1321 AACATTCTCT CTTTTACAAA AATAAACTTA TTTTGTACTT
        TAAAAACAGT CATGTTGTAT
        1381 TATAAAATAA GTAATTAGCT TAACTTATAC ATAATAGAAA
        CAAATTATAC TTATTAGTCA
        1441 GTCCAGAAAC AACTTTGGCA CATATCAATA TTATGCTCTC
        GACAAATAAC TTTTTTGCAT
        1501 TTTTTGCACG ATGCATTTGC CTTTCGCCTT ATTTTAGAGG G
        GCAGTAAGT ACAGTAAGTA
        1561 CGTTTTTTCA TTACTGGCTC TTCAGTACTG TCATCTGATG
        TACCAGGCAC TTCATTTGGC
        1621 AAAATATTAG AGATATTATC GCGCAAATAT CTCTTCAAAG
        TAGGAGCTTC TAAACGGTTA
        1681 CGCATAAACG ATGACGTCAG GCTCATGTAA AGGTTTCTCA
        TAAATTTTTT GCGACTTTGA
        1741 ACCTTTTCTC CCTTGCTACT GACATTATGG CTGTATATAA
        TAAAAGAATT TATGCAGGCA
        1801 ATGTTTATCA TTCCGTACAA TAATGCCATA GGCCACCTAT
        TCGTCTTCCT ACTGCAGGTC
        1861 ATCACAGAAC ACATTTGGTC TAGCGTGTCC ACTCCGCCTT
        TAGTTTGATT ATAATACATA
        1921 ACCATTTGCG GTTACCGGT ACTTTCGTTG ATAGAAGCAT
        CCTCATCACA AGATGATAAT
        1981 AAGTATACCA TCTTAGCTGG CTTCGGTTTA TATGAGACGA
        GAGTAAGGGG TCCGTCAAAA
        2041 CAAAACATCG TGCACAGGGC CCCCCCTCGA GAAATTTCTC
        TGGCCGTTAT TCGTTATTCT
        2101 CTCTTTTCTT TTTGGGTCTC TCCCTCTCTG CACTAATGCT
        CTCTCACTCT GTCACACAGT
        2161 AAACGGCATA CTGCTCTCGT TGGTTCGAGA GAGCGCGCCT
```

FIG. 6b

CGAATGTTCG CGAAAAGAGC
2221 GCCGGAGTAT AAATAGAGGC GCTTCGTCTA CGGAGCGACA ATTCAATTCA AACAAGCAAA
2281 GTGAACACGT CGCTAAGCGA AAGCTAAGCA AATAAACAAG CGCAGCTGAA CAAGCTAAAC
2341 AATCTGCAGT AAAGTGCAAG TTAAAGTGAA TCAATTAAAA GTAACCAGCA ACCAAGTAAA
2401 TCAACTGCAA CTACTGAAAT CTGCCAAGAA GTAATTATTG AATACAAGAA GAGAACTCTG
2461 AATAGGGAAT TGGGAATTAG GTACCGAATT ACACAGAATG AATTCCGGCG ATCGGATCAA
2521 TACCGTGCGC GGTCCTATCA CAATCTCTGA AGCGGGTTTC ACACTGACTC ACGAGCACAT
2581 CTGCGGCAGC TCGGCAGGAT TCTTGCGTGC TTGGCCAGAG TTCTTCGGTA GCCGCAAAGC
2641 TCTAGCGGAA AAGGCTGTGA GAGGATTGCG CCGCGCCAGA GCGGCTGGCG TGCGAACGAT
2701 TGTCGATGTG TCGACTTTCG ATATCGGTCG CGACGTCAGT TTATTGGCCG AGGTTTCGCG
2761 GGCTGCCGAC GTTCATATCG TGGCGGCGAC CGGCTTGTGG TTCGACCCGC CACTTTCGAT
2821 GCGATTGAGG AGTGTAGAGG AACTCACACA GTTCTTCCTG CGTGAGATTC AATATGGCAT
2881 CGAAGACACC GGAATTAGGG CGGGCATTAT CAAGGTCGCG ACCACAGGCA AGGCGACCCC
2941 CTTTCAGGAG TTAGTGTTAA AGGCGGCCGC CCGGGCCAGC TTGGCCACCG GTGTTCCGGT
3001 AACCACTCAC ACGGCAGCAA GTCAGCGCGA TGGTGAGCAG CAGGCCGCCA TTTTTGAGTC
3061 CGAAGGCTTG AGCCCCTCAC GGGTTTGTAT TGGTCACAGC GATGATACTG ACGATTTGAG
3121 CTATCTCACC GCCCTCGCTG CGCGCGGATA CCTCATCGGT CTAGACCACA TCCCGCACAG
3181 TGCGATTGGT CTAGAAGATA ATGCGAGTGC ATCAGCCCTC CTGGGCATCC GTTCGTGGCA
3241 AACACGGGCT CTCTTGATCA AGGCGCTCAT CGACCAAGGC TACATGAAAC AAATCCTCGT
3301 TTCGAATGAC TGGCTGTTCG GGTTTTCGAG CTATGTCACC

FIG. 6c

```
           AACATCATGG
           ACGTGATGGA
      3361 TCGCGTGAAC CCCGACGGGA TGGCCTTCAT TCCACTGAGA
           GTGATCCCAT
           TCCTACGAGA
      3421 GAAGGGCGTC CCACAGGAAA CGCTGGCAGG CATCACTGTG
           ACTAACCCGG CGCGGTTCTT
      3481 GTCACCGACC TTGCGGGCGT CATGACGCCA TCTGGATCTA
           GAATGGTTTA TTTGTACACA
      3541 TTTACTTTAA ATTTAATAAA ATTTACTTTA GCCGTTGTCC
           GATAATTCTT ATATTTAATT
      3601 TAAACCACCT GCAAGCTTTT AATAAATCTA TATGTTCCCG
           GGATCTGACA ATGTTCAGTG
      3661 CAGAGACTCG GCTACCGCTC GTGGACTTTG AAGTTGACCA
           ACAATGTTTA
           TTCTTACCTC
      3721 TAATAGTCCT CTGTGGCAAG GTCAAGATTC TGTTAGAAGC
           CAATGAAGAA
           CCTGGTTGTT
      3781 CAATAACATT TTGTTCGTCT AATATTTCAC TACGCTTGAC
           GTTGGCTGAC ACTTCATGTA
      3841 CCTCATCTAT AAACGCTTCT TCTGTATCGC TCTGGACGTC
           TTCACTTACG TGATCTGATA
      3901 TTTCACTGTC AGAATCCTCA CCAACAAGCT CGTCATCGCC
           TTGCAGAAGA GCAGAGAGGA
      3961 TATGCTCATC GTCTAAAGAA CATCCCATTT TATTATATAT
           TAGTCACGAT ATCTATAACA
      4021 AGAAAATATA TATATAATAA GTTATCACGT AAGTAGAACA
           TGAAATAACA ATATTAATTA
      4081 TCGTATGAGT TAAATCTTAA AAGTCACGTA AAAGATAATC
           ATGCGTCATT TTGACTCACG
      4141 CGGTCGTTAT AGTTCAAAAT CAGTGACACT TACCGCATTG
           ACAAGCACGC CTCAGCCGAG
      4201 CTCCAAGCGG CGACTGAGAT GTCCTAAATT GCAAACAGCG
           ACGGATTCGC GCTATTTAGA
      4261 AAGAGAGAGC AATATTTCAA GAATGCATGC GTCAATTTTA
           CGCAGACTAT CTTTCTAGGG
      4321 TTAAAAAAGA TTTGCGCTTT ACTCGACCTA AACTTTAAAC
```

FIG. 6d

```
     ACGTCATAGA ATCTTCGTTT
4381 GACAAAAACC ACATTGTGGC CAAGCTGTGT GACGCGACGC
     GCGCTAAAGA ATGGCAAACC
4441 AAGTCGCGCG AGCGTCGACT CTAGAGGATC CCCGGGTACC
     GAGCTCGAAT TCGTAATCAT
4501 GGTCATAGCT GTTTCCTGTG TGAAATTGTT ATCCGCTCAC
     AATTCCACAC AACATACGAG
4561 CCGGAAGCAT AAAGTGTAAA GCCTGGGGTG CCTAATGAGT
     GAGCTAACTC ACATTAATTG
4621 CGTTGCGCTC ACTGCCCGCT TTCCAGTCGG GAAACCTGTC
     GTGCCAGCTG CATTAATGAA
4681 TCGGCCAACG CGCGGGGAGA GGCGGTTTGC GTATTGGGCG
     CTCTTCCGCT TCCTCGCTCA
4741 CTGACTCGCT GCGCTCGGTC GTTCGGCTGC GGCGAGCGGT
     ATCAGCTCAC TCAAAGGCGG
4801 TAATACGGTT ATCCACAGAA TCAGGGGATA ACGCAGGAAA
     GAACATGTGA GCAAAAGGCC
4861 AGCAAAAGGC CAGGAACCGT AAAAAGGCCG CGTTGCTGGC
     GTTTTTCCAT AGGCTCCGCC
4921 CCCCTGACGA GCATCACAAA AATCGACGCT CAAGTCAGAG
     GTGGCGAAAC CCGACAGGAC
4981 TATAAAGATA CCAGGCGTTT CCCCCTGGAA GCTCCCTCGT
     GCGCTCTCCT GTTCCGACCC
5041 TGCCGCTTAC CGGATACCTG TCCGCCTTTC TCCCTTCGGG
     AAGCGTGGCG CTTTCTCAAT
5101 GCTCACGCTG TAGGTATCTC AGTTCGGTGT AGGTCGTTCG
     CTCCAAGCTG GGCTGTGTGC
5161 ACGAACCCCC CGTTCAGCCC GACCGCTGCG CCTTATCCGG
     TAACTATCGT CTTGAGTCCA
5221 ACCCGGTAAG ACACGACTTA TCGCCACTGG CAGCAGCCAC
     TGGTAACAGG ATTAGCAGAG
5281 CGAGGTATGT AGGCGGTGCT ACAGAGTTCT TGAAGTGGTG
     GCCTAACTAC GGCTACACTA
5341 GAAGGACAGT ATTTGGTATC TGCGCTCTGC TGAAGCCAGT
     TACCTTCGGA AAAAGAGTTG
5401 GTAGCTCTTG ATCCGGCAAA CAAACCACCG CTGGTAGCGG
     TGGTTTTTTT GTTTGCAAGC
5461 AGCAGATTAC GCGCAGAAAA AAAGGATCTC AAGAAGATCC
```

FIG. 6e

```
          TTTGATCTTT TCTACGGGGT
     5521 CTGACGCTCA GTGGAACGAA AACTCACGTT AAGGGATTTT
          GGTCATGAGA TTATCAAAAA
     5581 GGATCTTCAC CTAGATCCTT TTAAATTAAA AATGAAGTTT
          TAAATCAATC TAAAGTATAT
     5641 ATGAGTAAAC TTGGTCTGAC AGTTACCAAT GCTTAATCAG
          TGAGGCACCT ATCTCAGCGA
     5701 TCTGTCTATT TCGTTCATCC ATAGTTGCCT GACTCCCCGT
          CGTGTAGATA ACTACGATAC
     5761 GGGAGGGCTT ACCATCTGGC CCCAGTGCTG CAATGATACC
          GCGAGACCCA CGCTCACCGG
     5821 CTCCAGATTT ATCAGCAATA AACCAGCCAG CCGGAAGGGC
          CGAGCGCAGAAGTGGTCCTG
     5881 CAACTTTATC CGCCTCCATC CAGTCTATTA ATTGTTGCCG
          GGAAGCTAGA GTAAGTAGTT
     5941 CGCCAGTTAA TAGTTTGCGC AACGTTGTTG CCATTGCTAC
          AGGCATCGTG GTGTCACGCT
     6001 CGTCGTTTGG TATGGCTTCA TTCAGCTCCG GTTCCCAACG
          ATCAAGGCGA GTTACATGAT
     6061 CCCCCATGTT GTGCAAAAAA GCGGTTAGCT CCTTCGGTCC
          TCCGATCGTT GTCAGAAGTA
     6121 AGTTGGCCGC AGTGTTATCA CTCATGGTTA TGGCAGCACT
          GCATAATTCT CTTACTGTCA
     6181 TGCCATCCGT AAGATGCTTT TCTGTGACTG GTGAGTACTC
          AACCAAGTCA TTCTGAGAAT
     6241 AGTGTATGCG GCGACCGAGT TGCTCTTGCC CGGCGTCAAT
          ACGGGATAAT ACCGCGCCAC
     6301 ATAGCAGAAC TTTAAAAGTG CTCATCATTG GAAAACGTTC
          TTCGGGGCGA AAACTCTCAA
     6361 GGATCTTACC GCTGTTGAGA TCCAGTTCGA TGTAACCCAC
          TCGTGCACCC AACTGATCTT
     6421 CAGCATCTTT TACTTTCACC AGCGTTTCTG GGTGAGCAAA
          AACAGGAAGG CAAAATGCCG
     6481 CAAAAAAGGG AATAAGGGCG ACACGGAAAT GTTGAATACT
          CATACTCTTC CTTTTTCAAT
     6541 ATTATTGAAG CATTTATCAG GGTTATTGTC TCATGAGCGG
          ATACATATTT GAATGTATTT
     6601 AGAAAAATAA ACAAATAGGG GTTCCGCGCA CATTTCCCCG
```

FIG. 6f

```
     AAAAGTGCCA
     CCTGACGTCT
        6661 AAGAAACCAT TATTATCATG ACATTAACCT ATAAAAATAG GCGTATCACGA
     GGCCCTTTC
        6721 GTC
```

FIG. 6g

```
   1 GACGAAAGGG CCTCGTGATA CGCCTATTTT TATAGGTTAA TGTCATGATA ATAATGGTTT
  61 CTTAGACGTC AGGTGGCACT TTTCGGGGAA ATGTGCGCGG AACCCCTATT TGTTTATTTT
 121 TCTAAATACA TTCAAATATG TATCCGCTCA TGAGACAATA ACCCTGATAA ATGCTTCAAT
 181 AATATTGAAA AAGGAAGAGT ATGAGTATTC AACATTTCCG TGTCGCCCTT ATTCCCTTTT
 241 TTGCGGCATT TTGCCTTCCT GTTTTTGCTC ACCCAGAAAC GCTGGTGAAA GTAAAAGATG
 301 CTGAAGATCA GTTGGGTGCA CGAGTGGGTT ACATCGAACT GGATCTCAAC AGCGGTAAGA
 361 TCCTTGAGAG TTTTCGCCCC GAAGAACGTT TTCCAATGAT GAGCACTTTT AAAGTTCTGC
 421 TATGTGGCGC GGTATTATCC CGTATTGACG CCGGGCAAGA GCAACTCGGT CGCCGCATAC
 481 ACTATTCTCA GAATGACTTG GTTGAGTACT CACCAGTCAC AGAAAAGCAT CTTACGGATG
 541 GCATGACAGT AAGAGAATTA TGCAGTGCTG CCATAACCAT GAGTGATAAC ACTGCGGCCA
 601 ACTTACTTCT GACAACGATC GGAGGACCGA AGGAGCTAAC CGCTTTTTTG CACAACATGG
 661 GGGATCATGT AACTCGCCTT GATCGTTGGG AACCGGAGCT GAATGAAGCC ATACCAAACG
 721 ACGAGCGTGA CACCACGATG CCTGTAGCAA TGGCAACAAC GTTGCGCAAA CTATTAACTG
 781 GCGAACTACT TACTCTAGCT TCCCGGCAAC AATTAATAGA CTGGATGGAG GCGGATAAAG
 841 TTGCAGGACC ACTTCTGCGC TCGGCCCTTC CGGCTGGCTG GTTTATTGCT GATAAATCTG
 901 GAGCCGGTGA GCGTGGGTCT CGCGGTATCA TTGCAGCACT GGGGCCAGAT GGTAAGCCCT
 961 CCCGTATCGT AGTTATCTAC ACGACGGGGA GTCAGGCAAC TATGGATGAA CGAAATAGAC
1021 AGATCGCTGA GATAGGTGCC TCACTGATTA AGCATTGGTA ACTGTCAGAC CAAGTTTACT
1081 CATATATACT TTAGATTGAT TTAAAACTTC ATTTTTAATT TAAAAGGATC TAGGTGAAGA
1141 TCCTTTTTGA TAATCTCATG ACCAAAATCC CTTAACGTGA GTTTTCGTTC CACTGAGCGT
1201 CAGACCCCGT AGAAAAGATC AAAGGATCTT CTTGAGATCC TTTTTTTCTG CGCGTAATCT
1261 GCTGCTTGCA AACAAAAAAA CCACCGCTAC CAGCGGTGGT TTGTTTGCCG GATCAAGAGC
1321 TACCAACTCT TTTTCCGAAG GTAACTGGCT TCAGCAGAGC GCAGATACCA
```

FIG. 7a

```
     AATACTGTCC
1381 TTCTAGTGTA GCCGTAGTTA GGCCACCACT TCAAGAACTC TGTAGCACCG
     CCTACATACC
1441 TCGCTCTGCT AATCCTGTTA CCAGTGGCTG CTGCCAGTGG CGATAAGTCG
     TGTCTTACCG
1501 GGTTGGACTC AAGACGATAG TTACCGGATA AGGCGCAGCG GTCGGGCTGA
     ACGGGGGGTT
1561 CGTGCACACA GCCCAGCTTG GAGCGAACGA CCTACACCGA ACTGAGATAC
     CTACAGCGTG
1621 AGCATTGAGA AAGCGCCACG CTTCCCGAAG GGAGAAAGGC
     GGACAGGTAT CCGGTAAGCG
1681 GCAGGGTCGG AACAGGAGAG CGCACGAGGG AGCTTCCAGG
     GGGAAACGCC TGGTATCTTT
1741 ATAGTCCTGT CGGGTTTCGC CACCTCTGAC TTGAGCGTCG ATTTTTGTGA
     TGCTCGTCAG
1801 GGGGGCGGAG CCTATGGAAA AACGCCAGCA ACGCGGCCTT TTTACGGTTC
     CTGGCCTTTT
1861 GCTGGCCTTT TGCTCACATG TTCTTTCCTG CGTTATCCCC TGATTCTGTG
     GATAACCGTA
1921 TTACCGCCTT TGAGTGAGCT GATACCGCTC GCCGCAGCCG AACGACCGAG
     CGCAGCGAGT
1981 CAGTGAGCGA GGAAGCGGAA GAGCGCCCAA TACGCAAACC GCCTCTCCCC
     GCGCGTTGGC
2041 CGATTCATTA ATGCAGCTGG CACGACAGGT TTCCCGACTG GAAAGCGGGC
     AGTGAGCGCA
2101 ACGCAATTAA TGTGAGTTAG CTCACTCATT AGGCACCCCA GGCTTTACAC
     TTTATGCTTC
2161 CGGCTCGTAT GTTGTGTGGA ATTGTGAGCG GATAACAATT TCACACAGGA
     AACAGCTATG
2221 ACCATGATTA CGAATTCGAG CTCGGTACCC GGGGATCCTC TAGAGTCGAC
     GCTCGCGCGA
2281 CTTGGTTTGC CATTCTTTAG CGCGCGTCGC GTCACACAGC TTGGCCACAA
     TGTGGTTTTT
2341 GTCAAACGAA GATTCTATGA CGTGTTTAAA GTTAGGTCG AGTAAAGCGC
     AAATCTTTTT
2401 TAACCCTAGA AAGATAGTCT GCGTAAAATT GACGCATGCA TTCTTGAAAT
     ATTGCTCTCT
2461 CTTTCTAAAT AGCGCGAATC CGTCGCTGTT TGCAATTTAG GACATCTCAG
     TCGCCGCTTG
2521 GAGCTCGGCT GAGGCGTGCT TGTCAATGCG GTAAGTGTCA CTGATTTTGA
     ACTATAACGA
2581 CCGCGTGAGT CAAAATGACG CATGATTATC TTTTACGTGA CTTTTAAGAT
     TTAACTCATA
2641 CGATAATTAA TATTGTTATT TCATGTTCTA CTTACGTGAT AACTTATTAT
     ATATATATTT
2701 TCTTGTTATA GATATCGTGA CTAATATATA ATAAAATGGG ATGTTCTTTA
     GACGATGAGC
2761 ATATCCTCTC TGCTCTTCTG CAAGGCGATG ACGAGCTTGT TGGTGAGGAT
```

FIG. 7b

TCTGACAGTG
2821 AAATATCAGA TCACGTAAGT GAAGACGTCC AGAGCGATAC AGAAGAAGCG
TTTATAGATG
2881 AGGTACATGA AGTGTCAGCC AACGTCAAGC GTAGTGAAAT ATTAGACGAA
CAAAATGTTA
2941 TTGAACAACC AGGTTCTTCA TTGGCTTCTA ACAGAATCTT GACCTTGCCA
CAGAGGACTA
3001 TTAGAGGTAA GAATAAACAT TGTTGGTCAA CTTCAAAGTC CACGAGCGGT
AGCCGAGTCT
3061 CTGCACTGAA CATTGTCAGA TCCCGGGAAC ATATAGATTT ATTAAAAGCT
TGCAGGTGGT
3121 TTAAATTAAA TATAAGAATT ATCGGACAAC GGCTAAAGTA AATTTTATTA
AATTTAAAGT
3181 AAATGTGTAC AAATAAACCA TTCTAGATCC AGATGGCGTC ATGACGCCCG
CAAGGTCGGT
3241 GACAAGAACC GCGCCGGGTT AGTCACAGTG ATGCCTGCCA GCGTTTCCTG
TGGGACGCCC
3301 TTCTCTCGTA GGAATGGGAT CACTCTCAGT GGAATGAAGG CCATCCCGTC
GGGGTTCACG
3361 CGATCCATCA CGTCCATGAT GTTGGTGACA TAGCTCGAAA ACCCGAACAG
CCAGTCATTC
3421 GAAACGAGGA TTTGTTTCAT GTAGCCTTGG TCGATGAGCG CCTTGATCAA
GAGAGCCCGT
3481 GTTTGCCACG AACGGATGCC CAGGAGGGCT GATGCACTCG CATTATCTTC
TAGACCAATC
3541 GCACTGTGCG GGATGTGGTC TAGACCGATG AGGTATCCGC GCGCAGCGAG
GGCGGTGAGA
3601 TAGCTCAAAT CGTCAGTATC ATCGCTGTGA CCAATACAAA CCCGTGAGGG
GCTCAAGCCT
3661 TCGGACTCAA AAATGGCGGC CTGCTGCTCA CCATCGCGCT GACTTGCTGC
CGTGTGAGTG
3721 GTTACCGGAA CACCGGTGGC CAAGCTGGCC CGGGCGGCCG CCTTTAACAC
TAACTCCTGA
3781 AAGGGGGTCG CCTTGCCTGT GGTCGCGACC TTGATAATGC CCGCCCTAAT
TCCGGTGTCT
3841 TCGATGCCAT ATTGAATCTC ACGCAGGAAG AACTGTGTGA GTTCCTCTAC
ACTCCTCAAT
3901 CGCATCGAAA GTGGCGGGTC GAACCACAAG CCGGTCGCCG CCACGATATG
AACGTCGGCA
3961 GCCCGCGAAA CCTCGGCCAA TAAACTGACG TCGCGACCGA TATCGAAAGT
CGACACATCG
4021 ACAATCGTTC GCACGCCAGC CGCTCTGGCG CGGCGCAATC CTCTCACAGC
CTTTTCCGCT
4081 AGAGCTTTGC GGCTACCGAA GAACTCTGGC CAAGCACGCA AGAATCCTGC
CGAGCTGCCG
4141 CAGATGTGCT CGTGAGTCAG TGTGAAACCC GCTTCAGAGA TTGTGATAGG
ACCGCGCACG
4201 GTATTGATCC GATCGCCGGA ATTCATTCTG TGTAATTCGG TACCTAATTC

FIG. 7c

```
     CCAATTCCCT
4261 ATTCAGAGTT CTCTTCTTGT ATTCAATAAT TACTTCTTGG CAGATTTCAG
     TAGTTGCAGT
4321 TGATTTACTT GGTTGCTGGT TACTTTTAAT TGATTCACTT TAACTTGCAC
     TTTACTGCAG
4381 ATTGTTTAGC TTGTTCAGCT GCGCTTGTTT ATTTGCTTAG CTTTCGCTTA
     GCGACGTGTT
4441 CACTTTGCTT GTTTGAATTG AATTGTCGCT CCGTAGACGA AGCGCCTCTA
     TTTATACTCC
4501 GGCGCTCTTT TCGCGAACAT TCGAGGCGCG CTCTCTCGAA CCAACGAGAG
     CAGTATGCCG
4561 TTTACTGTGT GACAGAGTGA GAGAGCATTA GTGCAGAGAG GGAGAGACCC
     AAAAAGAAAA
4621 GAGAGAATAA CGAATAACGG CCAGAGAAAT TTCTCGAGGG GGGGCCCTGT
     GCACGATGTT
4681 TTGTTTTGAC GGACCCCTTA CTCTCGTCTC ATATAAACCG AAGCCAGCTA
     AGATGGTATA
4741 CTTATTATCA TCTTGTGATG AGGATGCTTC TATCAACGAA AGTACCGGTA
     AACCGCAAAT
4801 GGTTATGTAT TATAATCAAA CTAAAGGCGG AGTGGACACG CTAGACCAAA
     TGTGTTCTGT
4861 GATGACCTGC AGTAGGAAGA CGAATAGGTG GCCTATGGCA TTATTGTACG
     GAATGATAAA
4921 CATTGCCTGC ATAAATTCTT TTATTATATA CAGCCATAAT GTCAGTAGCA
     AGGGAGAAAA
4981 GGTTCAAAGT CGCAAAAAAT TTATGAGAAA CCTTTACATG AGCCTGACGT
     CATCGTTTAT
5041 GCGTAACCGT TTAGAAGCTC CTACTTTGAA GAGATATTTG CGCGATAATA
     TCTCTAATAT
5101 TTTGCCAAAT GAAGTGCCTG GTACATCAGA TGACAGTACT GAAGAGCCAG
     TAATGAAAAA
5161 ACGTACTTAC TGTACTTACT GCCCCTCTAA AATAAGGCGA AAGGCAAATG
     CATCGTGCAA
5221 AAAATGCAAA AAAGTTATTT GTCGAGAGCA TAATATTGAT ATGTGCCAAA
     GTTGTTTCTG
5281 GACTGACTAA TAAGTATAAT TTGTTTCTAT TATGTATAAG TTAAGCTAAT
     TACTTATTTT
5341 ATAATACAAC ATGACTGTTT TTAAAGTACA AAATAAGTTT ATTTTTGTAA
     AAGAGAGAAT
5401 GTTTAAAAGT TTTGTTACTT TAGAAGAAAT TTTGAGTTTT TGTTTTTTTT
     TAATAAATAA
5461 ATAAACATAA ATAAATTGTT TGTTGAATTT ATTATTAGTA TGTAAGTGTA
     AATATAATAA
5521 AACTTAATAT CTATTCAAAT TAATAAATAA ACCTCGATAT ACAGACCGAT
     AAAAACACAT
5581 GCGTCAATTT TACGCATGAT TATCTTTAAC GTACGTCACA ATATGATTAT
     CTTTCTAGGG
5641 TTAAATAATA GTTTCTAATT TTTTTATTAT TCAGCCTGCT GTCGTGAATA
```

FIG. 7d

```
     CCGTATATCT
5701 CAACGCTGTC TGTGAGATTG TCGTATTCTA GCCTTTTTAG TTTTTCGCTC
ATCGACTTGA
5761 TATTGTCCGA CACATTTTCG TCGATTTGCG TTTTGATCAA AGACTTGAGC
AGAGACACGT
5821 TAATCAACTG TTCAAATTGA TCCATATTAA CGATATCAAC CCGATGCGTA
TATGGTGCGT
5881 AAAATATATT TTTTAACCCT CTTATACTTT GCACTCTGCG TTAATACGCG
TTCGTGTACA
5941 GACGTAATCA TGTTTTCTTT TTTGGATAAA ACTCCTACTG AGTTTGACCT
CATATTAGAC
6001 CCTCACAAGT TGCAAAACGT GGCATTTTTT ACCAATGAAG AATTTAAAGT
TATTTTAAAA
6061 AATTTCATCA CAGATTTAAA GAAGAACCAA AAATTAAATT ATTTAATCGA
CCAGTTAATC
6121 AACGTGTACA CAGAGCGCAA AAAACACGCA GCCCGACGTG TTGGCTAAAA
TTATTAAATC
6181 AACTTGTGTT ATAGTCACGA TTTGCCGTCC AACGTGTTCC TCAAAAAGTT
GAAGACCAAC
6241 AAGTTTACGG ACACTAGTTA ATTATTTGAT TTTGCCCCAC TTCATTTTGT
GGGATCACAA
6301 TTTTGTTATA TTTTAAACAA AGCTTGGCAC TGGCCGTCGT TTTACAACGT
CGTGACTGGG
6361 AAAACCCTGG CGTTACCCAA CTTAATCGCC TTGCAGCACA TCCCCCTTTC
GCCAGCTGGC
6421 GTAATAGCGA AGAGGCCCGC ACCGATCGCC CTTCCCAACA GTTGCGCAGC
CTGAATGGCG
6481 AATGGCGCCT GATGCGGTAT TTTCTCCTTA CGCATCTGTG CGGTATTTCA
CACCGCATAT
6541 GGTGCACTCT CAGTACAATC TGCTCTGATG CCGCATAGTT AAGCCAGCCC
CGACACCCGC
6601 CAACACCCGC TGACGCGCCC TGACGGGCTT GTCTGCTCCC GGCATCCGCT
TACAGACAAG
6661 CTGTGACCGT CTCCGGGAGC TGCATGTGTC AGAGGTTTTC ACCGTCATCA
CCGAAACGCG
6721 CGA
```

FIG. 7e

```
                                                          >AseI
                                                          |
                                                          | 50
     *         *         *         *         |  *
AGCGC CCAAT ACGCA AACCG CCTCT CCCCG CGCGT TGGCC GATTC ATTAA
                                                             100
     *         *         *         *              *
TGCAG CTGGC ACGAC AGGTT TCCCG ACTGG AAAGC GGGCA GTGAG CGCAA
        >AseI
        |
        |                                                    150
     |  *      *         *         *              *
CGCAA TTAAT GTGAG TTAGC TCACT CATTA GGCAC CCCAG GCTTT ACACT
                                                             200
     *         *         *         *              *
TTATG CTTCC GGCTC GTATG TTGTG TGGAA TTGTG AGCGA ATAAC AATTT
                                                             250
     *         *         *         *              *
CACAC AGGAA ACAGC TATGA CCATG ATTAC GCCAA GCTAT TTAGG TGACA
                              >HindIII        >BamHI
                              |                |
                              |                |             300
     *         *         |  *              *   |
CTATA GAATA CTCAA GCTAT GCATC AAGCT TGGTA CCGAG CTCGG ATCCA
                                        >BamHI  >XbaI
                                        |       |
                                        |       |            350
     *         *         *         |  *   |
CTAGT AACGG CCGCC AGTGT GCTGG AATTC GGCTT GGATC CTCTA GACCC
                                                             400
     *         *         *         *              *
TAGAA AGATA GTCTG CGTAA AATTG ACGCA TGCAT TCTTG AAATA TTGCT
                                                             450
     *         *         *         *              *
CTCTC TTTCT AAATA GCGCG AATCC GTCGC TGTTT GCAAT TTAGG ACATC
                                                             500
     *         *         *         *              *
TCAGT CGCCG CTTGG AGCTC GGCTG AGGCG TGCTT GTCAA TGCGG TAAGT
```

FIG. 9a

```
                                                              550
       *           *           *           *            *
GTCAC TGATT TTGAA CTATA ACGAC CGCGT GAGTC AAAAT GACGC ATGAT
                                            >AseI
                                              |
                                              |              600
       *           *           *           *  |         *
TATCT TTTAC GTGAC TTTTA AGATT TAACT CATAC GATAA TTAAT ATTGT
                                                              650
       *           *           *           *            *
TATTT CATGT TCTAC TTACG TGATA ACTTA TTATA TATAT ATTTT CTTGT
     >EcoRV
       |
       |   *           *           *           *            700
       |   *           *           *           *        *
TATAG ATATC GTGAC TAATA TATAA TAAAA TGGGA TGTTC TTTAG ACGAT
                                                              750
       *           *           *           *            *
GAGCA TATCC TCTCT GCTCT TCTGC AAGGC GATGA CGAGC TTGTT GGTGA
                                                              800
       *           *           *           *            *
GGATT CTGAC AGTGA AATAT CAGAT CACGT AAGTG AAGAC GTCCA GAGCG
                                                              850
       *           *           *           *            *
ATACA GAAGA AGCGT TTATA GATGA GGTAC ATGAA GTGTC AGCCA ACGTC
                                                              900
       *           *           *           *            *
AAGCG TAGTG AAATA TTAGA CGAAC AAAAT GTTAT TGAAC AACCA GGTTC
                                                              950
       *           *           *           *            *
TTCAT TGGCT TCTAA CAGAA TCTTG ACCTT GCCAC AGAGG ACTAT TAGAG
                                                              1000
       *           *           *           *            *
GTAAG AATAA ACATT GTTGG TCAAC TTCAA AGTCC ACGAG CGGTA GCCGA
                        >BglII              >MluI
                           |                   |
                           |                   |              1050
       *           *       |   *           *            *
GTCTC TGCAC TGAAC ATTGT CAGAT CTCAA AGAGG TCCGA CGCGT ATGTG
                                                              1100
       *           *           *           *            *
CCGCA ATATA TATGA CCCAC TTTTA TGCTT CAAAC TATTT TTTAC TGATG
                                                   >EcoRV
                                                      |
                                                      |       1150
       *           *           *           *         |  *
AGATA ATTTC GCAAA TTGTA AAATG GACAA ATGCT GAGAT ATCAT TGAAA
                                                              1200
```

FIG. 9b

```
CGTCG GGAAT CTATG ACAGG TGCTA CATTT CGTGA CACGA ATGAA GATGA
                                                         1250
AATCT ATGCT TTCTT TGGTA TTCTG GTAAT GACAG CAGTG AGAAA AGATA
                                                         1300
ACCAC ATGTC CACAG ATGAC CTCTT TGGAT CGATC TTTGT CAATG TGTAC
                                                         1350
GTCTC TGTAA TGAGT CTGTG GATCG TTTTG GATTT TTTGA TACGA TGTCT
                                                         1400
TAGAA TGGAT GACAA AAGTA TACGG CCCAC ACTTC GAGAA AACGA TGTAT
                                                         1450
TTACT CCTGT TAGAA AAATA TGGGA TCTCT TTATC CATCA GTGCA TACAA
                                                         1500
AATTA CACTC CAGGG GCTCA TTTGA CCATA GATGA ACAGT TACTT GGTTT
                                                         1550
TAGAG GACGG TGTCC GTTTA GGATG TATAT CCCAA ACAAG CCAAG TAAGT
                                                         1600
ATGGA ATAAA AATCC TCATG ATGTG TGACA GTGGT ACGAA GTATA TGATA
                                                         1650
AATGG AATGC CTTAT TTGGG AAGAG GAACA CAGAC CAACG GAGTA CCACT
                                                         1700
CGGTG AATAC TACGT GAAGG AGTTA TCAAA GCCTG TGCAC GGTAG TTGTC
                                                         1750
GTAAT ATTAC GTGTG ACAAT TGGTT CACCT CAATC CCTTT GGCAA AAAAC
                >HpaI
                                                         1800
TTACT ACAAG AACCG TATAA GTTAA CCATT GTGGG AACCG TGCGA TCAAA
                                                         1850
CAAAC GCGAG ATACC GGAAG TACTG AAAAA CAGTC GCTCC AGGCC AGTGG
                                                         1900
GAACA TCGAT GTTTT GTTTT GACGG ACCCC TTACT CTCGT CTCAT ATAAA
```

FIG. 9c

```
                  *              *              *              *         1950
                                                                            *
     CCGAA GCCAG CTAAG ATGGT ATACT TATTA TCATC TTGTG ATGAG GATGC
                                                                         2000
                  *              *              *              *           *
     TTCTA TCAAC GAAAG TACCG GTAAA CCGCA AATGG TTATG TATTA TAATC
                                                                         2050
                  *              *              *              *           *
     AAACT AAAGG CGGAG TGGAC ACGCT AGACC AAATG TGTTC TGTGA TGACC
      >PstI
          |
          |                                                              2100
          |       *              *              *              *           *
     TGCAG TAGGA AGACG AATAG GTGGC CTATG GCATT ATTGT ACGGA ATGAT
                                                                         2150
                  *              *              *              *           *
     AAACA TTGCC TGCAT AAATT CTTTT ATTAT ATACA GCCAT AATGT CAGTA
                      >XmnI
                          |
                          |                                              2200
                  *       |      *              *              *           *
     GCAAG GGAGA AAAGG TTCAA AGTCG CAAAA AATTT ATGAG AAACC TTTAC
                                                                         2250
                  *              *              *              *           *
     ATGAG CCTGA CGTCA TCGTT TATGC GTAAC CGTTT AGAAG CTCCT ACTTT
                                                                         2300
                  *              *              *              *           *
     GAAGA GATAT TTGCG CGATA ATATC TCTAA TATTT TGCCA AATGA AGTGC
                                                                         2350
                  *              *              *              *           *
     CTGGT ACATC AGATG ACAGT ACTGA AGAGC CAGTA ATGAA AAAAC GTACT
                                                                         2400
                  *              *              *              *           *
     TACTG TACTT ACTGC CCCTC TAAAA TAAGG CGAAA GGCAA ATGCA TCGTG
                                                                         2450
                  *              *              *              *           *
     CAAAA AATGC AAAAA AGTTA TTTGT CGAGA GCATA ATATT GATAT GTGCC
                                                                         2500
                  *              *              *              *           *
     AAAGT TGTTT CTGGA CTGAC TAATA AGTAT AATTT GTTTC TATTA TGTAT
                                                                         2550
                  *              *              *              *           *
     AAGTT AAGCT AATTA CTTAT TTTAT AATAC AACAT GACTG TTTTT AAAGT
                                                                         2600
                  *              *              *              *           *
     ACAAA ATAAG TTTAT TTTTG TAAAA GAGAG AATGT TTAAA AGTTT TGTTA
                                                                         2650
```

FIG. 9d

```
          *         *         *         *         *
CTTTA GAAGA AATTT TGAGT TTTTG TTTTT TTTTA ATAAA TAAAT AAACA
                                                      2700
          *         *         *         *         *
TAAAT AAATT GTTTG TTGAA TTTAT TATTA GTATG TAAGT GTAAA TATAA
                      >AseI
                        |
                        |                             2750
          *         *   |     *         *         *
TAAAA CTTAA TATCT ATTCA AATTA ATAAA TAAAC CTCGA TATAC AGACC
                                                      2800
          *         *         *         *         *
GATAA AAACA CATGC GTCAA TTTTA CGCAT GATTA TCTTT AACGT ACGTC
                            >BamHI  >XbaI                >PstI
                              |       |                    |
                              |       |                  2850
          *         *   |     *  |      *         *         *
ACAAT ATGAT TATCT TTCTA GGGGG ATCCT CTAGA AAGCC GAATT CTGCA
>EcoRV                                >XbaI
  |                                     |
  |                                     |             2900
  |       *         *         *         |  *         *
GATAT CCATC ACACT GGCGG CCGCT CGAGC ATGCA TCTAG AGGGC CCAAT
                                                      2950
          *         *         *         *         *
TCGCC CTATA GTGAG TCGTA TTACA ATTCA CTGGC CGTCG TTTTA CAACG
                                                      3000
          *         *         *         *         *
TCGTG ACTGG GAAAA CCCTG GCGTT ACCCA ACTTA ATCGC CTTGC AGCAC
                                                      3050
          *         *         *         *         *
ATCCC CCTTT CGCCA GCTGG CGTAA TAGCG AAGAG GCCCG CACCG ATCGC
                                                      3100
          *         *         *         *         *
CCTTC CCAAC AGTTG CGCAG CCTGA ATGGC GAATG GGACG CGCCC TGTAG
                                                      3150
          *         *         *         *         *
CGGCG CATTA AGCGC GGCGG GTGTG GTGGT TACGC GCAGC GTGAC CGCTA
                                                      3200
          *         *         *         *         *
CACTT GCCAG CGCCC TAGCG CCCGC TCCTT TCGCT TTCTT CCCTT CCTTT
                                                      3250
          *         *         *         *         *
CTCGC CACGT TCGCC GGCTT TCCCC GTCAA GCTCT AAATC GGGGG CTCCC
                                                      3300
          *         *         *         *         *
TTTAG GGTTC CGATT TAGAG CTTTA CGGCA CCTCG ACCGC AAAAA ACTTG
```

FIG. 9e

```
                                            3350
ATTTG GGTGA TGGTT CACGT AGTGG GCCAT CGCCC TGATA GACGG TTTTT
                                            3400
CGCCC TTTGA CGTTG GAGTC CACGT TCTTT AATAG TGGAC TCTTG TTCCA
                                            3450
AACTG GAACA ACACT CAACC CTATC GCGGT CTATT CTTTT GATTT ATAAG
                                            3500
GGATT TTGCC GATTT CGGCC TATTG GTTAA AAAAT GAGCT GATTT AACAA
                                            3550
ATTCA GGGCG CAAGG GCTGC TAAAG GAACC GGAAC ACGTA GAAAG CCAGT
                                            3600
CCGCA GAAAC GGTGC TGACC CCGGA TGAAT GTCAG CTACT GGGCT ATCTG
                                            3650
GACAA GGGAA AACGC AAGCG CAAAG AGAAA GCAGG TAGCT TGCAG TGGGC
                                            3700
TTACA TGGCG ATAGC TAGAC TGGGC GGTTT TATGG ACAGC AAGCG AACCG
                                            3750
GAATT GCCAG CTGGG GCGCC CTCTG GTAAG GTTGG GAAGC CCTGC AAAGT
                                            >BglII
                                            3800
AAACT GGATG GCTTT CTTGC CGCCA AGGAT CTGAT GGCGC AGGGG ATCAA
                                            3850
GATCT GATCA AGAGA CAGGA TGAGG ATCGT TTCGC ATGAT TGAAC AAGAT
                                            3900
GGATT GCACG CAGGT TCTCC GGCCG CTTGG GTGGA GAGGC TATTC GGCTA
                                            3950
TGACT GGGCA CAACA GACAA TCGGC TGCTC TGATG CCGCC GTGTT CCGGC
                                            4000
TGTCA GCGCA GGGGC GCCCG GTTCT TTTTG TCAAG ACCGA CCTGT CCGGT
      >PstI
```

FIG. 9f

```
                                                           4050
GCCCT GAATG AACTG CAGGA CGAGG CAGCG CGGCT ATCGT GGCTG GCCAC
                                                           4100
GACGG GCGTT CCTTG CGCAG CTGTG CTCGA CGTTG TCACT GAAGC GGGAA
                                                           4150
GGGAC TGGCT GCTAT TGGGC GAAGT GCCGG GGCAG GATCT CCTGT CATCT
                                                           4200
CGCCT TGCTC CTGCC GAGAA AGTAT CCATC ATGGC TGATG CAATG CGGCG
                                                           4250
GCTGC ATACG CTTGA TCCGG CTACC TGCCC ATTCG ACCAC CAAGC GAAAC
                                                           4300
ATCGC ATCGA GCGAG CACGT ACTCG GATGG AAGCC GGTCT TGTCG ATCAG
                                                           4350
GATGA TCTGG ACGAA GAGCA TCAGG GGCTC GCGCC AGCCG AACTG TTCGC
                                                           4400
CAGGC TCAAG GCGCG CATGC CCGAC GGCGA GGATC TCGTC GTGAT CCATG
                                                           4450
GCGAT GCCTG CTTGC CGAAT ATCAT GGTGG AAAAT GGCCG CTTTT CTGGA
                                                           4500
TTCAA CGACT GTGGC CGGCT GGGTG TGGCG GACCG CTATC AGGAC ATAGC
                                                           4550
GTTGG ATACC CGTGA TATTG CTGAA GAGCT TGGCG GCGAA TGGGC TGACC
                                                           4600
GCTTC CTCGT GCTTT ACGGT ATCGC CGCTC CCGAT TCGCA GCGCA TCGCC
                                                           4650
TTCTA TCGCC TTCTT GACGA GTTCT TCTGA ATTGA AAAAG GAAGA GTATG
                                                           4700
AGTAT TCAAC ATTTC CGTGT CGCCC TTATT CCCTT TTTTG CGGCA TTTTG
                                                           4750
CCTTC CTGTT TTTGC TCACC CAGAA ACGCT GGTGA AAGTA AAAGA TGCTG
                                                           4800
```

FIG. 9g

```
AAGAT CAGTT GGGTG CACGA GTGGG TTACA TCGAA CTGGA TCTCA ACAGC
                                              >XmnI
                                                                4850
GGTAA GATCC TTGAG AGTTT TCGCC CCGAA GAACG TTTTC CAATG ATGAG
                                                                4900
CACTT TTAAA GTTCT GCTAT GTGAT ACACT ATTAT CCCGT ATTGA CGCCG
                                                                4950
GGCAA GAGCA ACTCG GTCGC CGCAT ACACT ATTCT CAGAA TGACT TGGTT
                                                                5000
GAGTA CTCAC CAGTC ACAGA AAAGC ATCTT ACGGA TGGCA TGACA GTAAG
                                                                5050
AGAAT TATGC AGTGC TGCCA TAACC ATGAG TGATA ACACT GCGGC CAACT
                                                                5100
TACTT CTGAC AACGA TCGGA GGACC GAAGG AGCTA ACCGC TTTTT TGCAC
                                                                5150
AACAT GGGGG ATCAT GTAAC TCGCC TTGAT CGTTG GGAAC CGGAG CTGAA
                                                                5200
TGAAG CCATA CCAAA CGACG AGAGT GACAC CACGA TGCCT GTAGC AATGC
                                                                5250
CAACA ACGTT GCGCA AACTA TTAAC TGGCG AACTA CTTAC TCTAG CTTCC
        >AseI
                                                                5300
CGGCA ACAAT TAATA GACTG AATGG AGGCG GATAA AGTTG CAGGA CCACT
                                                                5350
TCTGC GCTCG GCCCT TCCGG CTGGC TGGTT TATTG CTGAT AAATC TGGAG
                                                                5400
CCGGT GAGCG TGGGT CTCGC GGTAT CATTG CAGCA CTGGG GCCAG ATGGT
                                                                5450
AAGCG CTCCC GTATC GTAGT TATCT ACACG ACGGG GAGTC AGGCA ACTAT
                                                                5500
```

FIG. 9h

```
GGATG AACGA AATAG ACAGA TCGCT GAGAT AGGTG CCTCA CTGAT TAAGC
                                                           5550
     *          *          *          *          *          *
ATTGG TAACT GTCAG ACCAA GTTTA CTCAT ATATA CTTTA GATTG ATTTA
                                                           5600
     *          *          *          *          *          *
AAACT TCATT TTTAA TTTAA AAGGA TCTAG GTGAA GATCC TTTTT GATAA
                                                           5650
     *          *          *          *          *          *
TCTCA TGACC AAAAT CCCTT AACGT GAGTT TTCGT TCCAC TGAGC GTCAG
                                                           5700
     *          *          *          *          *          *
ACCCC GTAGA AAAGA TCAAA GGATC TTCTT GAGAT CCTTT TTTTC TGCGC
                                                           5750
     *          *          *          *          *          *
GTAAT CTGCT GCTTG CAAAC AAAAA AACCA CCGCT ACCAG CGGTG GTTTG
                                                           5800
     *          *          *          *          *          *
TTTGC CGGAT CAAGA GCTAC CAACT CTTTT TCCGA AGGTA ACTGG CTTCA
                                                           5850
     *          *          *          *          *          *
GCAGA GCGCA GATAC CAAAT ACTGT CCTTC TAGTG TAGCC GTAGT TAGGC
                                                           5900
     *          *          *          *          *          *
CACCA CTTCA AGAAC TCTGT AGCAC CGCCT ACATA CCTCG CTCTG CTAAT
                                                           5950
     *          *          *          *          *          *
CCTGT TACCA GTGGC TGCTG CCAGT GGCGA TAAGT CGTGT CTTAC CGGGT
                                                           6000
     *          *          *          *          *          *
TGGAC TCAAG ACGAT AGTTA CCGGA TAAGG CGCAG CGGTC GGGCT GAACG
                                                           6050
     *          *          *          *          *          *
GGGGG TTCGT GCACA CAGCC CAGCT TGGAG CGAAC GACCT ACACC GAACT
                                                           6100
     *          *          *          *          *          *
GAGAT ACCTA CAGCG TGAGC TATGA GAAAG CGCCA CGCTT CCCGA AGGGA
                                                           6150
     *          *          *          *          *          *
GAAAG GCGGA CAGGT ATCCG GTAAG CGGCA GGGTC GGAAC AGGAG AGCGC
                                                           6200
     *          *          *          *          *          *
ACGAG GGAGC TTCCA GGGGG AAACG CCTGG TATCT TTATA GTCCT GTCGG
                                                           6250
     *          *          *          *          *          *
GTTTC GCCAC CTCTG ACTTG AGCGT CGATT TTTGT GATGC TCGTC AGGGG
```

FIG. 9i

```
                                                              6300
     *         *         *         *         *
GGCGG AGCCT ATGGA AAAAC GCCAG CAACG CGGCC TTTTT ACGGT TCCTG
                                                              6350
     *         *         *         *         *
GGCTT TTGCT GGCCT TTTGC TCACA TGTTC TTTCC TGCGT TATCC CCTGA
                                                              6400
     *         *         *         *         *
TTCTG TGGAT AACCG TATTA CCGCC TTTGA GTGAG CTGAT ACCGC TCGCC

*         *         *         *
GCAGC CGAAC GACCG AGCGC AGCGA GTCAG TGAGC GAGGA AGCGG AAG
```

FIG. 9j

```
                                                                    50
         *         *         *         *         *
TCGCG CGTTT CGGTG ATGAC GGTGA AAACC TCTGA CACAT GCAGC TCCCG
                                                                   100
         *         *         *         *         *
GAGAC GGTCA CAGCT TGTCT GTAAG CGGAT GCCGG GAGCA GACAA GCCCG
                                                                   150
         *         *         *         *         *
TCAGG GCGCG TCAGC GGGTG TTGGC GGGTG TCGGG GCTGG CTTAA CTATG
                                                                   200
         *         *         *         *         *
CGGCA TCAGA GCAGA TTGTA CTGAG AGTGC ACCAT ATGCG GTGTG AAATA
                                                                   250
         *         *         *         *         *
CCGCA CAGAT GCGTA AGGAG AAAAT ACCGC ATCAG GCGCC ATTCG CCATT
                                                                   300
         *         *         *         *         *
CAGGC TGCGC AACTG TTGGG AAGGG CGATC GGTGC GGGCC TCTTC GCTAT
                                                                   350
         *         *         *         *         *
TACGC CAGCT GGCGA AAGGG GGATG TGCTG CAAGG CGATT AAGTT GGGTA
                                                    >HindIII
                                                           |
                                                                   400
         *         *         *         *         |*
ACGCC AGGGT TTTCC CAGTC ACGAC GTTGT AAAAC GACGG CCAGT GCCAA
          >PstI     >XbaI    >BamHI    >XbaI
              |         |        |         |
                                                                   450
         *    |    *    |    *   |    *    |    *
GCTTG CATGC CTGCA GGTCG ACTCT AGAGG GATCC TCTAG ATTAA CCCTA
                                                                   500
         *         *         *         *         *
GAAAG ATAGT CTGCG TAAAA TTGAC GCATG CATTC TTGAA ATATT GCTCT
                                                                   550
         *         *         *         *         *
CTCTT TCTAA ATAGC GCGAA TCCGT CGCTG TTTGC AATTT AGGAC ATCTC
                                                                   600
```

FIG. 10a

```
        *           *           *           *           *
AGTCG CCGCT TGGAG CTCGG CTGAG GCGTG CTTGT CAATG CGGTA AGTGT
                                                        650
        *           *           *           *           *
CACTG ATTTT GAACT ATAAC GACCG CGTGA GTCAA AATGA CGCAT GATTA
                                                >AseI
                                                  |
                                                  |     700
        *           *           *             | *       *
TCTTT TACGT GACTT TTAAG ATTTA ACTCA TACGA TAATT AATAT TGTTA
                                                        750
        *           *           *           *           *
TTTCA TGTTC TACTT ACGTG ATAAC TTATT ATATA TATAT TTTCT TGTTA
  >EcoRV
    |
    |                                                   800
    | *       *           *           *           *     *
TAGAT ATCGT GACTA ATATA TAATA AAATG GGATG TTCTT TAGAC GATGA
                                                        850
        *           *           *           *           *
GCATA TCCTC TCTGC TCTTC TGCAA GGCGA TGACG AGCTT GTTGG TGAGG
                                                        900
        *           *           *           *           *
ATTCT GACAG TGAAA TATCA GATCA CGTAA GTGAA GACGT CCAGA GCGAT
                                                        950
        *           *           *           *           *
ACAGA AGAAG CGTTT ATAGA TGAGG TACAT GAAGT GTCAG CCAAC GTCAA
                                                       1000
        *           *           *           *           *
GCGTA GTGAA ATATT AGACG AACAA AATGT TATTG AACAA CCAGG TTCTT
                                                       1050
        *           *           *           *           *
CATTG GCTTC TAACA GAATC TTGAC CTTGC CACAG AGGAC TATTA GAGGT
                                                       1100
        *           *           *           *           *
AAGAA TAAAC ATTGT TGGTC AACTT CAAAG TCCAC GAGCG GTAGC CGAGT
                  >BglII                >MluI
                    |                      |
                    |                      |           1150
        *           *           *        | *            *
CTCTG CACTG AACAT TGTCA GATCT CAAAG AGGTC CGACG CGTAT GTGCC
                                                       1200
        *           *           *           *           *
GCAAT ATATA TGACC CACTT TTATG CTTCA AACTA TTTTT TACTG ATGAG
                                        >EcoRV
                                           |
                                           |           1250
        *           *           *         | *           *
                              FIG. 10b
```

```
ATAAT TTCGC AAATT GTAAA ATGGA CAAAT GCTGA GATAT CATTG AAACG
                                                           1300
TCGGG AATCT ATGAC AGGTG CTACA TTTCG TGACA CGAAT GAAGA TGAAA
                                                           1350
TCTAT GCTTT CTTTG GTATT CTGGT AATGA CAGCA GTGAG AAAAG ATAAC
                                                           1400
CACAT GTCCA CAGAT GACCT CTTTG GATCG ATCTT TGTCA ATGTG TACGT
                                                           1450
CTCTG TAATG AGTCT GTGGA TCGTT TTGGA TTTTT TGATA CGATG TCTTA
                                                           1500
GAATG GATGA CAAAA GTATA CGGCC CACAC TTCGA GAAAA CGATG TATTT
                                                           1550
ACTCC TGTTA GAAAA ATATG GGATC TCTTT ATCCA TCAGT GCATA CAAAA
                                                           1600
TTACA CTCCA GGGGC TCATT TGACC ATAGA TGAAC AGTTA CTTGG TTTTA
                                                           1650
GAGGA CGGTG TCCGT TTAGG ATGTA TATCC CAAAC AAGCC AAGTA AGTAT
                                                           1700
GGAAT AAAAA TCCTC ATGAT GTGTG ACAGT GGTAC GAAGT ATATG ATAAA
                                                           1750
TGGAA TGCCT TATTT GGGAA GAGGA ACACA GACCA ACGGA GTACC ACTCG
                                                           1800
GTGAA TACTA CGTGA AGGAG TTATC AAAGC CTGTG CACGG TAGTT GTCGT
                                                           1850
AATAT TACGT GTGAC AATTG GTTCA CCTCA ATCCC TTTGG CAAAA AACTT
                    >HpaI
                                                           1900
ACTAC AAGAA CCGTA TAAGT TAACC ATTGT GGGAA CCGTG CGATC AAACA
                                                           1950
AACGC GAGAT ACCGG AAGTA CTGAA AAACA GTCGC TCCAG GCCAG TGGGA
                                                           2000
```

FIG. 10c

```
       *             *             *             *             *
ACATC GATGT TTTGT TTTGA CGGAC CCCTT ACTCT CGTCT CATAT AAACC
                                                              2050
       *             *             *             *             *
GAAGC CAGCT AAGAT GGTAT ACTTA TTATC ATCTT GTGAT GAGGA TGCTT
                                                              2100
       *             *             *             *             *
CTATC AACGA AAGTA CCGGT AAACC GCAAA TGGTT ATGTA TTATA ATCAA
                                                              2150
       *             *             *             *             *
ACTAA AGGCG GAGTG GACAC GCTAG ACCAA ATGTG TTCTG TGATG ACCTG
>PstI
  |
  |                                                           2200
  |    *             *             *             *             *
CAGTA GGAAG ACGAA TAGGT GGCCT ATGGC ATTAT TGTAC GGAAT GATAA
                                                              2250
       *             *             *             *             *
ACATT GCCTG CATAA ATTCT TTTAT TATAT ACAGC CATAA TGTCA GTAGC
             >XmnI
               |
               |                                              2300
       *       |     *             *             *             *
AAGGG AGAAA AGGTT CAAAG TCGCA AAAAA TTTAT GAGAA ACCTT TACAT
                                                              2350
       *             *             *             *             *
GAGCC TGACG TCATC GTTTA TGCGT AACCG TTTAG AAGCT CCTAC TTTGA
                                                              2400
       *             *             *             *             *
AGAGA TATTT GCGCG ATAAT ATCTC TAATA TTTTG CCAAA TGAAG TGCCT
                                                              2450
       *             *             *             *             *
GGTAC ATCAG ATGAC AGTAC TGAAG AGCCA GTAAT GAAAA AACGT ACTTA
                                                              2500
       *             *             *             *             *
CTGTA CTTAC TGCCC CTCTA AAATA AGGCG AAAGG CAAAT GCATC GTGCA
                                                              2550
       *             *             *             *             *
AAAAA TGCAA AAAAG TTATT TGTCG AGAGC ATAAT ATTGA TATGT GCCAA
                                                              2600
       *             *             *             *             *
AGTTG TTTCT GGACT GACTA ATAAG TATAA TTTGT TTCTA TTATG TATAA
                                                              2650
       *             *             *             *             *
GTTAA GCTAA TTACT TATTT TATAA TACAA CATGA CTGTT TTTAA AGTAC
                                                              2700
       *             *             *             *             *
```

FIG. 10d

```
AAAAT AAGTT TATTT TTGTA AAAGA GAGAA TGTTT AAAAG TTTTG TTACT
                                                          2750
    *         *         *         *         *
TTAGA AGAAA TTTTG AGTTT TTGTT TTTTT TTAAT AAATA AATAA ACATA
                                                          2800
    *         *         *         *         *
AATAA ATTGT TTGTT GAATT TATTA TTAGT ATGTA AGTGT AAATA TAATA
                        >AseI
                          |
                          |                               2850
    *         *   |     *         *         *
AAACT TAATA TCTAT TCAAA TTAAT AAATA AACCT CGATA TACAG ACCGA
                                                          2900
    *         *         *         *         *
TAAAA ACACA TGCGT CAATT TTACG CATGA TTATC TTTAA CGTAC GTCAC
                              >XbaI    >BamHI
                                 |        |
                                 |        |               2950
    *         *         *     | *  |      *         *
AATAT GATTA TCTTT CTAGG GTTAA TCTAG AGGAT CCGAT CCCCG GGTAC
                                                          3000
    *         *         *         *         *
CGAGC TCGAA TTCGT AATCA TGGTC ATAGC TGTTT CCTGT GTGAA ATTGT
                                                          3050
    *         *         *         *         *
TATCC GCTCA CAATT CCACA CAACA TACGA GCCGG AAGCA TAAAG TGTAA
                                          >AseI
                                            |
                                            |             3100
    *         *         *         *  |      *
AGCCT GGGGT GCCTA ATGAG TGAGC TAACT CACAT TAATT GCGTT GCGCT
                                                    >AseI
                                                      |
                                                      |   3150
    *         *         *         *                |  *
CACTG CCCGC TTTCC AGTCG GGAAA CCTGT CGTGC CAGCT GCATT AATGA
                                                          3200
    *         *         *         *         *
ATCGG CCAAC GCGCG GGGAG AGGCG GTTTG CGTAT TGGGC GCTCT TCCGC
                                                          3250
    *         *         *         *         *
TTCCT CGCTC ACTGA CTCGC TGCGC TCGGT CGTTC GGCTG CGGCG AGCGG
                                                          3300
    *         *         *         *         *
TATCA GCTCA CTCAA AGGCG GTAAT ACGGT TATCC ACAGA ATCAG GGGAT
                                                          3350
    *         *         *         *         *
AACGC AGGAA AGAAC ATGTG AGCAA AAGGC CAGCA AAAGG CCAGG AACCG
```

FIG. 10e

```
                                                                     3400
       *          *          *          *          *
TAAAA AGGCC GCGTT GCTGG CGTTT TTCCA TAGGC TCCGC CCCCC TGACG
                                                                     3450
       *          *          *          *          *
AGCAT CACAA AAATC GACGC TCAAG TCAGA GGTGG CGAAA CCCGA CAGGA
                                                                     3500
       *          *          *          *          *
CTATA AAGAT ACCAG GCGTT TCCCC CTGGA AGCTC CCTCG TGCGC TCTCC
                                                                     3550
       *          *          *          *          *
TGTTC CGACC CTGCC GCTTA CCGGA TACCT GTCCG CCTTT CTCCC TTCGG
                                                                     3600
       *          *          *          *          *
GAAGC GTGGC GCTTT CTCAA TGCTC ACGCT GTAGG TATCT CAGTT CGGTG
                                                                     3650
       *          *          *          *          *
TAGGT CGTTC GCTCC AAGCT GGGCT GTGTG CACGA ACCCC CCGTT CAGCC
                                                                     3700
       *          *          *          *          *
CGACC GCTGC GCCTT ATCCG GTAAC TATCG TCTTG AGTCC AACCC GGTAA
                                                                     3750
       *          *          *          *          *
GACAC GACTT ATCGC CACTG GCAGC AGCCA CTGGT AACAG GATTA GCAGA
                                                                     3800
       *          *          *          *          *
GCGAG GTATG TAGGC GGTGC TACAG AGTTC TTGAA GTGGT GGCCT AACTA
                                                                     3850
       *          *          *          *          *
CGGCT ACACT AGAAG GACAG TATTT GGTAT CTGCG CTCTG CTGAA GCCAG
                                                                     3900
       *          *          *          *          *
TTACC TTCGG AAAAA GAGTT GGTAG CTCTT GATCC GGCAA ACAAA CCACC
                                                                     3950
       *          *          *          *          *
GCTGG TAGCG GTGGT TTTTT TGTTT GCAAG CAGCA GATTA CGCGC AGAAA
                                                                     4000
       *          *          *          *          *
AAAAG GATCT CAAGA AGATC CTTTG ATCTT TTCTA CGGGG TCTGA CGCTC
                                                                     4050
       *          *          *          *          *
AGTGG AACGA AAACT CACGT TAAGG GATTT TGGTC ATGAG ATTAT CAAAA
                                                                     4100
       *          *          *          *          *
AGGAT CTTCA CCTAG ATCCT TTTAA ATTAA AAATG AAGTT TTAAA TCAAT
                                                                     4150
```

FIG. 10f

```
CTAAA GTATA TATGA GTAAA CTTGG TCTGA CAGTT ACCAA TGCTT AATCA
                                                        4200
GTGAG GCACC TATCT CAGCG ATCTG TCTAT TTCGT TCATC CATAG TTGCC
                                                        4250
TGACT CCCCG TCGTG TAGAT AACTA CGATA CGGGA GGGCT TACCA TCTGG
                                                        4300
CCCCA GTGCT GCAAT GATAC CGCGA GACCC ACGCT CACCG GCTCC AGATT
                                                        4350
TATCA GCAAT AAACC AGCCA GCCGG AAGGG CCGAG CGCAG AAGTG GTCCT
                              >AseI
                                                        4400
GCAAC TTTAT CCGCC TCCAT CCAGT CTATT AATTG TTGCC GGGAA GCTAG
                                                        4450
AGTAA GTAGT TCGCC AGTTA ATAGT TTGCG CAACG TTGTT GCCAT TGCTA
                                                        4500
CAGGC ATCGT GGTGT CACGC TCGTC GTTTG GTATG GCTTC ATTCA GCTCC
                                                        4550
GGTTC CCAAC GATCA AGGCG AGTTA CATGA TCCCC CATGT TGTGC AAAAA
                                                        4600
AGCGG TTAGC TCCTT CGGTC CTCCG ATCGT TGTCA GAAGT AAGTT GGCCG
                                                        4650
CAGTG TTATC ACTCA TGGTT ATGGC AGCAC TGCAT AATTC TCTTA CTGTC
                                                        4700
ATGCC ATCCG TAAGA TGCTT TTCTG TGACT GGTGA GTACT CAACC AAGTC
                                                        4750
ATTCT GAGAA TAGTG TATGC GGCGA CCGAG TTGCT CTTGC CCGGC GTCAA
                                                        4800
TACGG GATAA TACCG CGCCA CATAG CAGAA CTTTA AAAGT GCTCA TCATT
    >XmnI
                                                        4850
```

FIG. 10g

```
GGAAA ACGTT CTTCG GGGCG AAAAC TCTCA AGGAT CTTAC CGCTG TTGAG
                                                       4900
        *         *         *         *         *
ATCCA GTTCG ATGTA ACCCA CTCGT GCACC CAACT GATCT TCAGC ATCTT
                                                       4950
        *         *         *         *         *
TTACT TTCAC CAGCG TTTCT GGGTG AGCAA AAACA GGAAG GCAAA ATGCC
                                                       5000
        *         *         *         *         *
GCAAA AAAGG GAATA AGGGC GACAC GGAAA TGTTG AATAC TCATA CTCTT
                                                       5050
        *         *         *         *         *
CCTTT TTCAA TATTA TTGAA GCATT TATCA GGGTT ATTGT CTCAT GAGCG
                                                       5100
        *         *         *         *         *
GATAC ATATT TGAAT GTATT TAGAA AAATA AACAA ATAGG GGTTC CGCGC
                                                       5150
        *         *         *         *         *
ACATT TCCCC GAAAA GTGCC ACCTG ACGTC TAAGA AACCA TTATT ATCAT
        *         *         *         *
GACAT TAACC TATAA AAATA GGCGT ATCAC GAGGC CCTTT CGTC
```

FIG. 10h

```
                                                                    50
         *         *         *         *         *
GACGA AAGGG CCTCG TGATA CGCCT ATTTT TATAG GTTAA TGTCA TGATA
                                                                   100
         *         *         *         *         *
ATAAT GGTTT CTTAG ACGTC AGGTG GCACT TTTCG GGGAA ATGTG CGCGG
                                                                   150
         *         *         *         *         *
AACCC CTATT TGTTT ATTTT TCTAA ATACA TTCAA ATATG TATCC GCTCA
                                                                   200
         *         *         *         *         *
TGAGA CAATA ACCCT GATAA ATGCT TCAAT AATAT TGAAA AAGGA AGAGT
                                                                   250
         *         *         *         *         *
ATGAG TATTC AACAT TTCCG TGTCG CCCTT ATTCC CTTTT TTGCG GCATT
                                                                   300
         *         *         *         *         *
TTGCC TTCCT GTTTT TGCTC ACCCA GAAAC GCTGG TGAAA GTAAA AGATG
                                                                   350
         *         *         *         *         *
CTGAA GATCA GTTGG GTGCA CGAGT GGGTT ACATC GAACT GGATC TCAAC
                                        >XmnI
                                          |
                                          |                        400
         *         *         *         *  | *
AGCGG TAAGA TCCTT GAGAG TTTTC GCCCC GAAGA ACGTT TTCCA ATGAT
                                                                   450
         *         *         *         *         *
GAGCA CTTTT AAAGT TCTGC TATGT GGCGC GGTAT TATCC CGTAT TGACG
                                                                   500
         *         *         *         *         *
CCGGG CAAGA GCAAC TCGGT CGCCG CATAC ACTAT TCTCA GAATG ACTTG
                                                                   550
         *         *         *         *         *
GTTGA GTACT CACCA GTCAC AGAAA AGCAT CTTAC GGATG GCATG ACAGT
                                                                   600
         *         *         *         *         *
AAGAG AATTA TGCAG TGCTG CCATA ACCAT GAGTG ATAAC ACTGC GGCCA
                                                                   650
```

FIG. 11a

```
ACTTA CTTCT GACAA CGATC GGAGG ACCGA AGGAG CTAAC CGCTT TTTTG
                                                            700
CACAA CATGG GGGAT CATGT AACTC GCCTT GATCG TTGGG AACCG GAGCT
                                                            750
GAATG AAGCC ATACC AAACG ACGAG CGTGA CACCA CGATG CCTGT AGCAA
                                                            800
TGGCA ACAAC GTTGC GCAAA CTATT AACTG GCGAA CTACT TACTC TAGCT
            >AseI
            |
            |                                               850
TCCCG GCAAC AATTA ATAGA CTGGA TGGAG GCGGA TAAAG TTGCA GGACC
                                                            900
ACTTC TGCGC TCGGC CCTTC CGGCT GGCTG GTTTA TTGCT GATAA ATCTG
                                                            950
GAGCC GGTGA GCGTG GTCT CGCGG TATCA TTGCA GCACT GGGGC CAGAT
                                                            1000
GGTAA GCCCT CCCGT ATCGT AGTTA TCTAC ACGAC GGGGA GTCAG GCAAC
                                                            1050
TATGG ATGAA CGAAA TAGAC AGATC GCTGA GATAG GTGCC TCACT GATTA
                                                            1100
AGCAT TGGTA ACTGT CAGAC CAAGT TTACT CATAT ATACT TTAGA TTGAT
                                                            1150
TTAAA ACTTC ATTTT TAATT TAAAA GGATC TAGGT GAAGA TCCTT TTTGA
                                                            1200
TAATC TCATG ACCAA AATCC CTTAA CGTGA GTTTT CGTTC CACTG AGCGT
                                                            1250
CAGAC CCCGT AGAAA AGATC AAAGG ATCTT CTTGA GATCC TTTTT TTCTG
                                                            1300
CGCGT AATCT GCTGC TTGCA AACAA AAAAA CCACC GCTAC CAGCG GTGGT
                                                            1350
TTGTT TGCCG GATCA AGAGC TACCA ACTCT TTTTC CGAAG GTAAC TGGCT
```

FIG. 11b

```
                                                                   1400
            *         *         *         *           *
TCAGC AGAGC GCAGA TACCA AATAC TGTCC TTCTA GTGTA GCCGT AGTTA
                                                                   1450
      *         *         *         *           *
GGCCA CCACT TCAAG AACTC TGTAG CACCG CCTAC ATACC TCGCT CTGCT
                                                                   1500
      *         *         *         *           *
AATCC TGTTA CCAGT GGCTG CTGCC AGTGG CGATA AGTCG TGTCT TACCG
                                                                   1550
      *         *         *         *           *
GGTTG GACTC AAGAC GATAG TTACC GGATA AGGCG CAGCG GTCGG GCTGA
                                                                   1600
      *         *         *         *           *
ACGGG GGGTT CGTGC ACACA GCCCA GCTTG GAGCG AACGA CCTAC ACCGA
                                                                   1650
      *         *         *         *           *
ACTGA GATAC CTACA GCGTG AGCAT TGAGA AAGCG CCACG CTTCC CGAAG
                                                                   1700
      *         *         *         *           *
GGAGA AAGGC GGACA GGTAT CCGGT AAGCG GCAGG GTCGG AACAG GAGAG
                                                                   1750
      *         *         *         *           *
CGCAC GAGGG AGCTT CCAGG GGGAA ACGCC TGGTA TCTTT ATAGT CCTGT
                                                                   1800
      *         *         *         *           *
CGGGT TTCGC CACCT CTGAC TTGAG CGTCG ATTTT TGTGA TGCTC GTCAG
                                                                   1850
      *         *         *         *           *
GGGGG CGGAG CCTAT GGAAA AACGC CAGCA ACGCG GCCTT TTTAC GGTTC
                                                                   1900
      *         *         *         *           *
CTGGC CTTTT GCTGG CCTTT TGCTC ACATG TTCTT TCCTG CGTTA TCCCC
                                                                   1950
      *         *         *         *           *
TGATT CTGTG GATAA CCGTA TTACC GCCTT TGAGT GAGCT GATAC CGCTC
                                                                   2000
      *         *         *         *           *
GCCGC AGCCG AACGA CCGAG CGCAG CGAGT CAGTG AGCGA GGAAG CGGAA
                                                                >AseI
                                                                   |
                                                                   2050
                                                                   | *
GAGCG CCCAA TACGC AAACC GCCTC TCCCC GCGCG TTGGC CGATT CATTA
                                                                   2100
      *         *         *         *           *
ATGCA GCTGG CACGA CAGGT TTCCC GACTG GAAAG CGGGC AGTGA GCGCA
```

FIG. 11c

```
                >AseI
                 |
                 |     *           *           *           *        2150
                 | *                                                  *
         ACGCA ATTAA TGTGA GTTAG CTCAC TCATT AGGCA CCCCA GGCTT TACAC
                                                                  2200
             *           *           *           *                  *
         TTTAT GCTTC CGGCT CGTAT GTTGT GTGGA ATTGT GAGCG GATAA CAATT
                                                                  2250
             *           *           *           *                  *
         TCACA CAGGA AACAG CTATG ACCAT GATTA CGAAT TCGAG CTCGG TACCC
                  >BamHI   >XbaI
                   |        |
                   |        |    *           *           *        2300
                   | *      |                                        *
         GGGGA TCGGA TCCTC TAGAT TAACC CTAGA AAGAT AGTCT GCGTA AAATT
                                                                  2350
             *           *           *           *                  *
         GACGC ATGCA TTCTT GAAAT ATTGC TCTCT CTTTC TAAAT AGCGC GAATC
                                                                  2400
             *           *           *           *                  *
         CGTCG CTGTT TGCAA TTTAG GACAT CTCAG TCGCC GCTTG GAGCT CGGCT
                                                                  2450
             *           *           *           *                  *
         GAGGC GTGCT TGTCA ATGCG GTAAG TGTCA CTGAT TTTGA ACTAT AACGA
                                                                  2500
             *           *           *           *                  *
         CCGCG TGAGT CAAAA TGACG CATGA TTATC TTTTA CGTGA CTTTT AAGAT
                            >AseI
                             |
                             |  *           *           *        2550
                             | *                                    *
         TTAAC TCATA CGATA ATTAA TATTG TTATT TCATG TTCTA CTTAC GTGAT
                                            >EcoRV
                                             |
                                             |  *           *    2600
                             *           *   |                      *
         AACTT ATTAT ATATA TATTT TCTTG TTATA GATAT CGTGA CTAAT ATATA
                                                                  2650
             *           *           *           *                  *
         ATAAA ATGGG ATGTT CTTTA GACGA TGAGC ATATC CTCTC TGCTC TTCTG
                                                                  2700
             *           *           *           *                  *
         CAAGG CGATG ACGAG CTTGT TGGTG AGGAT TCTGA CAGTG AAATA TCAGA
                                                                  2750
             *           *           *           *                  *
         TCACG TAAGT GAAGA CGTCC AGAGC GATAC AGAAG AAGCG TTTAT AGATG
                                                                  2800
```

FIG. 11d

```
      *           *           *           *           *
AGGTA CATGA AGTGT CAGCC AACGT CAAGC GTAGT GAAAT ATTAG ACGAA
                                                      2850
      *           *           *           *           *
CAAAA TGTTA TTGAA CAACC AGGTT CTTCA TTGGC TTCTA ACAGA ATCTT
                                                      2900
      *           *           *           *           *
GACCT TGCCA CAGAG GACTA TTAGA GGTAA GAATA AACAT TGTTG GTCAA
                                                   >BglII
                                                      |
                                                      2950
                                                      | *
CTTCA AAGTC CACGA GCGGT AGCCG AGTCT CTGCA CTGAA CATTG TCAGA
           >MluI
            |
            |                                         3000
      *     | *   *           *           *           *
TCTCA AAGAG GTCCG ACGCG TATGT GCCGC AATAT ATATG ACCCA CTTTT
                                                      3050
      *           *           *           *           *
ATGCT TCAAA CTATT TTTTA CTGAT GAGAT AATTT CGCAA ATTGT AAAAT
                 >EcoRV
                  |
                  |                                   3100
      *           | *       *           *             *
GGACA AATGC TGAGA TATCA TTGAA ACGTC GGGAA TCTAT GACAG GTGCT
                                                      3150
      *           *           *           *           *
ACATT TCGTG ACACG AATGA AGATG AAATC TATGC TTTCT TTGGT ATTCT
                                                      3200
      *           *           *           *           *
GGTAA TGACA GCAGT GAGAA AAGAT AACCA CATGT CCACA GATGA CCTCT
                                                      3250
      *           *           *           *           *
TTGGA TCGAT CTTTG TCAAT GTGTA CGTCT CTGTA ATGAG TCTGT GGATC
                                                      3300
      *           *           *           *           *
GTTTT GGATT TTTTG ATACG ATGTC TTAGA ATGGA TGACA AAAGT ATACG
                                                      3350
      *           *           *           *           *
GCCCA CACTT CGAGA AAACG ATGTA TTTAC TCCTG TTAGA AAAAT ATGGG
                                                      3400
      *           *           *           *           *
ATCTC TTTAT CCATC AGTGC ATACA AAATT ACACT CCAGG GGCTC ATTTG
                                                      3450
      *           *           *           *           *
ACCAT AGATG AACAG TTACT TGGTT TTAGA GGACG GTGTC CGTTT AGGAT
```

FIG. 11e

```
                                                                3500
      *            *            *            *              *
GTATA TCCCA AACAA GCCAA GTAAG TATGG AATAA AAATC CTCAT GATGT
                                                                3550
      *            *            *            *              *
GTGAC AGTGG TACGA AGTAT ATGAT AAATG GAATG CCTTA TTTGG GAAGA
                                                                3600
      *            *            *            *              *
GGAAC ACAGA CCAAC GGAGT ACCAC TCGGT GAATA CTACG TGAAG GAGTT
                                                                3650
      *            *            *            *              *
ATCAA AGCCT GTGCA CGGTA GTTGT CGTAA TATTA CGTGT GACAA TTGGT
                                                             >HpaI
                                                                |
                                                                3700
      *            *            *            *            |*
TCACC TCAAT CCCTT TGGCA AAAAA CTTAC TACAA GAACC GTATA AGTTA
                                                                3750
      *            *            *            *              *
ACCAT TGTGG GAACC GTGCG ATCAA ACAAA CGCGA GATAC CGGAA GTACT
                                                                3800
      *            *            *            *              *
GAAAA ACAGT CGCTC CAGGC CAGTG GGAAC ATCGA TGTTT TGTTT TGACG
                                                                3850
      *            *            *            *              *
GACCC CTTAC TCTCG TCTCA TATAA ACCGA AGCCA GCTAA GATGG TATAC
                                                                3900
      *            *            *            *              *
TTATT ATCAT CTTGT GATGA GGATG CTTCT ATCAA CGAAA GTACC GGTAA
                                                                3950
      *            *            *            *              *
ACCGC AAATG GTTAT GTATT ATAAT CAAAC TAAAG GCGGA GTGGA CACGC
                                     >PstI
                                        |
                                        |                       4000
      *            *            *            *              *
TAGAC CAAAT GTGTT CTGTG ATGAC CTGCA GTAGG AAGAC GAATA GGTGG
                                                                4050
      *            *            *            *              *
CCTAT GGCAT TATTG TACGG AATGA TAAAC ATTGC CTGCA TAAAT TCTTT
                                                   >XmnI
                                                      |
                                                      |         4100
      *            *            *            *     |*
TATTA TATAC AGCCA TAATG TCAGT AGCAA GGGAG AAAAG GTTCA AAGTC
                                                                4150
      *            *            *            *              *
GCAAA AAATT TATGA GAAAC CTTTA CATGA GCCTG ACGTC ATCGT TTATG
```

FIG. 11f

```
                                                              4200
        *           *           *           *             *
CGTAA CCGTT TAGAA GCTCC TACTT TGAAG AGATA TTTGC GCGAT AATAT
                                                              4250
        *           *           *           *             *
CTCTA ATATT TTGCC AAATG AAGTG CCTGG TACAT CAGAT GACAG TACTG
                                                              4300
        *           *           *           *             *
AAGAG CCAGT AATGA AAAAA CGTAC TTACT GTACT TACTG CCCCT CTAAA
                                                              4350
        *           *           *           *             *
ATAAG GCGAA AGGCA AATGC ATCGT GCAAA AAATG CAAAA AAGTT ATTTG
                                                              4400
        *           *           *           *             *
TCGAG AGCAT AATAT TGATA TGTGC CAAAG TTGTT TCTGG ACTGA CTAAT
                                                              4450
        *           *           *           *             *
AAGTA TAATT TGTTT CTATT ATGTA TAAGT TAAGC TAATT ACTTA TTTTA
                                                              4500
        *           *           *           *             *
TAATA CAACA TGACT GTTTT TAAAG TACAA AATAA GTTTA TTTTT GTAAA
                                                              4550
        *           *           *           *             *
AGAGA GAATG TTTAA AAGTT TTGTT ACTTT AGAAG AAAATT TTGAG TTTTT
                                                              4600
        *           *           *           *             *
GTTTT TTTTT AATAA ATAAA TAAAC ATAAA TAAAT TGTTT GTTGA ATTTA
                                                         >AseI
                                                           |
                                                              4650
        *           *           *           *             |*
TTATT AGTAT GTAAG TGTAA ATATA ATAAA ACTTA ATATC TATTC AAATT
                                                              4700
        *           *           *           *             *
AATAA ATAAA CCTCG ATATA CAGAC CGATA AAAAC ACATG CGTCA ATTTT
                                                              4750
        *           *           *           *             *
ACGCA TGATT ATCTT TAACG TACGT CACAA TATGA TTATC TTTCT AGGGT
 >XbaI >BamHI   >XbaI          >PstI    >HindIII
   |     |       |               |        |
   |     |       |               |        |                   4800
   |     *       | *       *     |   *    |                *
TAATC TAGAG GATCC CTCTA GAGTC GACCT GCAGG CATGC AAGCT TGGCA
                                                              4850
        *           *           *           *             *
CTGGC CGTCG TTTTA CAACG TCGTG ACTGG GAAAA CCCTG GCGTT ACCCA
                                                              4900
```

FIG. 11g

```
ACTTA ATCGC CTTGC AGCAC ATCCC CCTTT CGCCA GCTGG CGTAA TAGCG
                                                         4950
AAGAG GCCCG CACCG ATCGC CCTTC CCAAC AGTTG CGCAG CCTGA ATGGC
                                                         5000
GAATG GCGCC TGATG CGGTA TTTTC TCCTT ACGCA TCTGT GCGGT ATTTC
                                                         5050
ACACC GCATA TGGTG CACTC TCAGT ACAAT CTGCT CTGAT GCCGC ATAGT
                                                         5100
TAAGC CAGCC CCGAC ACCCG CCAAC ACCCG CTGAC GCGCC CTGAC GGGCT
                                                         5150
TGTCT GCTCC CGGCA TCCGC TTACA GACAA GCTGT GACCG TCTCC GGGAG

CTGCA TGTGT CAGAG GTTTT CACCG TCATC ACCGA AACGC GCGA
```

FIG. 11h hsp/opd new-for

5' GAA GAT CTA TTT CTC TGG CCG TTA TTC GTT AT 3' hsp/opd new-rev

5' GAA GAT CTG ATC CCG GGA ACA TAT AGA TTT AT 3'

FIG. 12a

```
                                                                    50
         *           *           *           *           *
TTAAC CCTAG AAAGA TAGTC TGCGT AAAAT TGACG CATGC ATTCT TGAAA
                                                                   100
         *           *           *           *           *
TATTG CTCTC TCTTT CTAAA TAGCG CGAAT CCGTC GCTGT TTGCA ATTTA
                                                                   150
         *           *           *           *           *
GGACA TCTCA GTCGC CGCTT GGAGC TCGGC TGAGG CGTGC TTGTC AATGC
                                                                   200
         *           *           *           *           *
GGTAA GTGTC ACTGA TTTTG AACTA TAACG ACCGC GTGAG TCAAA ATGAC
                                                                >AseI
                                                                  |
                                                                   250
         *           *           *           *        |  *
GCATG ATTAT CTTTT ACGTG ACTTT TAAGA TTTAA CTCAT ACGAT AATTA
                                                                   300
         *           *           *           *           *
ATATT GTTAT TTCAT GTTCT ACTTA CGTGA TAACT TATTA TATAT ATATT
                  >EcoRV
                   |
                                                                   350
         *     |     *           *           *           *
TTCTT GTTAT AGATA TCGTG ACTAA TATAT AATAA AATGG GATGT TCTTT
                                                                   400
         *           *           *           *           *
AGACG ATGAG CATAT CCTCT CTGCT CTTCT GCAAG GCGAT GACGA GCTTG
                                                                   450
         *           *           *           *           *
TTGGT GAGGA TTCTG ACAGT GAAAT ATCAG ATCAC GTAAG TGAAG ACGTC
```

FIG. 12b

```
                                                                      500
        *         *         *         *          *
CAGAG CGATA CAGAA GAAGC GTTTA TAGAT GAGGT ACATG AAGTG TCAGC
                                                                      550
        *         *         *         *          *
CAACG TCAAG CGTAG TGAAA TATTA GACGA ACAAA ATGTT ATTGA ACAAC
                                                                      600
        *         *         *         *          *
CAGGT TCTTC ATTGG CTTCT AACAG AATCT TGACC TTGCC ACAGA GGACT
                                                                      650
        *         *         *         *          *
ATTAG AGGTA AGAAT AAACA TTGTT GGTCA ACTTC AAAGT CCACG AGCGG
                                    >BgIII
                                       |
                                       |                              700
        *         *         *       |*          *
TAGCC GAGTC TCTGC ACTGA ACATT GTCAG ATCTG CGTCT CGAGA AATTT
                                                                      750
        *         *         *         *          *
CTCTG GCCGT TATTC GTTAT TCTCT CTTTT CTTTT TGGGT CTCTC CCTCT
                                                                      800
        *         *         *         *          *
CTGCA CTAAT GCTCT CTCAC TCTGT CACAC AGTAA ACGGC ATACT GCTCT
                                                                      850
        *         *         *         *          *
CGTTG GTTCG AGAGA GCGCG CCTCG AATGT TCGCG AAAAG AGCGC CGGAG
                                                                      900
        *         *         *         *          *
TATAA ATAGA GGCGC TTCGT CTACG GAGCG ACAAT TCAAT TCAAA CAAGC
                                                                      950
        *         *         *         *          *
AAAGT GAACA CGTCG CTAAG CGAAA GCTAA GCAAA TAAAC AAGCG CAGCT
                        >PstI
                           |
                           |                                          1000
        *         * |       *         *          *
GAACA AGCTA AACAA TCTGC AGTAA AGTGC AAGTT AAAGT GAATC AATTA
                                                                      1050
        *         *         *         *          *
AAAGT AACCA GCAAC CAAGT AAATC AACTG CAACT ACTGA AATCT GCCAA
                                                                      1100
        *         *         *         *          *
GAAGT AATTA TTGAA TACAA GAAGA GAACT CTGAA TAGGG AATTG GGAAT
                        >XmnI
                           |
                           |                                          1150
        *         * |       *         *          *
TAGGT ACCGA ATTAC ACAGA ATGAA TTCCG GCGAT CGGAT CAATA CCGTG
```

FIG. 12c

```
                                                                    1200
             *          *          *          *           *
CGCGG TCCTA TCACA ATCTC TGAAG CGGGT TTCAC ACTGA CTCAC GAGCA
                                                                    1250
      *          *          *          *           *
CATCT GCGGC AGCTC GGCAG GATTC TTGCG TGCTT GGCCA GAGTT CTTCG
                                                                    1300
      *          *          *          *           *
GTAGC CGCAA AGCTC TAGCG GAAAA GGCTG TGAGA GGATT GCGCC GCGCC
                                                           >EcoRV
                                                           |
                                                           |  1350
      *          *          *          *           |    *
AGAGC GGCTG GCGTG CGAAC GATTG TCGAT GTGTC GACTT TCGAT ATCGG
                                                                    1400
      *          *          *          *           *
TCGCG ACGTC AGTTT ATTGG CCGAG GTTTC GCGGG CTGCC GACGT TCATA
                                                                    1450
      *          *          *          *           *
TCGTG GCGGC GACCG GCTTG TGGTT CGACC CGCCA CTTTC GATGC GATTG
                                                                    1500
      *          *          *          *           *
AGGAG TGTAG AGGAA CTCAC ACAGT TCTTC CTGCG TGAGA TTCAA TATGG
                                                                    1550
      *          *          *          *           *
CATCG AAGAC ACCGG AATTA GGGCG GGCAT TATCA AGGTC GCGAC CACAG
                                                                    1600
      *          *          *          *           *
GCAAG GCGAC CCCCT TTCAG GAGTT AGTGT TAAAG GCGGC CGCCC GGGCC
                                                                    1650
      *          *          *          *           *
AGCTT GGCCA CCGGT GTTCC GGTAA CCACT CACAC GGCAG CAAGT CAGCG
                                                                    1700
      *          *          *          *           *
CGATG GTGAG CAGCA GGCCG CCATT TTTGA GTCCG AAGGC TTGAG CCCCT
                                                                    1750
      *          *          *          *           *
CACGG GTTTG TATTG GTCAC AGCGA TGATA CTGAC GATTT GAGCT ATCTC
                                              >XbaI
                                              |
                                              |                     1800
      *          *          *          |    *
ACCGC CCTCG CTGCG CGCGG ATACC TCATC GGTCT AGACC ACATC CCGCA
      >XbaI
      |
      |                                                              1850
      *    |     *          *          *           *
CAGTG CGATT GGTCT AGAAG ATAAT GCGAG TGCAT CAGCC CTCCT GGGCA
                                    FIG. 12d
```

```
                                                                           1900
      *          *          *          *            *
TCCGT TCGTG GCAAA CACGG GCTCT CTTGA TCAAG GCGCT CATCG ACCAA
                                                                           1950
      *          *          *          *            *
GGCTA CATGA AACAA ATCCT CGTTT CGAAT GACTG GCTGT TCGGG TTTTC
                                                                           2000
      *          *          *          *            *
GAGCT ATGTC ACCAA CATCA TGGAC GTGAT GGATC GCGTG AACCC CGACG
                                                                           2050
      *          *          *          *            *
GGATG GCCTT CATTC CACTG AGAGT GATCC CATTC CTACG AGAGA AGGGC
                                                                           2100
      *          *          *          *            *
GTCCC ACAGG AAACG CTGGC AGGCA TCACT GTGAC TAACC CGGCG CGGTT
                                                 >XbaI
                                                  |
                                                  |                        2150
      *          *          *          *          |  *
CTTGT CACCG ACCTT GCGGG CGTCA TGACG CCATC TGGAT CTAGA ATGGT
                                                                           2200
      *          *          *          *            *
TTATT TGTAC ACATT TACTT TAAAT TTAAT AAAAT TTACT TTAGC CGTTG
                                 >HindIII
                                     |
                                     |                                     2250
      *          *          *        |    *            *
TCCGA TAATT CTTAT ATTTA ATTTA AACCA CCTGC AAGCT TTTAA TAAAT
           >BamHI              >BglII                >MluI
               |                   |                    |
               |                   |                    |                  2300
      *        |   *          *    |     *              |*
CTATA TGTTC CCGGG ATCCA CACGC GAGAT CTCAA AGAGG TCCGA CGCGT
                                                                           2350
      *          *          *          *            *
ATGTG CCGCA ATATA TATGA CCCAC TTTTA TGCTT CAAAC TATTT TTTAC
                                                 >EcoRV
                                                   |
                                                   |                       2400
      *          *          *          *          |  *
TGATG AGATA ATTTC GCAAA TTGTA AAATG GACAA ATGCT GAGAT ATCAT
                                                                           2450
      *          *          *          *            *
TGAAA CGTCG GGAAT CTATG ACAGG TGCTA CATTT CGTGA CACGA ATGAA
                                                                           2500
      *          *          *          *            *
GATGA AATCT ATGCT TTCTT TGGTA TTCTG GTAAT GACAG CAGTG AGAAA
                                                                           2550
```

FIG. 12e

```
AGATA ACCAC ATGTC CACAG ATGAC CTCTT TGGAT CGATC TTTGT CAATG
                                                          2600
TGTAC GTCTC TGTAA TGAGT CTGTG GATCG TTTTG GATTT TTTGA TACGA
                                                          2650
TGTCT TAGAA TGGAT GACAA AAGTA TACGG CCCAC ACTTC GAGAA AACGA
                                                          2700
TGTAT TTACT CCTGT TAGAA AAATA TGGGA TCTCT TTATC CATCA GTGCA
                                                          2750
TACAA AATTA CACTC CAGGG GCTCA TTTGA CCATA GATGA ACAGT TACTT
                                                          2800
GGTTT TAGAG GACGG TGTCC GTTTA GGATG TATAT CCCAA ACAAG CCAAG
                                                          2850
TAAGT ATGGA ATAAA AATCC TCATG ATGTG TGACA GTGGT ACGAA GTATA
                                                          2900
TGATA AATGG AATGC CTTAT TTGGG AAGAG GAACA CAGAC CAACG GAGTA
                                                          2950
CCACT CGGTG AATAC TACGT GAAGG AGTTA TCAAA GCCTG TGCAC GGTAG
                                                          3000
TTGTC GTAAT ATTAC GTGTG ACAAT TGGTT CACCT CAATC CCTTT GGCAA
                        >HpaI
                          |
                          |                               3050
AAAAC TTACT ACAAG AACCG TATAA GTTAA CCATT GTGGG AACCG TGCGA
                                                          3100
TCAAA CAAAC GCGAG ATACC GGAAG TACTG AAAAA CAGTC GCTCC AGGCC
                                                          3150
AGTGG GAACA TCGAT GTTTT GTTTT GACGG ACCCC TTACT CTCGT CTCAT
                                                          3200
ATAAA CCGAA GCCAG CTAAG ATGGT ATACT TATTA TCATC TTGTG ATGAG
                                                          3250
GATGC TTCTA TCAAC GAAAG TACCG GTAAA CCGCA AATGG TTATG TATTA
```

FIG. 12f

```
                                      *                *                *                *      3300
                                                                                                   *
          TAATC  AAACT  AAAGG  CGGAG  TGGAC  ACGCT  AGACC  AAATG  TGTTC  TGTGA
                 >PstI
                     |
                     |  *             *                *                *      3350
                     |*                                                            *
          TGACC  TGCAG  TAGGA  AGACG  AATAG  GTGGC  CTATG  GCATT  ATTGT  ACGGA
                              *                *                *                *      3400
                                                                                            *
          ATGAT  AAACA  TTGCC  TGCAT  AAATT  CTTTT  ATTAT  ATACA  GCCAT  AATGT
                            >XmnI
                               |
                               |      *                *                *      3450
                               |  *                                                *
          CAGTA  GCAAG  GGAGA  AAAGG  TTCAA  AGTCG  CAAAA  AATTT  ATGAG  AAACC
                    *                *                *                *      3500
                                                                                     *
          TTTAC  ATGAG  CCTGA  CGTCA  TCGTT  TATGC  GTAAC  CGTTT  AGAAG  CTCCT
                    *                *                *                *      3550
                                                                                     *
          ACTTT  GAAGA  GATAT  TTGCG  CGATA  ATATC  TCTAA  TATTT  TGCCA  AATGA
                    *                *                *                *      3600
                                                                                     *
          AGTGC  CTGGT  ACATC  AGATG  ACAGT  ACTGA  AGAGC  CAGTA  ATGAA  AAAAC
                    *                *                *                *      3650
                                                                                     *
          GTACT  TACTG  TACTT  ACTGC  CCCTC  TAAAA  TAAGG  CGAAA  GGCAA  ATGCA
                    *                *                *                *      3700
                                                                                     *
          TCGTG  CAAAA  AATGC  AAAAA  AGTTA  TTTGT  CGAGA  GCATA  ATATT  GATAT
                    *                *                *                *      3750
                                                                                     *
          GTGCC  AAAGT  TGTTT  CTGGA  CTGAC  TAATA  AGTAT  AATTT  GTTTC  TATTA
                    *                *                *                *      3800
                                                                                     *
          TGTAT  AAGTT  AAGCT  AATTA  CTTAT  TTTAT  AATAC  AACAT  GACTG  TTTTT
                    *                *                *                *      3850
                                                                                     *
          AAAGT  ACAAA  ATAAG  TTTAT  TTTTG  TAAAA  GAGAG  AATGT  TTAAA  AGTTT
                    *                *                *                *      3900
                                                                                     *
          TGTTA  CTTTA  GAAGA  AATTT  TGAGT  TTTTG  TTTTT  TTTTA  ATAAA  TAAAT
                    *                *                *                *      3950
                                                                                     *
          AAACA  TAAAT  AAATT  GTTTG  TTGAA  TTTAT  TATTA  GTATG  TAAGT  GTAAA
                                                       >AseI
                                FIG. 12g
```

```
                                              |                                 4000
              *                 *             | *              *                  *
     TATAA TAAAA CTTAA TATCT ATTCA AATTA ATAAA TAAAC CTCGA TATAC
                                                                                 4050
              *                 *               *               *                 *
     AGACC GATAA AAACA CATGC GTCAA TTTTA CGCAT GATTA TCTTT AACGT
                                                                                 4100
              *                 *               *               *                 *
     ACGTC ACAAT ATGAT TATCT TTCTA GGGTT AAATA ATAGT TTCTA ATTTT
                                                                                 4150
              *                 *               *               *                 *
     TTTAT TATTC AGCCT GCTGT CGTGA ATACC GTATA TCTCA ACGCT GTCTG
                                                                                 4200
              *                 *               *               *                 *
     TGAGA TTGTC GTATT CTAGC CTTTT TAGTT TTTCG CTCAT CGACT TGATA
                                                                                 4250
              *                 *               *               *                 *
     TTGTC CGACA CATTT TCGTC GATTT GCGTT TTGAT CAAAG ACTTG AGCAG
                                                                      >EcoRV
                                                                         |
                                                                         |       4300
              *                 *               *               *  |              *
     AGACA CGTTA ATCAA CTGTT CAAAT TGATC CATAT TAACG ATATC AACCC
                                                                                 4350
              *                 *               *               *                 *
     GATGC GTATA TGGTG CGTAA AATAT ATTTT TTAAC CCTCT TATAC TTTGC
                    >MluI
                       |
                       |                                                         4400
              *        |        *               *               *                 *
     ACTCT GCGTT AATAC GCGTT CGTGT ACAGA CGTAA TCATG TTTTC TTTTT
                                                                                 4450
              *                 *               *               *                 *
     TGGAT AAAAC TCCTA CTGAG TTTGA CCTCA TATTA GACCC TCACA AGTTG
                                                                                 4500
              *                 *               *               *                 *
     CAAAA CGTGG CATTT TTTAC CAATG AAGAA TTTAA AGTTA TTTTA AAAAA
                                                                                 4550
              *                 *               *               *                 *
     TTTCA TCACA GATTT AAAGA AGAAC CAAAA ATTAA ATTAT TTAAT CGACC
                                                                                 4600
              *                 *               *               *                 *
     AGTTA ATCAA CGTGT ACACA GAGCG CAAAA AACAC GCAGC CCGAC GTGTT
                                                                                 4650
              *                 *               *               *                 *
     GGCTA AAATT ATTAA ATCAA CTTGT GTTAT AGTCA CGATT TGCCG TCCAA
```

FIG. 12h

```
                                                                   4700
       *           *           *           *           *
CGTGT TCCTC AAAAA GTTGA AGACC AACAA GTTTA CGGAC ACTAG TTAAT
                                                                   4750
       *           *           *           *           *
TATTT GATTT TGCCC CACTT CATTT TGTGG GATCA CAATT TTGTT ATATT
      >HindIII
            |
            |                                                      4800
            | *           *           *           *           *
TTAAA CAAAG CTTGG CACTG GCCGT CGTTT TACAA CGTCG TGACT GGGAA
                                                                   4850
       *           *           *           *           *
AACCC TGGCG TTACC CAACT TAATC GCCTT GCAGC ACATC CCCCT TTCGC
                                                                   4900
       *           *           *           *           *
CAGCT GGCGT AATAG CGAAG AGGCC CGCAC CGATC GCCCT TCCCA ACAGT
                                                                   4950
       *           *           *           *           *
TGCGC AGCCT GAATG GCGAA TGGCG CCTGA TGCGG TATTT TCTCC TTACG
                                                                   5000
       *           *           *           *           *
CATCT GTGCG GTATT TCACA CCGCA TATGG TGCAC TCTCA GTACA ATCTG
                                                                   5050
       *           *           *           *           *
CTCTG ATGCC GCATA GTTAA GCCAG CCCCG ACACC CGCCA ACACC CGCTG
                                                                   5100
       *           *           *           *           *
ACGCG CCCTG ACGGG CTTGT CTGCT CCCGG CATCC GCTTA CAGAC AAGCT
                                                                   5150
       *           *           *           *           *
GTGAC CGTCT CCGGG AGCTG CATGT GTCAG AGGTT TTCAC CGTCA TCACC
                                                                   5200
       *           *           *           *           *
GAAAC GCGCG AGACG AAAGG GCCTC GTGAT ACGCC TATTT TTATA GGTTA
                                                                   5250
       *           *           *           *           *
ATGTC ATGAT AATAA TGGTT TCTTA GACGT CAGGT GGCAC TTTTC GGGGA
                                                                   5300
       *           *           *           *           *
AATGT GCGCG GAACC CCTAT TTGTT TATTT TTCTA AATAC ATTCA AATAT
                                                                   5350
       *           *           *           *           *
GTATC CGCTC ATGAG ACAAT AACCC TGATA AATGC TTCAA TAATA TTGAA
                                                                   5400
       *           *           *           *           *
AAAGG AAGAG TATGA GTATT CAACA TTTCC GTGTC GCCCT TATTC CCTTT
```

FIG. 12i

```
                                                                      5450
TTTGC GGCAT TTTGC CTTCC TGTTT TTGCT CACCC AGAAA CGCTG GTGAA
                                                                      5500
AGTAA AAGAT GCTGA AGATC AGTTG GGTGC ACGAG TGGGT TACAT CGAAC
                                                                >XmnI
                                                                      5550
TGGAT CTCAA CAGCG GTAAG ATCCT TGAGA GTTTT CGCCC CGAAG AACGT
                                                                      5600
TTTCC AATGA TGAGC ACTTT TAAAG TTCTG CTATG TGGCG CGGTA TTATC
                                                                      5650
CCGTA TTGAC GCCGG GCAAG AGCAA CTCGG TCGCC GCATA CACTA TTCTC
                                                                      5700
AGAAT GACTT GGTTG AGTAC TCACC AGTCA CAGAA AAGCA TCTTA CGGAT
                                                                      5750
GGCAT GACAG TAAGA GAATT ATGCA GTGCT GCCAT AACCA TGAGT GATAA
                                                                      5800
CACTG CGGCC AACTT ACTTC TGACA ACGAT CGGAG GACCG AAGGA GCTAA
                                                                      5850
CCGCT TTTTT GCACA ACATG GGGGA TCATG TAACT CGCCT TGATC GTTGG
                                                                      5900
GAACC GGAGC TGAAT GAAGC CATAC CAAAC GACGA GCGTG ACACC ACGAT
                                                                      5950
GCCTG TAGCA ATGGC AACAA CGTTG CGCAA ACTAT TAACT GGCGA ACTAC
                                                      >AseI
                                                                      6000
TTACT CTAGC TTCCC GGCAA CAATT AATAG ACTGG ATGGA GGCGG ATAAA
                                                                      6050
GTTGC AGGAC CACTT GTGCG CTCGG CCCTT CCGGC TGGCT GGTTT ATTGC
                                                                      6100
TGATA AATCT GGAGC CGGTG AGCGT GGGTC TCGCG GTATC ATTGC AGCAC
                                                                      6150
```

FIG. 12j

```
TGGGG CCAGA TGGTA AGCCC TCCCG TATCG TAGTT ATCTA CACGA CGGGG
                                                          6200
AGTCA GGCAA CTATG GATGA ACGAA ATAGA CAGAT CGCTG AGATA GGTGC
                                                          6250
CTCAC TGATT AAGCA TTGGT AACTG TCAGA CCAAG TTTAC TCATA TATAC
                                                          6300
TTTAG ATTGA TTTAA AACTT CATTT TTAAT TTAAA AGGAT CTAGG TGAAG
                                                          6350
ATCCT TTTTG ATAAT CTCAT GACCA AAATC CCTTA ACGTG AGTTT TCGTT
                                                          6400
CCACT GAGCG TCAGA CCCCG TAGAA AAGAT CAAAG GATCT TCTTG AGATC
                                                          6450
CTTTT TTTCT GCGCG TAATC TGCTG CTTGC AAACA AAAAA ACCAC CGCTA
                                                          6500
CCAGC GGTGG TTTGT TTGCC GGATC AAGAG CTACC AACTC TTTTT CCGAA
                                                          6550
GGTAA CTGGC TTCAG CAGAG CGCAG ATACC AAATA CTGTC CTTCT AGTGT
                                                          6600
AGCCG TAGTT AGGCC ACCAC TTCAA GAACT CTGTA GCACC GCCTA CATAC
                                                          6650
CTCGC TCTGC TAATC CTGTT ACCAG TGGCT GCTGC CAGTG GCGAT AAGTC
                                                          6700
GTGTC TTACC GGGTT GGACT CAAGA CGATA GTTAC CGGAT AAGGC GCAGC
                                                          6750
GGTCG GGCTG AACGG GGGGT TCGTG CACAC AGCCC AGCTT GGAGC GAACG
                                                          6800
ACCTA CACCG AACTG AGATA CCTAC AGCGT GAGCA TTGAG AAAGC GCCAC
                                                          6850
GCTTC CCGAA GGGAG AAAGG CGGAC AGGTA TCCGG TAAGC GGCAG GGTCG
                                                          6900
```

FIG. 12k

```
GAACA GGAGA GCGCA CGAGG GAGCT TCCAG GGGGA AACGC CTGGT ATCTT
                                                           6950
       *          *          *          *          *
TATAG TCCTG TCGGG TTTCG CCACC TCTGA CTTGA GCGTC GATTT TTGTG
                                                           7000
       *          *          *          *          *
ATGCT CGTCA GGGGG GCGGA GCCTA TGGAA AAACG CCAGC AACGC GGCCT
                                                           7050
       *          *          *          *          *
TTTTA CGGTT CCTGG CCTTT TGCTG GCCTT TTGCT CACAT GTTCT TTCCT
                                                           7100
       *          *          *          *          *
GCGTT ATCCC CTGAT TCTGT GGATA ACCGT ATTAC CGCCT TTGAG TGAGC
                                                           7150
       *          *          *          *          *
TGATA CCGCT CGCCG CAGCC GAACG ACCGA GCGCA GCGAG TCAGT GAGCG
                                                           7200
       *          *          *          *          *
AGGAA GCGGA AGAGC GCCCA ATACG CAAAC CGCCT CTCCC CGCGC GTTGG
       >AseI
          |
          |*         *          *          *          *    7250
CCGAT TCATT AATGC AGCTG GCACG ACAGG TTTCC CGACT GGAAA GCGGG
                >AseI
                   |
                   |*      *          *          *         7300
CAGTG AGCGC AACGC AATTA ATGTG AGTTA GCTCA CTCAT TAGGC ACCCC
                                                           7350
       *          *          *          *          *
AGGCT TTACA CTTTA TGCTT CCGGC TCGTA TGTTG TGTGG AATTG TGAGC
                                                           7400
       *          *          *          *          *
GGATA ACAAT TTCAC ACAGG AAACA GCTAT GACCA TGATT ACGAA TTCGA
           >BamHI  >XbaI
              |      |
              |      |*        *          *          *     7450
GCTCG GTACC CGGGG ATCCT CTAGA GTCGA CGCTC GCGCG ACTTG GTTTG
                                                           7500
       *          *          *          *          *
CCATT CTTTA GCGCG CGTCG CGTCA CACAG CTTGG CCACA ATGTG GTTTT
                                                           7550
       *          *          *          *          *
TGTCA AACGA AGATT CTATG ACGTG TTTAA AGTTT AGGTC GAGTA AAGCG
```

FIG. 12L

CAAAT CTTTT

FIG. 12m

PIGGYBAC TRANSPOSON-BASED GENETIC TRANSFORMATION SYSTEM FOR INSECTS

This application is a non-provisional application claiming benefit of provisional application No. 60/016,234, filed Apr. 19, 1996.

BACKGROUND OF THE INVENTION

1. Field of the Invention

The present invention is directed to DNA transformation constructs encoding mobile elements and their use for transforming eukaryotic cells. In particular transposons are used as a mechanism for inserting DNA sequences into the cell's genome after introduction of the transformation construct into the cell.

2. Description of the Related Art

Certain natural DNA sequences in eukaryotic and prokaryotic cells have the ability to move from one genomic locus to a second locus. These genetic elements are referred to generally as transposable elements or transposons. Advantageously, these transposable elements can be used as tools for genetically manipulating cells. In particular, transposable elements isolated from eukaryotes are anticipated as having the greatest potential for use in producing transgenic organisms.

Transposable elements can be divided into two classes. Class I are the retro-transposons that replicate through an RNA intermediate and utilize reverse transcriptase to produce a DNA molecule that is inserted into the host cell's genome. The Class II transposons include all other mobile elements and include P, hobo, mariner, Tc1, and Ac elements (Berg & Howe, Mobile DNA, American Society for Microbiology, Washington, D.C. 1989). Members of this transposon class have short inverted repeats at their termini and generate direct duplications of a host target sequence upon insertion. Many of these elements are currently being developed as general transformation vectors in insects and plants (Rubin & Spradling, Science, Volume 218, 348–353 1982; Lidholm, Lohe & Hartl, Genetics, Volume 134, 859–868 1993; O'Brochta & Handler, Prospects and possibilities for gene transfer techniques in insects, 451–488; in Molecular Approaches to Fundamental and Applied Entomology, ed. Oakeshott et al, Springer-Verlag, New York, 1993).

The P element has been used effectively for Drosophila transformation but has limited use as a general transformation vector because it is not active in species other than Drosophila (O'Brochta & Handler, 1993 supra; Rubin & Spradling, 1982 supra). The mariner element is phylogenetically dispersed (Robertson, H. Insect Physiol., Volume 41, 99–105, 1995), and therefore apparently has the capability of movement in a number of diverse species. In addition, the hobo element has demonstrated mobility in diverse genetic backgrounds and is a promising candidate for development as a genetic engineering tool (Atkinson, Warren & O'Brochta, PNAS USA, Volume 90, 9693–9697 1993; O'Brochta & Handler, 1993 supra; O'Brochta et al., Mol. Gen. Genet., Volume 244, 9–14, 1994).

PiggyBac (previously described as IFP2) and tagalong elements are unique Lepidopteran transposons structurally related to the Class II DNA transposable elements (Finnegan, Curr. Opin, Cell Bio., Volume 2, 471–477 1990). These transposons were isolated from the cabbage looper moth, Trichoplusia ni Hubner (Lepidoptera: Noctuidae). The piggyBac element was first identified as an insertion within Galleria mellonella or Autographa californica nuclear polyhedrosis virus genomes following passage of the viruses in the Trichoplusia ni insect cell line, TN-368 (Fraser et al., Virology, Volume 145, 356–361, 1985; Fraser et al., J. Virology, Volume 47, 287–300, 1983).

The piggyBac and tagalong elements are unusual among Class II transposons in that those elements always target and duplicate the tetranucleotide, TTAA, upon insertion in Baculovirus-infected cells (Cary et al., Virology, Volume 172, 156–169, 1989). The specificity for TTAA target sites is exhibited by other Lepidopteran transposon-like insertions as well (Beames & Summers, Virology, Volume 162, 206–220 1988; Beames & Summers, Virology, Volume 174, 354–363 1990; Carstens, Virology, Volume 161, 8–17, 1987; Oellig et al., J. Virology, Volume 61, 3048–3057, 1987; Schetter, Oellig & Doerfler, J. Virology, Volume 64, 1844–1850, 1990). Thus the piggyBac and tagalong elements are part of a subclass of the Class II transposons.

In addition to TTAA target specificity, all Lepidopteran transposons having the TTAA target specificity terminate in at least two C residues at the 5' ends of their inverted repeats. Given their similarity in insertion site selection and duplication, all of these TTAA specific elements are likely to excise in a similar manner.

Furthermore piggyBac and tagalong elements excise precisely upon transposition in vivo, leaving behind the single TTAA target sequence upon excision. The excision events of piggyBac and tagalong are dissimilar to the transposase-associated excision events of the hAT family of transposons. This family includes hobo, hermes, Ac and Tam3 (Calvi et al., Cell, Volume 66, 465–471, 1991). Elements in the hAT family vary in the length and nucleotide sequence of their inverted terminal repeats (Calvi et al., 1991; supra), but have a conserved $A_2G_5$ motif within these repeats, and generate 8 bp target site duplications (Warren et al., Genet. Research, Volume 64, 87–97, 1994). These elements excise imprecisely in the presence of an element-encoded transposase and leave behind characteristic footprints that have proven useful in distinguishing transposase-associated excision events (Atkinson et al., 1993 supra; Warren et al., 1994 supra).

Most of the transposase-associated excisions of P-elements are imprecise events, leaving behind part or all of the 31 bp terminal inverted repeat and adding 'filler' sequences at the excision breakpoints (O'Brochta et al, Mol. Gen. Genet., Volume 225, 387–394, 1991: Takasu-Ishikawa et al., Mol. Gen. Genet., Volume 232, 17–23, 1992). In the case of the hobo element of Drosophila melanogaster, excision from plasmids in microinjected fertile eggs most often involves the complete removal of hobo and some flanking nucleotides with the addition of filler sequences related to flanking host DNA at the excision breakpoints (Atkinson, Warren & O'Brochta, 1993 supra; Handler & Gomez, Mol. Gen. Genet., Volume 247, 399–408 1995; O'Brochta & Handler, 1993 supra).

In contrast with these other Class II elements, precise excision of piggyBac and tagalong is the rule rather than the exception. Precise excision of genetically tagged piggyBac elements was first demonstrated in Baculovirus genomes of infected cells (Fraser et al, Virology 211, 397–407 1995). However, the precise excision of the piggyBac element has also been demonstrated in non-virus infected cells indicating the excision of piggyBac is not dependent on Baculovirus protein products. The frequency of precise excision events in transiently transfected IPLB-SF21AE cells is greatly enhanced by the presence of a helper element encoding a full-length transposase. The excision event is believed to be a non-conservative event involving double-strand breaks at or near the transposon termini.

The present invention, discussed below, provides recombinant DNA vectors derived from the piggyBac and tagalong transposons which are different from related art vectors. Furthermore, the present invention provides a method to produce transgenic organisms using the recombinant DNA vectors. The transposon genetic transformation system of the present invention provides vectors and broad spectrum methods for the introduction of foreign genes that do not currently exist.

SUMMARY OF THE INVENTION

It is therefore an object of the present invention to provide DNA sequences capable of allowing for almost precise excision of a second DNA sequence inserted into a plasmid and insertion of said second DNA sequence into a host cell after transformation of said host cell with a transformation construct containing said first and second DNAs.

Another object of the present invention is to provide transformation constructs including DNA derived from a piggyBac transposon element which allow for the almost precise excision of a second DNA sequence included in the construct and insertion of said second DNA sequence into a host cell after introduction of a transformation construct containing said first and second DNAs into said host cell.

A further object of the present invention is to provide a transformation construct containing transposing elements combined with a DNA sequence capable of being expressed in a transformed host cell.

A still further object of the present invention is to provide a DNA sequence capable of being expressed in a transformed cell flanked by piggyBac or tagalong terminal inverted repeats.

Another object of the present invention is to provide a method for making a transgenic organism by inserting a transformation construct containing a DNA sequence, capable of being expressed in a transformed cell, flanked by piggyBac or tagalong inverted repeats into a cell; wherein the DNA sequence will excise from the construct and will insert into the host cell at least at the target sequence TTAA in said host cell genome and using the transformed cell to obtain said transgenic organism.

Further objects and advantages of the present invention will become apparent from the following description.

BRIEF DESCRIPTION OF THE DRAWINGS

FIGS. 5a–5e is the entire nucleic acid, SEQ ID NO 11 and amino acid sequence, SEQ ID NO 12, for the piggyBac transposon element.

FIGS. 6a–6g, SEQ ID NO 13 is the entire nucleic acid sequence for the plasmid p3E1.2, also called the p3E1.2 H/S clone. This represents a clone of the Hind/Sal fragment containing the piggyBac insertion from an *Autographa californica* nuclear polyhedrosis virus FP mutant.

FIGS. 7a–7e is the entire nucleic acid sequence, SEQ ID NO 14 for the piggyBac/opd plasmid.

FIGS. 9a–9j is the entire nucleic acid sequence, SEQ ID NO 15 of a pCRII clone of the piggyBac sequence amplified from the p3E1.2 plasmid using the primer MF34.

FIGS. 10a–10h is the entire nucleic acid sequence, SEQ ID NO 16 for plasmid IFP2B/Xpuc18.1.

FIGS. 11a–11h is the entire nucleic acid sequence, SEQ ID NO 17 for plasmid IFP2B/XsupF4H.

FIG. 12a shows the nucleic acid sequence, SEQ ID NO 18 (top) and SEQ ID NO 19 (bottom), of two primers used in the PCR amplification of the hs/opd fragment.

FIGS. 12b–m is the entire nucleic acid sequence, SEQ ID NO 20 of the p3E1.2hs/opd plasmid.

DETAILED DESCRIPTION OF THE INVENTION

Figure 1:
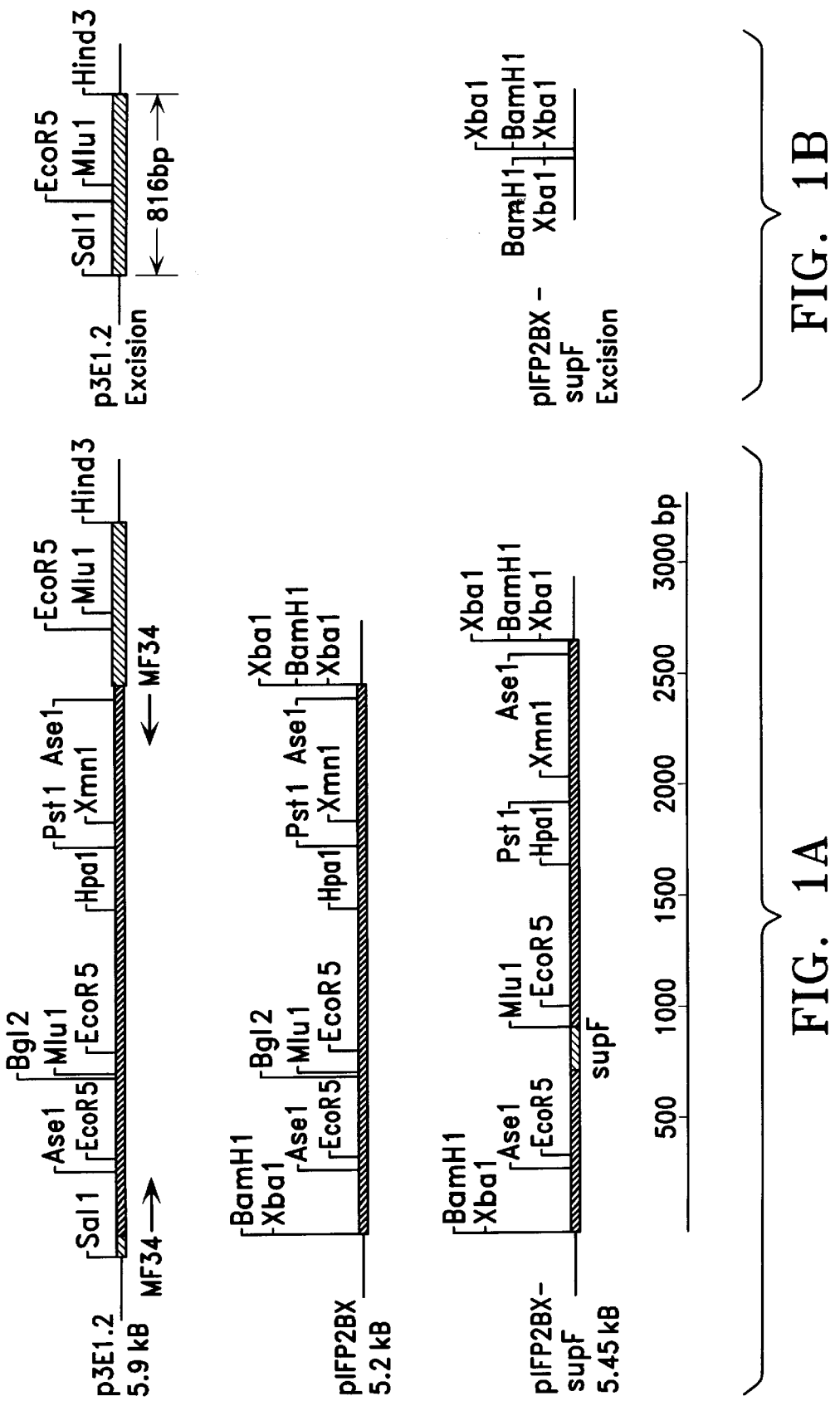
FIG. 1A shows the construction of the pIFP2BX-supF excision donor plasmid. The piggyBac element from p3E1.2 (top) was altered to remove flanking viral sequences (crosshatched bars) by PCR amplification using the primer MF34 (see materials and methods). MF34 anneals to both of the piggybac terminal inverted repeats. The resulting pig-gyBac element (solid black bar) was flanked by TTAA target sites and BamHI/XbaI restriction sites. The 2.5 kB PCR product was cloned into pCRII (Invitrogen). The pCRII-piggyBac clone was digested with BamHI and the 2.5 kB BamHI-piggyBac fragment was subcloned into BamHI-digested pUC18. This clone was designated pIFP2BX (middle). pIFP2BX was digested with BglII (piggyBac nucleotide position 675) and genetically tagged by the addition of a 250 bp BglII fragment containing the supF gene. This plasmid was designated pIFP2BX-supF (bottom) and served as the donor plasmid in excision assays.
FIG. 1B shows that excision of the piggyBac element from either p3E1.2 (top) or pIFP2BX-supF (bottom) produces plasmids with different restriction enzyme profiles at the excision breakpoints. p3E1.2-piggyBac precise excision products are sensitive to digestion with MluI and EcoRV whereas pIFP2BX-supF-piggyBac precise excision products are insensitive to digestion with these same enzymes.

The identification and isolation of autonomous mobile elements from the piggyBac transposon according to the present invention enables the transformation of cells and the production of transgenic organisms wherein DNA capable of being expressed in the transformed cell or transgenic organism is excised from a transformation construct and inserted into the genome of a cell used to produce a transgenic organism. The term cell for the purposes of this invention includes any cell capable of being transformed by the transformation construct of the present invention and preferably includes any eukaryotic cell. More preferably, the cell is any arthropod cell and most preferably the cell is an insect cell. Furthermore, cells are transformed with DNA sequences that are introduced into the cell and targeted for insertion at a TTAA sequence of the cell's DNA. Typically the introduced DNA sequences include functional genes that are flanked by the piggyBac transposon inverted repeats to form a transformation construct. For the purposes of this invention the introduced transformation construct comprises a targeted functional DNA sequence flanked by a pair of transposon terminal inverted repeats from TTAA piggyBac or tagalong transposons. Targeted functional DNA sequence for the purposes of this invention is any heterologous sequence capable of being expressed in a host cell and/or a transgenic organism. In one embodiment of the present invention, the inverted repeats comprise at least 13 bps of the inverted repeats of the piggyBac transposon which include the sequence: left end CCCTAGAAAGATA, SEQ ID NO 2; right end TATCTTTCTAGGG, SEQ ID NO 3. The sequence for a 17 bp inverted repeat is: left end TTAACCCTAGAAAGATA, SEQ ID NO 4; right end TATCTTTCTAGGGTTAA, SEQ ID NO 5. In another embodiment the transformation construct also encodes a transposase gene whose product interacts with the transposon inverted repeats to induce transposition of the targeted sequence. The targeted functional DNA sequence typically will encode a gene that is capable of being expressed in the host cell. This gene can be expressed under the control of an inducible promoter. The targeted DNA can also include a selectable marker gene if the targeted gene to be inserted into the host cell's genome does not itself provide a selectable marker functionality. In one embodiment the transformation construct also can comprise a polylinker flanked by a pair of at least 13 bps of the inverted repeats of the piggyBac transposon. For the purposes of this application, a polylinker is a short length of DNA that contains numerous different endonuclease restrictions sites located in close proximity. The presence of the polylinker is advantageous because it allows various exogenous sequences, such as expression cassettes, to be easily inserted and removed, thus simplifying the process of making a transformation construct containing a particular targeted DNA fragment. When this transformation construct is introduced into a host cell, in the presence of transposase activity specific for the flanking inverted repeats, the targeted DNA sequence will be excised from the introduced construct and will be inserted into a new location. Transposition of the targeted DNA located within the transformation construct is enhanced in the presence of transposase activity. The gene encoding the transposase can either be physically linked to the transformation construct, already present in the host cell's genome, or introduced into the cell as part of a separate DNA molecule. Inducible promoters can be used as a means of triggering the production or transposase activity.

The present invention utilizes the transposon machinery of the TTAA specific transposons to excise and insert the targeted DNA sequence into the genome of the host cell. The resulting transformed cell or group of cells are stable transformants which are then used to make a transgenic organism, using techniques known to the skilled artisan, which will pass the introduced gene to all subsequent progeny.

The above described transformation construct can also be part of a larger construct. The additional sequences of the larger construct comprising DNA sequences capable of replicating the entire DNA molecule in a bacterial host and DNA sequences encoding a bacterial selectable marker such as for example genes encoding for ampicillin or tetracycline resistance. This larger construct, which can be a plasmid, can be used to transform bacterial cells. These transformed bacterial cells can then be cultured to produce large quantities of the plasmid DNA. The plasmid DNA can then be purified and the specific transformation construct can optionally be removed from the DNA sequences utilized to replicate the plasmid in the bacterial cell using techniques well known to those familiar with the art.

In one embodiment of the invention, the target functional DNA sequence encodes a gene operably linked to an inducible promoter. Inducible promoters include any promoter capable of increasing the amount of gene product produced, by a given gene, in response to exposure to an inducer. Thus the use of this construct allows for control of the expression of the target functional gene introduced into the transgenic organism. Inducible promoters are known to those familiar with the art and a variety exists that could be used to drive expression of the transposase gene. Inducible systems include, for example, the heat shock promoter system, the metallothionein system, the glucocorticoid system, tissue specific promoters, etc. Promoters regulated by heat shock, such as the promoter normally associated with the gene encoding the 70-kDa heat shock protein, can increase expression several-fold after exposure to elevated temperatures. The glucocorticoid system also functions well in triggering the expression of genes. The system consists of a gene encoding glucocorticoid receptor protein (GR) which in the presence of a steroid hormone (i.e. glucocorticoid or one of its synthetic equivalents such as dexamethasone) forms a complex with the hormone. This complex then binds to a short nucleotide sequence (26 bp) named the glucocorticoid response element (GRE), and this binding activates the expression of linked genes. Thus inducible promoters can be used as an environmentally inducible promoter for controlling the expression of the introduced gene. Other means besides inducible promoters for controlling the functional activity of a gene product are known to those familiar with the art.

Specifically, the transformation construct of the present invention includes DNA derived from a TTAA specific transposon of the Lepidopteran transposons, piggyBac and tagalong. The piggyBac and tagalong transposons were isolated as insertions in the nuclear polyhedrosis virus,

*Galleria mellonella* (GmMNPV), following maintenance of that virus in the TN-368 cell line, a *T. ni* derived cell line (Fraser et al., *J. Virology*, Volume 47, 287–300, 1983 herein incorporated by reference). Both elements have also been associated with repeated insertion events within the *Autographa californica* NPV (AcMNPV) genome (Cary et al, *Virology*, Volume 172, 156–169, 1989; Kumar & Miller, *Virus Res.*, Volume 7, 335–349, 1987; Wang & Fraser, *J. Insect Mol. Bio.*, Volume 1, 1–7 1992).

The piggyBac (IFP2) element is 2.5 kb in length and is bounded by 13 bp inverted terminal repeats, with additional internal 19 bp inverted repeats located asymmetrically with respect to the ends. The entire nucleic acid, SEQ ID NO 11, and amino acid, SEQ ID NO 12, sequence of the piggyBac element is shown in FIGS. 5a–5e. The internal sequence contains a consensus RNA polymerase II promoter region and a poly-adenylation signal (Cary et al., 1989 supra) flanking a single major open reading frame. The open reading frame encodes a single transcript of approximately 2.1 kb in length with a 5' end that maps to a consensus cap recognition sequence (Cary et al., 1989 supra). This open reading frame encodes transposase activity that enhances the transposition of the piggyBac element.

The tagalong (TFP3) element is considerably smaller (780 bp) with no apparent coding potential (Fraser et al., 1983, 1985 supra; Wang et al., *Gene*, Volume 81, 97–108, 1989; Wang & Fraser, 1992 supra). The element is bounded by 13/15 bp imperfect inverted repeats, and is repeated and dispersed within the genome of all *T. ni* derived cell lines tested. as well as laboratory colonies of *T. ni* (Fraser et al., 1983 supra; Wang et al., 1989 supra; Wang & Fraser, 1992 supra). Comparative sequence analyses of tagalong elements and their insertion sites within baculovirus genomes and host cell genomes Wang & Fraser, 1992 supra) have demonstrated that these elements transpose in an identical fashion whether they are moving in baculovirus-infected cells or in uninfected cells.

Both piggyBac and tagalong elements excise from their insertion sites entirely and in a precise fashion, regenerating a single copy of the TTAA target site at the point of excision. Precise excision of both elements is not restricted to the cell line of origin, TN368, but can also occur in other eukaryotic cells as well.

The creation of a transformed cell requires that the DNA first be physically placed within the host cell. Current transformation procedures utilize a variety of techniques to introduce DNA into a cell. In one form of transformation, the DNA is microinjected directly into cells though the use of micropipettes. Alternatively, high velocity ballistics can be used to propel small DNA associated particles into the cell. In another form, the cell is permeabilized by the presence of polyethylene glycol, thus allowing DNA to enter the cell through diffusion. DNA can also be introduced into a cell by fusing protoplasts with other entities which contain DNA. These entities include minicells, cells, lysosomes or other fusible lipid-surfaced bodies. Electroporation is also an accepted method for introducing DNA into a cell. In this technique, cells are subject to electrical impulses of high field strength which reversibly permeabilizes biomembranes, allowing the entry of exogenous DNA sequences. One preferred method of introducing the transformation construct into cells in accordance with the present invention is to microinject fertilized eggs with the construct. The DNA sequence flanked by the transposon inverted repeats will be inserted into the genome of the fertilized egg during development of the organism, this DNA will be passed on to all of the progeny cells to produce a transgenic organism. The microinjection of eggs to produce transgenic animals has been previously described and utilized to produce transformed mammals and insects (Rubin et al., *Science*, Volume 218,384–393, 1982; Hogan et al., *Manipulating The Mouse Embryo: A Laboratory Manual*, Cold Spring Harbor Laboratory Press, Plainview, N.Y., 1986; Shirk et al., In *Biotechnology For Crop Protection*, Hedin et al (eds.), ACS Books, Washington D.C., 135–146, 1988; Morgan et al., *Annu. Rev.*, Biochem., Volume 62, 191–217, 1993; all herein incorporated by reference). Accordingly transgenic organisms can be produced that have an exogenous DNA sequence that is flanked by the sequence 5' TTAACCC . . . GGGTTAA 3', SEQ ID NO 1 and SEQ ID NO 6 respectively. Accordingly a method of producing stably transformed insects includes the step of microinjecting a transformation construct comprising the inverted repeats of a TTAA specific transposon into a cell, preferably a fertile insect egg. The resulting transgenic insect has an exogenous DNA sequence inserted into its genomic DNA at the sequence TTAA, wherein the inserted exogenous DNA is located between the sequence 5' TTAACCC . . . GGGTTAA 3', SEQ ID NO 1 and SEQ ID NO 6 respectively.

Transformed cells and/or transgenic organisms (those containing the DNA inserted into the host cell's DNA) can be selected from untransformed cells and/or transformed organisms if a selectable marker was included as part of the introduced DNA sequences. Selectable markers include, for example, genes that provide antibiotic, pesticide, insecticide, herbicide resistance; genes that modify the physiology of the host, such as for example eye color or green fluorescent protein, to produce an altered visible phenotype; etc. Cells and/or organisms containing these genes are capable of surviving in the presence of antibiotic, insecticides or herbicide concentrations that kill untransformed cells/organisms or producing an altered visible phenotype. Using standard techniques known to those familiar with the field, techniques such as, for example, Southern blotting and polymerase chain reaction, DNA can be isolated from transgenic cells and/or organisms to confirm that the introduced DNA has been inserted.

Specifically, the TTAA specific transposon based constructs of the present invention are utilized in a method to genetically transform insects. The method comprises the steps of introducing the construct into the egg of the organism wherein the transposon excises from the plasmid and is inserted into the genome of the host. A piggyBac derived construct has been used to transform the cabbage looper moth. The construct was microinjected into eggs at a preblastula stage and the piggyBac DNA was induced to move from the plasmid DNA to stably integrate into the chromosomal DNA of germ cells of the cabbage looper moth. Thus, the piggyBac transposon is useful as a vector to move foreign genes into cabbage looper moth chromosomes and, as a consequence, produce genetically transformed insects. The piggyBac transposon genetic transformation system provides a broad spectrum method that does not currently exist for the introduction of foreign genes into insects.

Genetic modification of insects with new genetic elements provides a means to control populations of agriculturally pestiferous or beneficial insects. The ability to control pest insects through genetically based sterile insect programs or genetically introduced targeted conditional suseptibilities will result in significant cost savings to agribusiness. In addition, introduction of genes that impart resistance to chemicals (including herbicides, pesticides and insecticides) can improve the efficacy of beneficial insects. This technology can also be used for detection and monitoring of insect populations and infestations where the piggyBac transposon is present in the population. Each of these applications will result in more efficient pest control programs.

Enhancing the resistance of beneficial insects to to pesticides will enhance the efficacy of the beneficial insects and may allow for the simultaneous use of chemical control and biological control of pests. Some of the beneficial insects that would make good candidates for such transformations include *Hymenopteran parasitoids* of Heliothis spp: *Microplitis croceips* and *Cardiochiles nigriceps; Hymenopteran parasitoid* of Diamondback moth, *Plutella xylostella: Diadegma insolare; Hymenopteran parasitoid* of the Indianmeal moth, *Plodia interpunctella: Bracon hebitor*; and Hemipteran predators: *Xylocoris flavipes* and *Podisus maculatus*.

The following examples are intended only to further the invention and are not intended to limit the scope of the invention as described by the claims.

EXAMPLE 1

The piggyBac-deficient *Spodoptera frugiperda* cell line, IPLB-SF21AE (Vaughn et al., *In Vitro*, Volume 13, 213–217, 1977 herein incorporated by reference) was maintained as described in Fraser, Smith & Summers, *J. Virol.* 47: p. 287–300, 1983; herein incorporated by reference. Twenty-four hours prior to use, cells were seeded to early-log phase to insure optimum growth at transfection.

EXAMPLE 2

Figure 2:
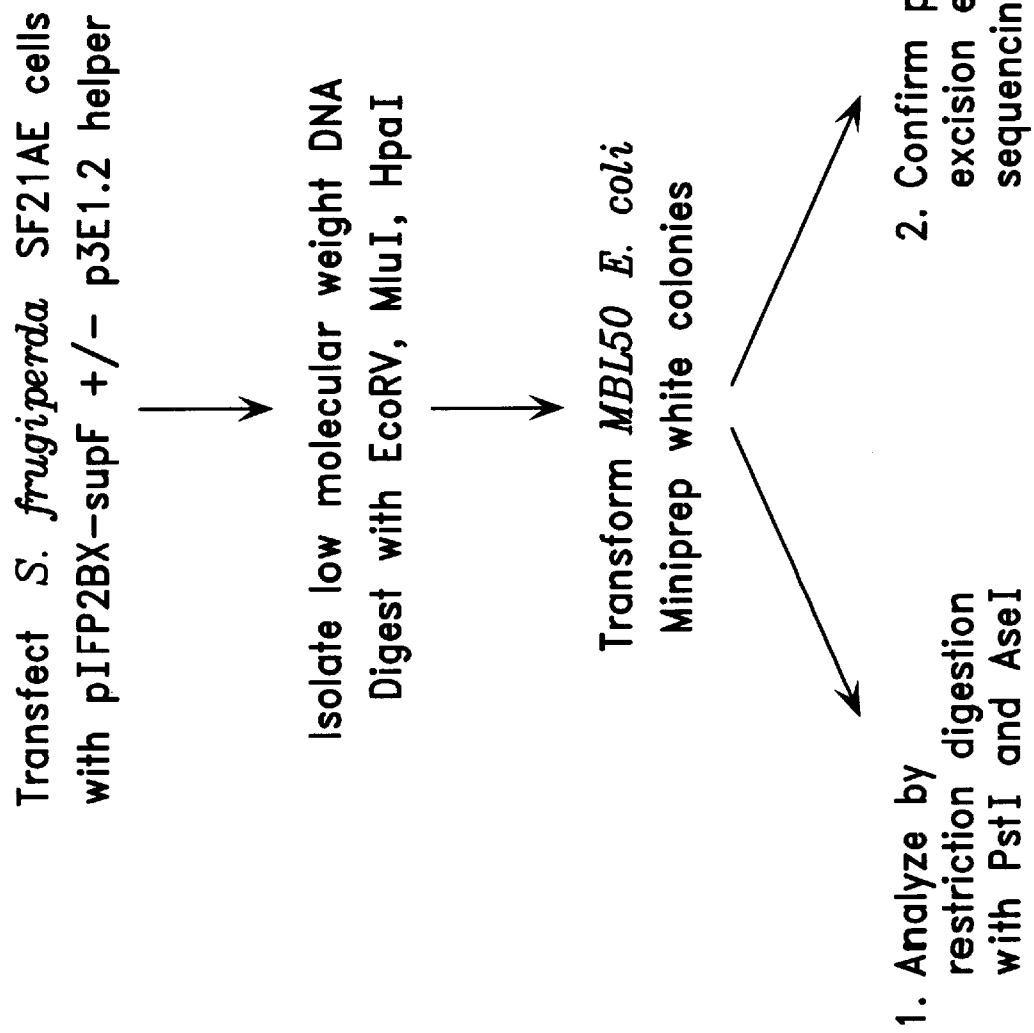
FIG. 2 shows the experimental strategy for analysis of piggyBac excision from the donor plasmid pIFP2BX-supF. *S. frugiperda* cells were transfected with donor DNA in the presence or absence of the helper transposon p3E1.2. Low molecular weight DNA was isolated at 48 hours post transfection and digested with the restriction enzymes EcoRV, MluI, and HpaI to select against non-excised piggyBac plasmids and the p3E1.2 helper plasmid. The digested DNA was used to transform MBL50 *E. coli*. White colonies containing plasmids that were not digested by the enzyme mix were analyzed by restriction digestion with PstI and AseI (FIG. 3) to determine if they resulted from piggyBac excision. Putative excision clones were then sequenced to confirm the sequence at the excision breakpoints (FIGS. 4A and 4B).

In order to clone plasmid excision contructs, plasmid p3E1.2 (FIGS. 6a–6g), containing an active piggyBac element, was used as a template for PCR reactions with the inverted terminal repeat-specific BamHI/XbaI-ended primer MF34 to remove flanking viral sequences from p3E1.2 (FIGS. 2 and 6, SEQ ID NO 13). A primer oligonucleotide, MF34, having the sequence 5' GGATCCTCTAGATTAAC-CCTAGAAAGATA 3', SEQ ID NO 7, annealed to both piggyBac terminal repeats and generated a full-length piggyBac transposon product. The MF34 primer is tailed with BamHI and XbaI sites immediately adjacent to the TTAA target site and terminal inverted repeat sequences. This single primer amplified the entire piggyBac element and target site duplication because of its homology to both ends of the element through the terminal repeat sequences. The PCR reaction contained approximately 5 Units Taq polymerase (Promega), about 2 mM $MgCl_2$, about 1 mM dNTPs, about 50 mM KCl, about 10 mM Tris-Cl pH 9, 0.1% Triton X, and about 100 pmols MF34 primer. The 2.5 kB amplified BamHI/XbaI-ended piggyBac PCR product is tailed with BamHI and XbaI sites flanking the TTAA target sites on both sides, and was cloned into pCRII (Invitrogen) TA cloning vector (FIGS. 9a–9j, SEQ ID NO 15) to generate a piggyBac element flanked by TTAA target sights and BamHI/XbaI restriction sites (Elick et al, *Genetica*, Volume 98, 33–41, 1996; herein incorporated by reference in its entirety). This is analyzed extensively by restriction digestion to insure the PCR product did not contain significant mutations due to infidelity of the Taq polymerase. An approximately 2.5 kB BamHI fragment was then subcloned into pUC18 and designated pIFP2BX (FIGS. 1A and 10a–10h, SEQ ID NO 16). Both orientations of the BamHI insert are cloned. About a 250 bp BamHI fragment containing the *E. coli* tRNA suppresser gene, supF (Ariza et al., 1993), was band-isolated from pKFsupF (kindly supplied by Dr. D. O'Brochta) and cloned into the unique BglII site of pIFP2BX by interrupting the open reading frame at the unique BglII site (nucleotide position 673 and adding a BglII-compatible 250 bp BamHI cartridge containing the suupF gene (FIGS. 1a and 11a–11h, SEQ ID NO 17) (Elick et al, *Genetica*, Volume 98, 33–41, 1996; herein incorporated by reference). This plasmid was designated piFp2BX-supF (FIGS. 1A and 11a–11h, SEQ ID NO 17) and was the donor plasmid in excision assays.

The supF gene encodes a tRNA (Ariza. et al., *Carcinogenesis*, Volume 14, 303–305, 1993; herein incorporated by reference) that suppressed an amber mutation in the 9-galactosidase gene of the *E. coli* strain MBL50 to produce blue colonies in the presence of X-gal. If the piggyBac element tagged with the supF gene is excised from tne plasmid pIFP2BX-supF, the amber mutation in the MBL50 B-galactbsidase gene was not suppressed and the resulting colonies were white in the presence of Xgal.

EXAMPLE 3

The $CaPO_4$ co-precipitation protocol was used to cotransfect plasmid excision vectors into piggyBac-deficient IPLB-SF21AE cells (Corsaro & Fraser, *J. Tiss. Cul. Meth.*, Volume 12, 7–12, 1989; Graham & Van der Eb, *Virology*, Volume 52, 456–467, 1973; Summers & Smith, *A Manual of methods for baculoviurs vectors and insect cell culture procedures*, Texas Agricultural Experiment Station Bulletin, 1987; all herein incorporated by reference). The IPLB-SF21AE cell line is used because this cell line lacks piggyBac-homologous sequences (Cary et al., 1989 supra; Elick et al., *Genetica*, Volume 97, 127–139, 1996; herein incorporated by reference). It was expected that co-transfection of the pIFP2BX-supF plasmid with the helper plasmid p3E1.2 would increase the number of white excision products if excision of piggyBac was enhanced by the presence of the presumptive transposase. About 5 µg of supercoiled pIFP2BX-supF donor plasmid DNA was combined with about 5 µg of supercoiled p3E1.2 helper plasmid in about 1 ml 1x Hepes, pH about 7.1. Transfections done in the absence of the helper plasmid contained twice as much (approximately 10 µg) donor plasmid DNA. After incubation the co-transfection mixtures were placed onto monolayers of IPLB-SF21AE cells and incubated for one hour with gentle agitation approximately every 15 minutes. The monolayers were then fed with about 1 ml TNM-FH +approximately 8% FBS and incubated for about another 4 hours at 27° C. Transfected cells were harvested approximately 48 hours post transfection for extraction of plasmid DNA.

EXAMPLE 4

Low molecular weight DNA, i.e., extrachromosomal DNA, was isolated from transfected cells of Example 3 according to the method of Hirt (Hirt, *J. Mol. Bio.*, Volume 26, 365–369, 1967; herein incorporated by reference). The media was removed from the cells and approximately 800 µl of Hirt extraction buffer (about 25 mM Tris-Cl, about 10 mM EDTA, about 0.6% SDS, pH about 7.5) was added. Cell lysates were scraped into microcentrifuge tubes after about 5 minutes and NaCl was added to a final concentration of about 1M. The lysates were incubated on ice for about 2 hours and centrifuged for about 15 minutes at about 15K and about 4° C. Supernatants containing low molecular weight DNA were placed into fresh tubes, extracted with phenol/chloroform and precipitated with ethanol according to standard protocols (Sambrook, Fritsch & Maniatis, *Molecular Cloning, A Laboratory Manual*, Cold Spring Harbor Press, 1989; herein incorporated by reference). The extracted DNA was resuspended in water and used in restriction digestions and electrotransformations of MBL50 *E. coli.*

EXAMPLE 5

The Hirt isolated DNAs from Example 4 were digested with approximately 5' U each of MluI, EcoRV, and HpaI (Promega) in approximately 100 µl reactions containing approximately 1 µg DNA. Each of these enzymes act within the piggyBac element. These reactions were carried out as recommended by the manufacturer. The loss of piggyBac from pIFP2BX-supF prevented digestion with this enzyme mix (see FIG. 1B). The loss of piggyBac from the helper plasmid p3E1.2 did not prevent digestion with EcoRV or MluI (see FIG. 1B). The p3E1.2 plasmids as well as any plasmids resulting from excision of piggyBac from p3E1.2 were selectively degraded.

The MBL50 *E. coli* strain was transformed with approximately 10 µg of Hirt isolated, digested DNA using a Bio-Rad Gene Pulser. Briefly, approximately 40 µls of electrocompetent MBL50 *E. coil* were combined with the digested DNA on ice, placed into an approximately 0.2 cm gap electroporation cuvette and pulsed at settings of about 25 µFd, about 25 kV, about 200 ΩA, about 1.5 ml aliquot of SOC (about 2% w/v bacto-tryptone, about 0.5% w/v bacto-yeast extract, about 8.5 mM NaCl, about 2.5 mM KCl, about 10 MM $MgCl_2$, about 20 mM glucose) was added after electroporation. The electroporated bacteria were collected immediately by centrifugation at about 2000×g for about 5 minutes at room temperature, resuspended in about 100 µls SOC and spread on LB plates (about 150×15 mm) containing approximately 100 µls of about 2% X-gal and approximately 50 µg/ml ampicillin.

Figure 3:
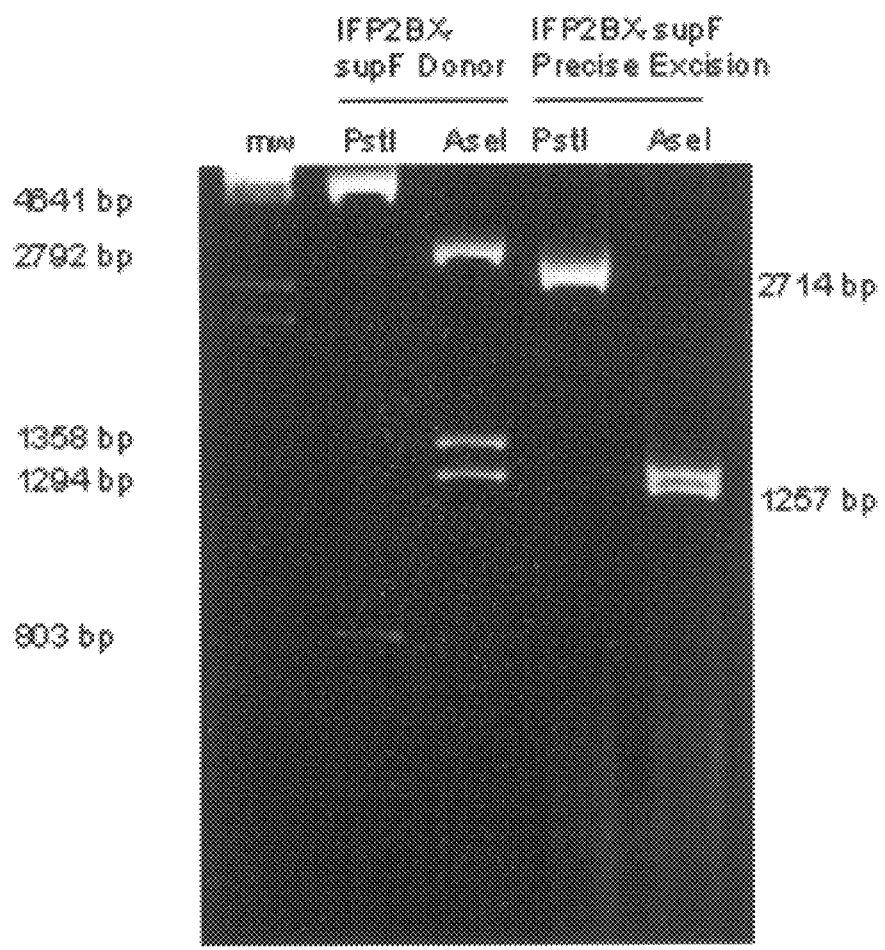
FIG. 3 is a photograph of a gel showing restriction enzyme analysis of a representative piggyBac excision clone and a non-excised plasmid clone. Digestion of the pIFP2BX-supF donor plasmid with PstI generates two products of 4641 bp and 803 bp. Digestion of pIFP2BX-supF with AseI generates three products of 2792, 1358, and 1294 bp. If piggyBac excises precisely from this plasmid, a single product of 2714 bp is produced from PstI digestion and a diagnostic 1257 bp product is produced from AseI digestion due to creation of a new ATTAAT AseI site at the point of excision (see sequence, FIG. 4). Another diagnostic AseI band of 163 bp is not resolved on this gel but is resolved on overloaded 2.5% agarose gels (not shown).
Figure 4A:
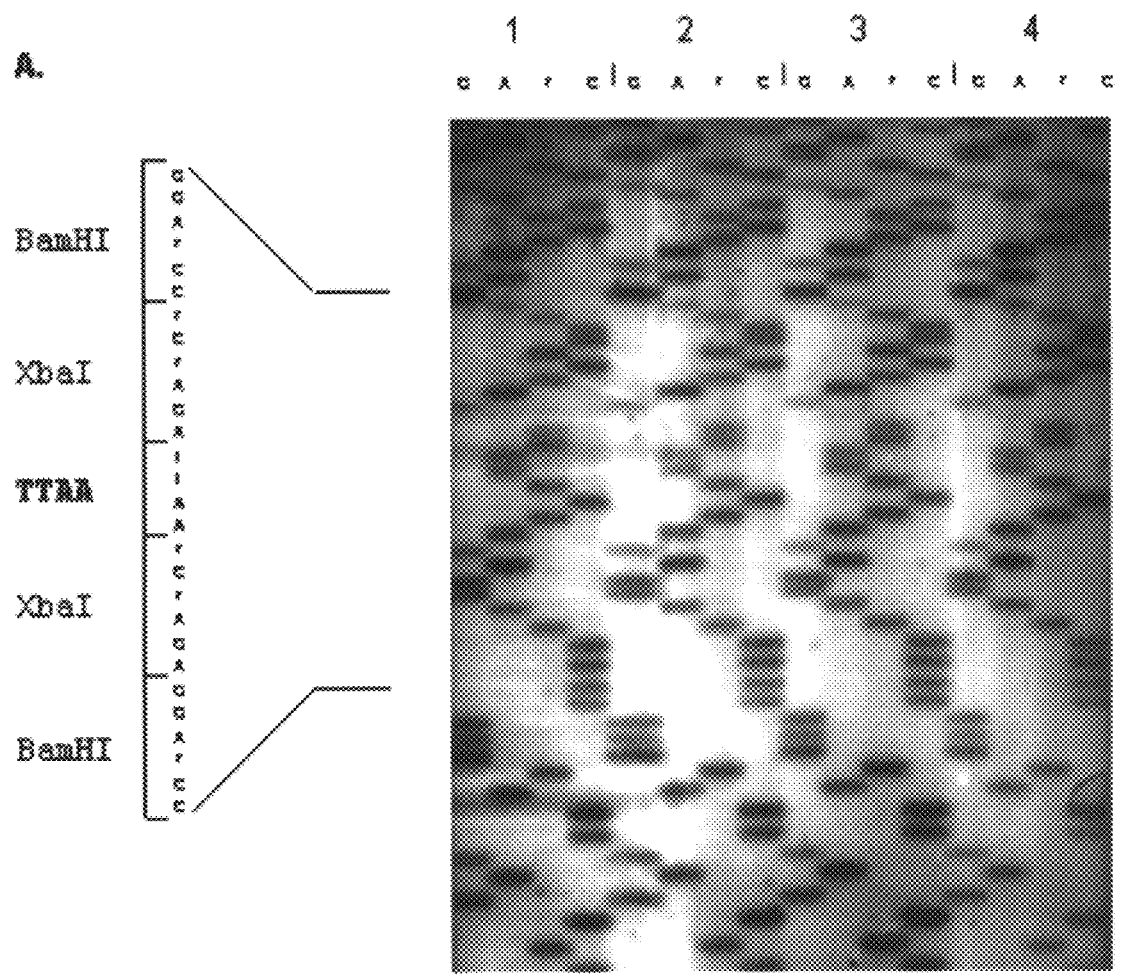
FIG. 4A is a photograph of a gel showing dideoxy sequencing analysis of four representative piggyBac excisions from pIFP2BX-supF.

The pIFP2BX-supF plasmid contains two PstI sites, one in the piggyBac element and the other in the multiple cloning site of pUC18. Digestion of pIFP2BX-supF with PstI generates two fragments of 4641 bp and 803 bp in length (FIG. 3). Excision of the—2750 bp piggyBac element from this plasmid removes one of the PstI sites to generate a single PstI digestion product of 2714 bp. The supF(−) clones exhibiting this single 2714 bp PstI product were then analyzed with AseI. This enzyme recognizes the sequence ATTAAT. Precise excision of piggyBac from pIFP2BX-supF regenerates a single TTAA and a new AseI site is generated at the excision breakpoint. A diagnostic Ase I band of 1257 bp is resolved on a 2.5% agarose gel (FIG. 3). The other diagnostic AseI fragment of 163 bp is also resolved on a 2.5% gel when the gel is overloaded (data not shown). In addition, the donor pIFP2BX-supF AseI fragments of 2792 bp and 1358 bp are absent in clones where piggyBac has excised (FIG. 3). After screening by restriction digestion, positive clones were sequenced to confirm the precise excision events that had generated the sequence GGATCCTCTAG(ATTAACT)CTAGAGGATCC, SEQ ID NO 8 at the excision breakpoints (FIGS. 4*a* and *b*).

Digested Hirt extracts harvested from cells transfected with 10 µg of pIFP2BX-supF alone (control) generated a total of 51 white colonies in three separate experiments upon transformation of MBL50 cells. No precise excisions of the SupF-tagged piggyBac element were recovered in the absence of the piggyBac transposase (Table 1). Table 1 shows assay results for supF(−) plasmids obtained from transformation of *E. coli* MBL50 cells either prior to or following transfection of the IPLB-SF21AE insect cell line. The IPLB-SF21AE (SF21AE) cell line was transfected with the pIFP2BX-supF plasmid (psupF) in the absence or presence of the p3E1.2 helper plasmid. At 48 hours post transfection a Hirt extraction was performed to isolate plasmid DNAs. Equivalent amounts of Hirt extracted DNAs were transformed either directly (Total Number of Plasmids) or following treatment with the restriction enzyme mix EcoRV, MluI, and EcoRV (Number supF(−)) into *E. coli* MBL50 cells and the number of colonies produced was counted. In the control experiment (MBL50) equivalent aliquots of either undigested or pre-digested pIFP2BX-supF plasmid DNA were transformed directly into the bacteria (Total Number of Plasmids and Number supF(−), respectively). The number of and percentage of precise excision events among the white supF(−) plasmids recovered was determined (Number Precise and Percent Precise, respectively) and the frequency of precise excisions was calculated relative to the total number of supF(−) plasmids recovered. In these instances the loss of supF activity apparently resulted from random deletions of supF, piggybac, and/or portions of the pUC18 plasmid DNA.

Transfections of IPLB-SF21AE cells with pIFP2BX-supF in the presence of the p3E1.2 helper transposon also produced plasmids that resisted digestion with the enzyme mix and generated white colonies upon transformation of MBL50 *E. coli*. A total of 19 supF negative clones isolated from 3 independent experiments were analyzed by restriction digestion.

TABLE 1

| 11s | Plasmids | Total Number of Plasmids | Number supF(−) | Number Precise | Percent Precise | Frequency |
|---|---|---|---|---|---|---|
| 21AE | pIFP2BX-supF | 1 × 10(7) | 51 | 0 | 0 | 0 |
| 21AE | pIFP2BX-supF + 3E1.2 | 1 × 10(5) | 19 | 11 | 58 | 1 × 10(−4) |
| L50 | pIFP2BX-supF | 3 × 10(5) | 25 | 0 | 0 | 0 |

EXAMPLE 6

White colonies resulting from the supF deletions in Example 5, representing putative excision events, were mini-prepped by boiling according to standard protocols (Sambrook et al., 1989 supra) and analyzed by restriction digestion and sequencing. The plasmid DNAs were digested with PstI to identify possible excision events (FIG. 3). PstI digests positive for excision were further characterized by digestion with the enzyme AseI (FIG. 3) since precise excision of piggyBac from pIFP2BX-supF generates a new AseI site (ATTAAT, SEQ ID NO 9) at the excision breakpoint. Double-stranded DNAs from clones representing putative excision events were sequenced by the dideoxy method (Sanger, Nicklen & Coulson, *PNAS USA*, Volume 74, 5463–5467, 1977 herein incorporated by reference) using the Sequenase version 2.0 kit (Amersham).

Figure 4B:
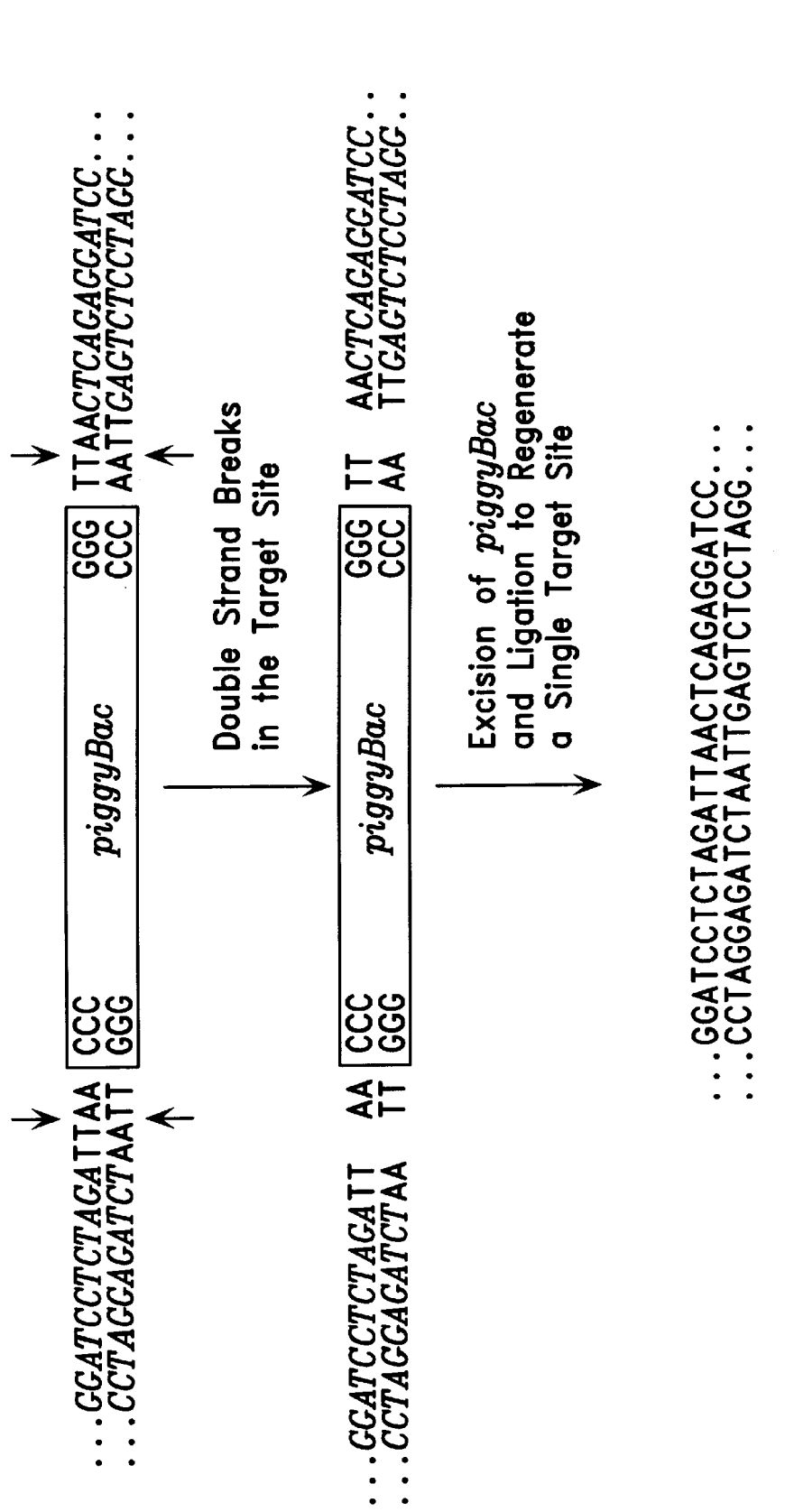
FIG. 4B shows that precise excision of piggyBac from the pIFp2BX-supF donor plasmid generates the characteristic BamHI/XbaI-TTAA-XbaI/BamHI nucleotide sequence SEQ ID NO 21 and SEQ ID NO 22.

Eleven of these clones appeared to be precise piggyBac excision events. The remaining 8 white clones were not characterized further since they reflected extreme deletions or rearrangements that appeared to be unrelated to piggyBac excision. The eleven putative excision clones were sequenced and all were confirmed as precise excision events (Table 1), leaving a single TTAA at the excision breakpoint (FIG. 4).

Overall, 58% percent of the white colonies screened from co-transfections with pIFP2BX-supF and p3E1.2 were derived from precise piggyBac excision events. In contrast, 0% of the recovered plasmids exhibited precise excisions when the helper plasmid was not supplied (Table 1). These results demonstrated that precise excision of piggyBac from plasmids in IPLB-SF21AE cells was significantly enhanced by the addition of the p3E1.2 helper transposon plasmid.

EXAMPLE 7

To estimate the frequencies of supF(−) plasmids resulting from precise excision of piggyBac versus those resulting from alternative deletions, equal amounts of Hirt extracted DNAs from transfected IPLB-SF21AE cells were either mock digested or digested with MluI, EcORV, and HpaI in 100 $\mu$l reactions. Equal amounts of these DNAs were then transformed into MBL50 E. coli. The supF deletion frequency was calculated as the number of white colonies produced from the digested preparation divided by the total number of colonies produced from the undigested control.

The frequency of supF deletions that were unrelated to precise piggyBac excision in control transfections with pIFP2BX-supF alone was determined. In the absence of the p3E1.2 helper transposon, a white colony was generated in every $2\times10^4$ pIFP2BX-supF plasmids used to transform MBL50 E. coli. This equals a background supF deletion frequency of $5\times10^{-5}$ (Table 1).

In the presence of the p3E1.2 helper transposon, approximately one white colony was generated in every $5.8\times10^3$ input plasmids (both pIFP2BX-supF and p3E1.2) and one precise excision was confirmed in every $1.2\times10^4$ input plasmids. This corresponds to a supF deletion frequency of $1.8\times10^{-4}$ and a piggyBac precise excision frequency of $1.0\times10^{-4}$ (Table 1).

The possibility existed that that the piggyBac-supF excision events could have occurred in MBL50 E. coli after transformation with the Hirt extracted DNAs rather than in the transfected IPLB-SF21AE cells. As a control, we performed direct transformations of MBL50 E. coli with pIFP2BX-SupF DNA pre-digested with MluI, EcoRV, and HpaI. The transformation mixtures were spread on LB-amp+ X-gal plates and plasmids from white colonies were screened by restriction digestion with several diagnostic enzymes. A total of 25 white colonies were generated in three separate experiments from these direct transformations. None of these white colonies resulted from plasmids with precise excisions of the supF-tagged piggyBac elment. These results confirmed that the precise excisions of piggyBac must have occurred exclusively in IPLBSF21AE cells and not in transformed bacteria.

The frequency of the imprecise spontaneous supF deletions from plasmids directly transformed into the NBL50 E. coli cells was compared to the previously calculated frequency from Hirt extracted plasmids recovered from transfected IPLB-SF21AE cells to determine if the observed background SupF deletion events occurred predominantly in the SF21AE cells or in the bacteria. In three separate transformations, the MBL50 E. coli directly transformed with $3\times10^5$ digested pIFP2BX-supF plasmids generated a total of 25 white colonies (Table 1). This corresponded to a supF deletion frequency of $8\times10^{-5}$. This frequency was similar to the supF deletion frequency previously observed for pIFP2BX-supF plasmids that had been introduced into IPLBSF21AE cells in the absence of the helper p3E1.2 ($5\times10^{-5}$). This apparent similarity in supF deletion frequencies suggested the majority of background supF deletion events (those not involving a precise piggyBac excision) had occurred in the transformed bacteria and not in the transfected IPLB-SF21AE cells. Further evidence for this conclusion was apparent from the similarities of restriction fragment patterns among those clones isolated following direct bacterial transformations and those isolated following transfections of IPLB-SF21AE cells (data not shown).

The above establishes that precise excision of piggyBac is enhanced by the addition of the helper p3E1.2 in transfected IPLB-SF21AE cells. This helper plasmid presumably provides a source of the piggyBac transposase. Precise excisions of genetically tagged piggyBac from mutant Baculovirus genomes have been observed in infected IPLB-SF21AE cells in the absence of a helper transposon (data not shown). Precise excisions in transfected IPLB-SF21AE cells in the absence of the helper transposase was not detected. However, precise excisions probably do occur at some baseline frequency.

The inability to find precise excisions in this plasmid assay in the absence of added transposase plasmid is probably the result of an excision frequency that is slightly below the detection limit. Precise excisions from the Baculovirus recombinants results in viruses that are then amplified in the infected cells, and the ability to detect these relatively infrequent excision events is therefore enhanced. The results of the plasmid-based excision assay also confirm that viral-encoded gene products are not necessary for precise excision of piggyBac in these Lepidopteran cells.

The frequent and favored event of piggyBac precise excision is unique among Class II transposons. In the case of the hobo element of *Drosophila melanogaster*, excision from plasmids in microinjected fertile eggs most often involves the complete removal of hobo and some flanking nucleotides with the addition of filler sequences related to flanking host DNA at the excision breakpoints (Atkinson, Warren & O'Brochta, 1993 supra; Handler & Gomez, *Mol. Gen. Genet.*, Volume 247, 399–408, 1995; O'Brochta & Handler, 1993 supra; all herein incorporated by reference). This addition of filler sequence could involve either a polymerase-dependent template-switching process during repair of the excision breakpoint (Saedler & Nevers, *J. Eur. Mol. Bio. Org.*, Volume 4, 585–590, 1985; herein incorporated by reference) or the formation of hairpins at the excision breakpoint that are subsequently nicked, filled in, and religated (Takasu Ishikawa, Ishihara & Hotta, *Mol. Gen. Genet.*, Volume 232, 17–23, 1992; Coen & Carpenter, *J. Eur. Mol. Bio. Org.*, Volume 7, 877–883, 1988). The hobo excision process requires the hobo transposase or may involve cross mobilization by a similar transposase with hobo-like activity (Atkinson, Warren & O'Brochta, 1993 supra; Handler & Gomez, 1995 supra; O'Brochta et al., 1994 supra; Warren, Atkinson & O'Brochta, *Genet. Res.*, Volume 64, 87–97, 1994). The piggyBac element may also be cross mobilized in the absence of added piggyBac transposase by similar elements resident in the IPLB-SF21AE cell line (Fraser et al., *Virology* 211, p397–407 1995; herein incorporated by reference). The piggyBac element most often excises precisely from plasmids in IPLB-SF21AE cells when supplied with a piggyBac transposase source. piggyBac also preferentially excises precisely from Baculoviruses in infected IPLB-SF21AE cells (data not shown). No extra nucleotides are removed and no filler sequences are inserted at the piggyBac excision breakpoints.

Like piggyBac, the P element can excise precisely from plasmids in vitro in the presence of transposase (Rio, Laski & Rubin, *Cell*, Volume 44, 21–32, 1986). However, the P element most often excises imprecisely in vivo, leaving behind residual terminal repeat sequences at the excision breakpoints (O'Brochta, Gomez & Handler, 1991 supra; Takasu-Ishikawa, Ishihara & Hotta, 1992 supra). The apparent precise excision events of genomic P elements in vivo are due to homolog dependent gap repair rather than precise excision (Engels et al., *Cell*, Volume 62, 15–525, 1990). Since there are no ectopic repair templates representing piggyBac empty sites in either plasmid-based assays or in Baculovirus infected cells, piggyBac precise excision is most likely coupled to the cleavage process itself rather than being a consequence of a subsequent repair event.

The IPLB-SF21AE cell line, derived from *S. frugiperda*, was established in the mid 1970's (Vaughn et al., *In Vitro*, Volume 13, 17–23, 1977; herein incorporated by reference) and is devoid of piggyBac homologous sequences, yet piggyBac is capable of excising in IPLB-SF21AE cells when supplied with piggyBac transposase. A previous report (Fraser et al., 1995 supra) had established that piggyBac is also capable of transposing in these cells. Since the excision process in IPLB-SF21AE cells apparently reflects the ability of piggyBac to transpose in these cells (Fraser et al., 1995 supra), an excision assay for piggyBac is useful in determining the ability of piggyBac to mobilize in other species as well. tagalong (formerly TFP3), another TTAA specific transposable element, is also capable of precise excision in IPLB-SF21AE cells (Fraser et al., 1995 supra). tagalong has a smaller DNA sequence than piggyBac and has no apparent coding potential (Fraser, Smith & Summmers, J. Virology, Volume 47, 287–300, 1983; Wang & Fraser, 1992 supra; Wang, Fraser & Cary, 1989 supra). Like piggyBac, tagalong was originally isolated as an insertion into the Baculovirus genome after passage of the virus in TN-368 cells (Wang & Fraser, 1992 supra).

The extreme specificity for TTAA target sites upon insertion of piggyBac also occurs in uninfected TN-368 cells (Elick et al., 1995 supra) eliminating any possible involvement of virus-specified proteins in the target selection and insertion process. piggyBac contains a single ORF that, when interrupted, abolishes the ability of the element to transpose (Fraser et al., 1995 supra).

The specificity for TTAA target sites is exhibited by other Lepidopteran transposon-like insertions as well (Beames & Summers, *Virology* 162, 206–220, 1988; Beames & Summers, *Virology*, Volume 174, 354–363, 1990; Carstens, Virology, Volume 161, 8–17, 1987; Oellig et al., *J. Virology*, Volume 61, 3048–3057, 1987; Schetter, Oellig & Doerfler, *J. Virology*, Volume 64, 1844–1850, 1990). In addition to TTAA target specificity, all of these Lepidopteran insertions terminate in at least two C residues at the 5' ends of their inverted repeats. Given their similarity in insertion site selection and duplication, these TTAA specific elements are likely to excise in a similar manner.

The ability of a piggyBac derived construct carrying an exogenous gene as the targeted sequence to transpose in vivo has been demonstrated using a Baculovirus genome as the DNA targeted for insertion (Fraser et al., 1995 supra). This transposition assay demonstrates that a Lepidopteran transposon is capable of transposing while carrying a marker gene in insect cells.

Following the transposition assay the ability of piggyBac or tagalong inserted elements to excise from the Baculovirus genome was examined. Recovery of excision events relied on the blue/white screening of polh/lacZ tagged tagalong or piggyBac insertions. In contrast with tagalong, none of the white revertants we analyzed from piggyBac excision events resulted from mutation of the polh/lacZ gene. The complete lack of alternative mutations leading to the white revertant plaque phenotype demonstrates that the rate of precise excision for piggyBac exceeds the baseline mutation rate in these infected cells. tagalong and piggyBac elements do not necessarily require their own transposon-encoded functions for precise excision in baculovirus-infected cells. tagalong excision was effected in both TN-368 cells having resident copies of this element and in SF21AE cells lacking tagalong homologues. Similarly, the piggyBac element excised repeatedly and precisely in SF21AE cells lacking piggyBac homologues. Since there are transpositionally active TTAA-specific elements resident in the SF21AE cell line (Carstens, 1987 supra; Beames & Summers, 1988, 1990 supra) excision of piggyBac in these cells could reflect the cross-mobilizing activity of some resident TTAA-specific element.

True precise excision is often a site-specific recombination event involving enzymes that recognize specific sequences or structures at or near the termini of the element (for reviews see Sadowski, *J. Biol. Chem.*, Volume 267, 21273–21276,1993; Plasterk, FASEB, Volume 7, 760–767, 1993. Mizuuchi, *Cell*, Volume 74, 781–786, 1992). Comparisons between the terminal inverted repeat domains of tagalong and piggyBac, or between these elements and other TTAA specific elements reveal few similarities aside from the target site and three terminal bases, 5' TTAACCC . . . GGGTTAA 3', SEQ ID NO 7 and SEQ ID NO 6, respectively.

EXAMPLE 8

The feasibility of the microinjection procedure has been established for *T. ni, S. frugiperda, S. exigua, H. zea*, and *P. interpunctella* embryos, yielding survival rates of 70% or better. A major advantage of the lepidopteran egg development is the relatively extended time from egg laying to blastoderm development (Nagy et al., *Dev. Biol.*, Volume 165, 137–151, 1994). For *T. ni* this period seems to be about 6–8 hours. The amount of DNA injected and the lengthy period before blastoderm formation allows germ line nuclei to become transformed in at least some of thefertile eggs.

The microinjection protocol utilizes approximately two to six hr old *T. ni* eggs. The eggs are attached to a microscope cover slip with double-stick tape without dechorionation. Approximately 2 ml of PBS (about 5 mM Kcl, about 100 mM NaH2PO4, pH about 6.8) containing approximately 100 ug/ml of plasmid DNA is injected directly into each egg. The perforation in the egg resulting from the needle is sealed with a coating of Krazy Glue. The eggs are then maintained at about 22° C. and about 80% relative humidity for approximately twelve hours with a normal photocycle of about 16hr:8hr (light:dark) before being placed on diet.

EXAMPLE 9

Evidence indicates that the piggyBac element transposes through a cut-and-paste mechanism. Thus excision of the element is necessary for transposition. Therefore, excision assays with piggyBac in lepidopteran embryos should be an effective predictor of its ability to transpose in that species. This assay has been used with other transposons and is accepted as an effective predictor of the ability of an element to transpose in a given species (Handler, A. M. and Gomez, S. P. (1995), The hobo transposable element has transposase dependent and -independent excision activity in drosophilid species, *Mol. Gen. Genet.* 247, 399–408; O'Brochta, D. A., Handler, A. M. (1988), Mobility of P-elements in drosophilids and nondrosophilids. *Proc. Natl. Acad. Sci. (USA)* 85, 6052–6056; all herein incorporated by reference.) Using a supF-tagged piggyBac element (pIFP2BX-supF, FIG. 2), microinjections were performed on *T. ni, S. frugiperda, S. exigua*, and *H. zea* embryos. Precise excision events characteristic of piggyBac mobilization were observed in all species examined. Surprisingly, these events occurred even in the absence of added helper p3E1.2 plasmid, suggesting the presence of transmobilizing elements in these species. Note there is no possibility for homolog dependent gap repair or homologous exchange with these plasmid constructs, since there are no wild type copies of piggyBac in the cell line used in these studies. The background precise excision suggests there are active cross-mobilizing elements already present in these species. Because excision is a prerequisite for transposition in a cut-and-paste mechanism (see above), the fact that excision occurs is predictive that transposition in these species is possible.

EXAMPLE 10

Precise excisions of the tagged piggyBac transposon from the IFP2BX-supF 4H plasmid were recovered following microinjection of fertile insect eggs by Hirt extraction and transformation of MBL50 *E. coli. S. exigua, H. virescens, P. interpunctella, T. ni, S. frugiperda, A. aegypti* and *D. melanogaster* fertile insect eggs were injected as described above. Some injections were done with added helper p3E1.2 plasmed while others were done without the helper plasmid. The results are shown below in Table 2. The characteristic precise excision event associated with mobilization of the piggyBac element was recovered from most of the microinjected insects whether or not helper was added. The inability to recover precise excision events in a couple of species is likely due to a low number of total number of supF(-) plasmids available for analysis. These experiments establish that the characteristic precise excision of piggyBac associated with the transposition event is possible in a wide range of insect species spanning the orders Lepidoptera and Diptera. These results verify that piggyBac may be used for transformation of a wide range of insects.

TABLE 2

| Organism | Number supF (-) | Precise Excisions | Near Terminal Excisions |
|---|---|---|---|
| *S. exigua* – helper | 14 | 1 | 2 |
| H. virescens – helper | 4 | 1 | 0 |
| *P. interpunctella* – helper | 3 | 0 | 1 |
| *T. ni* – helper | 45 | 7 | 2 |
| *S. frugiperda* + helper | 38 | 6 | 1 |
| *S. frugiperda* – helper | 21 | 14 | 0 |
| *A. aegypti* + *helper* | 7 | 2 | 0 |
| *A. aegypti* – *helper* | 13 | 1 | 0 |
| *D. melanogaster* | 1 | 0 | 0 |

EXAMPLE 11

A phsp 70/opd plasmid and helper p3E1.2 were coinjected into *T. ni* eggs as described above in example 8. The hsp70/opd gene fusion construct (Benedict et al, *Insect Mol. Biol.*, Volume 3, 247–252, 1194; herein incorporated by reference) was used as the targeted DNA in the transformation construct used for obtaining transgenic *T. ni*. The opd gene product confers resistance to the insecticide paraoxon. opd is an abbreviation for the parathion hydrolase gene, in this case isolated from *Pseudomonas diminuta* (Benedict et al; supra). The product of this gene metabolizes numerous organophosphorous nerve agents including the insecticides parathion and paraoxon. The particular gene used in this construct encodes a native, cytoplasmic form of the hydrolase protein, and is therefore referred to as copd. The hsp70 heat shock promoter is an inducible promoter that provides high-level expression of the bacterial opd gene when induced. The hsp70/opd gene construct was inserted into pIFP2BX to form phsp/opd plasmid. The p3E1.2hs/opd plasmid was constructed by inserting a PCR amplified hs/opd fragment using primers tailed with BglII sites directly into the unique BglII site within p3E1.2 plasmid, effectively positioning the hs/opd gene within the piggyBac sequence (FIGS. 12*b*–12*m*, SEQ ID NO 20, and SEQ ID NO 19). The primers SEQ ID NO 18 used for the amplification are shown in FIG. 12*a*.

The eggs were hatched and subsequently mass-nated. The $G_1$ progeny of the mass-mated microinjected insects were permitted to feed for about 24 ours, heat-shocked for about 60 minutes at about 42° C., rested at about 26° C. and allowed to feed for about an additional 18 hours before being subjected to selection. These heat stressed caterpillars were then allowed to crawl for about 30 minutes on approximately 50 ug/cm$_2$ paraoxon-treated filter paper disks. Nearly about 30% of all the G2 larvae survived the initial approximately 50 ug/cm$^2$ dose at a 30 min exposure, while all of the control larvae perished. Cloning of piggyBac sequences seemed to confirm transposition into the genome. Southern blot analysis confirmed the presence of multiple, dispersed copies of piggyBac in the genome of transformed insect progeny (G2) at levels above the two or three copies that serve as background in this insect. All but one of these surviving G1 insects died over the next three days, probably from residual paraoxon. The one putative transformed insect that was obtained was paraoxon resistant and had white eyes. This transformant did not generate fertile eggs and a lineage could not be established.

EXAMPLE 12

A helper plasmid construct was prepared that would supply the transposase activity but would not be capable of transposing. The use of this construct allows the production of transgenic insects having only the desired exogenous DNA inserted into the genome. The construct, 3E1.2 delta TRL was prepared by digesting plasmid p3E1.2 with SstI to remove a DNA fragment from nucleotide 3441 to 3724 of p3E1.2. Removal of this fragment deletes the right terminal. repeat of the piggyBac transposon preventing the element from transposing. The sequence of 3E1.2 delta TRL, SEQ ID NO 10, is as follows:

```
  1 TCGCGCGTTT CGGTGATGAC GGTGAAAACC
    TCTGACACAT GCAGCTCCCG GAGACGGTCA
 61 CAGCTTGTCT GTAAGCGGAT GCCGGGAGCA
    GACAAGCCCG TCAGGGCGCG TCAGCGGGTG
121 TTGGCGGGTG TCGGGGCTGG CTTAACTATG
    CGGCATCAGA GCAGATTGTA CTGAGAGTGC
```

181 ACCATATGCG GTGTGAAATA CCGCACAGAT
GCGTAAGGAG AAAATACCGC ATCAGGCGCC
241 ATTCGCCATT CAGGCTGCGC AACTGTTGGG
AAGGGCGATC GGTGCGGGCC TCTTCGCTAT
301 TACGCCAGCT GGCGAAAGGG GGATGTGCTG
CAAGGCGATT AAGTTGGGTA ACGCCAGGGT
361 TTTCCCAGTC ACGACGTTGT AAAACGACGG
CCAGTGCCAA GCTTTGTTTA AAATATAACA
421 AAATTGTGAT CCCACAAAAT GAAGTGGGGC
AAAATCAAAT AATTAACTAG TGTCCGTAAA
481 CTTGTTGGTC TTCAACTTTT TGAGGAACAC
GTTGGACGGC AAATCGTGAC TATAACACAA
541 GTTGATTTAA TAATTTTAGC CAACACGTCG
GGCTGCGTGT TTTTTGCGCT CTGTGTACAC
601 GTTGATTAAC TGGTCGATTA AATAATTTAA
TTTTTGGTTC TTCTTTAAAT CTGTGATGAA
661 ATTTTTTAAA ATAACTTTAA ATTCTTCATT
GGTAAAAAAT GCCACGTTTT GCAACTTGTG
721 AGGGTCTAAT ATGAGGTCAA ACTCAGTAGG
AGTTTTATCC AAAAAAGAAA ACATGATTAC
781 GTCTGTACAC GAACGCGTAT TAACGCAGAG
TGCAAAGTAT AAGAGGGTTA AAAATATAT
841 TTTACGCACC ATATACGCAT CGGGTTGATA
TCGTTAATAT GGATCAATTT GAACAGTTGA
901 TTAACGTGTC TCTGCTCAAG TCTTTGATCA
AAACGCAAAT CGACGAAAAT GTGTCGGACA
961 ATATCAAGTC GATGAGCGAA AAACTAAAAA
GGCTAGAATA CGACAATCTC ACAGACAGCG
1021 TTGAGATATA CGGTATTCAC GACAGCAGGC
TGAATAATAA AAAAATTAGA AACTATTATT
1081 TAACCCTAGA AAGATAATCA TATTGTGACG
TACGTTAAAG ATAATCATGC GTAAAATTGA
1141 CGCATGTGTT TTTATCGGTC TGTATATCGA
GGTTTATTTA TTAATTTGAA TAGATATTAA
1201 GTTTTATTAT ATTTACACTT ACATACTAAT
AATAAATTCA ACAAACAATT TATTTATGTT
1261 TATTTATTTA TTAAAAAAAA ACAAAAACTC
AAAATTTCTT CTAAAGTAAC AAAACTTTTA
1321 AACATTCTCT CTTTTACAAA AATAAACTTA
TTTTGTACTT TAAAAACAGT CATGTTGTAT
1381 TATAAAATAA GTAATTAGCT TAACTTATAC
ATAATAGAAA CAAATTATAC TTATTAGTCA
1441 GTCCAGAAAC AACTTTGGCA CATATCAATA
TTATGCTCTC GACAAATAAC TTTTTTGCAT
1501 TTTTTGCACG ATGCATTTGC CTTTCGCCTT
ATTTTAGAGG GGCAGTAAGT ACAGTAAGTA
1561 CGTTTTTTCA TTACTGGCTC TTCAGTACTG
TCATCTGATG TACCAGGCAC TTCATTTGGC
1621 AAAATATTAG AGATATTATC GCGCAAATAT
CTCTTCAAAG TAGGAGCTTC TAAACGGTTA
1681 CGCATAAACG ATGACGTCAG GCTCATGTAA
AGGTTTCTCA TAAATTTTTT GCGACTTTGA
1741 ACCTTTTCTC CCTTGCTACT GACATTATGG
CTGTATATAA TAAAAGAATT TATGCAGGCA
1801 ATGTTTATCA TTCCGTACAA TAATGCCATA
GGCCACCTAT TCGTCTTCCT ACTGCAGGTC
1861 ATCACAGAAC ACATTTGGTC TAGCGTGTCC
ACTCCGCCTT TAGTTTGATT ATAATACATA
1921 ACCATTTGCG GTTTACCGGT ACTTTCGTTG
ATAGAAGCAT CCTCATCACA AGATGATAAT
1981 AAGTATACCA TCTTAGCTGG CTTCGGTTTA
TATGAGACGA GAGTAAGGGG TCCGTCAAAA
2041 CAAAACATCG ATGTTCCCAC TGGCCTGGAG
CGACTGTTTT TCAGTACTTC CGGTATCTCG
2101 CGTTTGTTTG ATCGCACGGT TCCCACAATG
GTTAACTTAT ACGGTTCTTG TAGTAAGTTT
2161 TTTGCCAAAG GGATTGAGGT GAACCAATTG
TCACACGTAA TATTACGACA ACTACCGTGC
2221 ACAGGCTTTG ATAACTCCTT CACGTAGTAT
TCACCGAGTG GTACTCCGTT GGTCTGTGTT
2281 CCTCTTCCCA AATAAGGCAT TCCATTTATC
ATATACTTCG TACCACTGTC ACACATCATG
2341 AGGATTTTTA TTCCATACTT ACTTGGCTTG
TTTGGGATAT ACATCCTAAA CGGACACCGT
2401 CCTCTAAAAC CAAGTAACTG TTCATCTATG
GTCAAATGAG CCCCTGGAGT GTAATTTTGT
2461 ATGCACTGAT GGATAAAGAG ATCCCATATT
TTTCTAACAG GAGTAAATAC ATCGTTTTCT
2521 CGAAGTGTGG GCCGTATACT TTTGTCATCC
ATTCTAAGAC ATCGTATCAA AAAATCCAAA
2581 ACGATCCACA GACTCATTAC AGAGACGTAC
ACATTGACAA AGATCGATCC AAAGAGGTCA
2641 TCTGTGGACA TGTGGTTATC TTTTCTCACT
GCTGTCATTA CCAGAATACC AAAGAAAGCA
2701 TAGATTTCAT CTTCATTCGT GTCACGAAAT
GTAGCACCTG TCATAGATTC CCGACGTTTC
2761 AATGATATCT CAGCATTTGT CCATTTTACA
ATTTGCGAAA TTATCTCATC AGTAAAAAAT
2821 AGTTTGAAGC ATAAAAGTGG GTCATATATA
TTGCGGCACA TACGCGTCGG ACCTCTTTGA
2881 GATCTGACAA TGTTCAGTGC AGAGACTCGG
CTACCGCTCG TGGACTTTGA AGTTGACCAA
2941 CAATGTTTAT TCTTACCTCT AATAGTCCTC
TGTGGCAAGG TCAAGATTCT GTTAGAAGCC
3001 AATGAAGAAC CTGGTTGTTC AATAACATTT
TGTTCGTCTA ATATTTCACT ACGCTTGACG
3061 TTGGCTGACA CTTCATGTAC CTCATCTATA
AACGCTTCTT CTGTATCGCT CTGGACGTCT
3121 TCACTTACGT GATCTGATAT TTCACTGTCA
GAATCCTCAC CAACAAGCTC GTCATCGCCT
3181 TGCAGAAGAG CAGAGAGGAT ATGCT-
CATCG TCTAAAGAAC ATCCCATTTT
ATTATATATT
3241 AGTCACGATA TCTATAACAA GAAAATATAT
ATATAATAAG TTATCACGTA AGTAGAACAT
3301 GAAATAACAA TATTAATTAT CGTATGAGTT
AAATCTTAAA AGTCACGTAA AAGATAATCA
3361 TGCGTCATTT TGACTCACGC GGTCGTTATA
GTTCAAAATC AGTGACACTT ACCGCATTGA
3421 CAAGCACGCC TCAGCCGAGC TCGAATTCGT
AATCATGGTC ATAGCTGTTT CCTGTGTGAA
3481 ATTGTTATCC GCTCACAATT CCACACAACA
TACGAGCCGG AAGCATAAAG TGTAAAGCCT
3541 GGGGTGCCTA ATGAGTGAGC TAACTCACAT
TAATTGCGTT GCGCTCACTG CCCGCTTTCC
3601 AGTCGGGAAA CCTGTCGTGC CAGCTGCATT
AATGAATCGG CCAACGCGCG GGGAGAGGCG
3661 GTTTGCGTAT TGGGCGCTCT TCCGCTTCCT
CGCTCACTGA CTCGCTGCGC TCGGTCGTTC
3721 GGCTGCGGCG AGCGGTATCA GCTCACTCAA
AGGCGGTAAT ACGGTTATCC ACAGAATCAG
3781 GGGATAACGC AGGAAAGAAC ATGTGAG-
CAA AAGGCCAGCA AAAGGCCAGG AACCG-
TAAAA

3841 AGGCCGCGTT GCTGGCGTTT TTCCATAGGC TCCGCCCCCC TGACGAGCAT CACAAAAATC
3901 GACGCTCAAG TCAGAGGTGG CGAAACCCGA CAGGACTATA AAGATACCAG GCGTTTCCCC
3961 CTGGAAGCTC CCTCGTGCGC TCTCCTGTTC CGACCCTGCC GCTTACCGGA TACCTGTCCG
4021 CCTTTCTCCC TTCGGGAAGC GTGGCGCTTT CTCAATGCTC ACGCTGTAGG TATCTCAGTT
4081 CGGTGTAGGT CGTTCGCTCC AAGCTGGGCT GTGTGCACGA ACCCCCCGTT CAGCCCGACC
4141 GCTGCGCCTT ATCCGGTAAC TATCGTCTTG AGTCCAACCC GGTAAGACAC GACTTATCGC
4201 CACTGGCAGC AGCCACTGGT AACAGGATTA GCAGAGCGAG GTATGTAGGC GGTGCTACAG
4261 AGTTCTTGAA GTGGTGGCCT AACTACGGCT ACACTAGAAG GACAGTATTT GGTATCTGCG
4321 CTCTGCTGAA GCCAGTTACC TTCGGAAAAA GAGTTGGTAG CTCTTGATCC GGCAAACAAA
4381 CCACCGCTGG TAGCGGTGGT TTTTTTGTTT GCAAGCAGCA GATTACGCGC AGAAAAAAAG
4441 GATCTCAAGA AGATCCTTTG ATCTTTTCTA CGGGGTCTGA CGCTCAGTGG AACGAAAACT
4501 CACGTTAAGG GATTTTGGTC ATGAGATTAT CAAAAAGGAT CTTCACCTAG ATCCTTTTAA
4561 ATTAAAAATG AAGTTTTAAA TCAATCTAAA GTATATATGA GTAAACTTGG TCTGACAGTT
4621 ACCAATGCTT AATCAGTGAG GCACCTATCT CAGCGATCTG TCTATTTCGT TCATCCATAG
4681 TTGCCTGACT CCCCGTCGTG TAGATAACTA CGATACGGGA GGGCTTACCA TCTGGCCCCA
4741 GTGCTGCAAT GATACCGCGA GACCCACGCT CACCGGCTCC AGATTTATCA GCAATAAACC
4801 AGCCAGCCGG AAGGGCCGAG CGCAGAAGTG GTCCTGCAAC TTTATCCGCC TCCATCCAGT
4861 CTATTAATTG TTGCCGGGAA GCTAGAGTAA GTAGTTCGCC AGTTAATAGT TTGCGCAACG
4921 TTGTTGCCAT TGCTACAGGC ATCGTGGTGT CACGCTCGTC GTTTGGTATG GCTTCATTCA
4981 GCTCCGGTTC CCAACGATCA AGGCGAGTTA CATGATCCCC CATGTTGTGC AAAAAAGCGG
5041 TTAGCTCCTT CGGTCCTCCG ATCGTTGTCA GAAGTAAGTT GGCCGCAGTG TTATCACTCA
5101 TGGTTATGGC AGCACTGCAT AATTCTCTTA CTGTCATGCC ATCCGTAAGA TGCTTTTCTG
5161 TGACTGGTGA GTACTCAACC AAGTCATTCT GAGAATAGTG TATGCGGCGA CCGAGTTGCT
5221 CTTGCCCGGC GTCAATACGG GATAATACCG CGCCACATAG CAGAACTTTA AAAGTGCTCA
5281 TCATTGGAAA ACGTTCTTCG GGGCGAAAAC TCTCAAGGAT CTTACCGCTG TTGAGATCCA
5341 GTTCGATGTA ACCCACTCGT GCACCCAACT GATCTTCAGC ATCTTTTACT TTCACCAGCG
5401 TTTCTGGGTG AGCAAAAACA GGAAGGCAAA ATGCCGCAAA AAAGGGAATA AGGGCGACAC
5461 GGAAATGTTG AATACTCATA CTCTTCCTTT TTCAATATTA TTGAAGCATT TATCAGGGTT
5521 ATTGTCTCAT GAGCGGATAC ATATTTGAAT GTATTTAGAA AAATAAACAA ATAGGGGTTC
5581 CGCGCACATT TCCCCGAAAA GTGCCACCTG ACGTCTAAGA AACCATTATT ATCATGACAT
5641 TAACCTATAA AAATAGGCGT ATCACGAGGC CCTTTCGTC

EXAMPLE 13

The phsp70/opd plasmid (Example 11 supra) was inserted into p3E1.2 by cutting p3E1.2 with Cla I and then ligating with an adaptor containing a Cla I half-site and Apa I site. The construct was then cut with Apa I and Bam HI. The fragment was gel purified and ligated with gel purified Apa I/Bgl II phsp70/opd fragment. This plasmid is designated piggyBac/opd (FIGS. 7a–7e, SEQ ID NO 14). The phsp/opd marker gene was coinjected with the piggyBac element of p3E1.2 plasmid into *Plodia interpunctella* genome to test the marker. This confirmed that the hsp/opd gene is an effective selectable marker gene for detecting transformations in insects (Data not shown).

Transformations were attempted by injecting fertile eggs of the Indianmeal moth, *Ploida interpunctella* with the piggyBac/opd plasmid with the p3E1.2ΔTRL helper (described above in Example 11) as described above in Example 8. The insects were hatched and mass-mated. The $G_1$ progeny of the mass-mated microinjected insects were permitted to feed for about 24 hours, heat-shocked for about 60 minutes at about 42° C., rested for about 60 minutes at about 26° C. and allowed to feed before being subjected to selection on paraoxon. The optimum time interval between heat shock and paraoxon treatment for *P. interpunctella* is about 4 to about 8 hours for a maximum period for resistance The heated stressed caterpillars and then allowed to crawl for about 30 minutes on approximately 50 μgram/cm2 paraoxon-treated filter paper disks.

Figure 8:
FIG. 8 is a Southern blot of the PiA-3 and PiA-11 piggyBac transformed *Plodia interpunctella* strains. Genomic DNA was extracted from $G_{10}$ larvae of the PiA-3 and PiA-11 strains of *P. interpunctella* strains that were coinjected with piggyBac/opd and p3E1.2ΔTRL. Lanes A–C contain 2.5 micrograms each of PiA-11 genomic DNA; lanes D and J are blank; lanes E–H contain piggyBac/opd DNA; lane I contains 2.5 micrograms of wild type *P. interpunctella* DNA; lanes K–M contain 2.5 micrograms of PiA-3 DNA. Lanes A,E and K are PstI digests; lanes B,F and L are EcoRI digests; lanes C,G and M are ApaI digests. Lane H is uncut DNA. The blot was hybridized with PCR labeled probe to hsp70/opd.

Four independent transformed lines were recovered which are now in $G_{16}$. Three of these lines are white-eyed mutants. These transformation induced white-eyed mutants of *P. interpunctella* are genetically similar to those recovered from the laboratory strain as spontaeous white-eyed mutations, because matings between the transformation induced white-eyed insects and the spontaneous white-eyed mutants showed no complementation between the strains. Southern blots of genomic DNA from larvae that were in the tenth generation of these lines show positive hybridization profiles for both piggyBac and hsp/opd sequences that are unique for each strain (FIG. 8, compare lane B with L and C with M). Genomic DNA was extracted from G10 larvae of the PiA-3 and PiA-11 strains of *P. interpunctella* that were coinjected with piggyBac/opd and p3E1.2ΔTRL. These results indicate that the Indian meal moth, *P. interpunctella* has been genetically transformed using the piggyBac/opd plasmid as the transforming vector.

The foregoing detailed description is for the purpose of illustration. Such detail is solely for that purpose and those skilled in the art can make variations without departing from the spirit and scope of the invention.

We claim:

1. A transformation system comprising:
   (a) a first DNA comprising a non-transposon heterologous DNA sequence inserted between a pair of inverted repeats of a piggyBac transposon, and
   (b) a second DNA encoding a transposase active on the pair of inverted repeats,
   wherein the second DNA is incapable of transposition caused by said transposon.

2. The transformation system of claim 1 wherein the pair of inverted repeats is a pair of 13 base-pair inverted repeats.

3. The transformation system of claim 2 wherein the pair of 13 base-pair inverted repeats consists of SEQ ID NO 2 and SEQ ID NO 3.

4. The transformation system of claim 1 wherein the pair of inverted repeats is a pair of 17 base-pair inverted repeats.

5. The transformation system of claim 4 wherein the pair of 17 base-pair inverted repeats consists of SEQ ID NO 4 and SEQ ID NO 5.

6. The transformation system of claim 1 wherein the non-transposon heterologous DNA sequence inserted between the pair of inverted repeats is inserted into an endonuclease restriction site within a polylinker sequence.

7. The transformation system of claim 1 wherein the second DNA is contained within the genome of a cell targeted for transformation.

8. The transformation system of claim 1 wherein the second DNA is a plasmid contained within a cell targeted for transformation.

9. The transformation system of claim 1 wherein said second DNA is physically linked to said first DNA.

10. The transformation system of claim 1 wherein the second DNA is a separate DNA molecule from the first DNA.

11. A method of introducing a heterologous DNA sequence into the genome of a cultured cell of interest comprising:
    (a) introducing into the cell a first nucleic acid comprising a non-transposon heterologous DNA sequence inserted between a pair of inverted repeats of a piggyBac transposon; and
    (b) providing the cell with a second nucleic acid that encodes a transposase active on the pair of inverted repeats such that the heterologous DNA sequence is inserted into the genome of the cell, said second nucleic acid characterized in that it is incapable of transposition by the transposase.

12. The method of claim 11 wherein the providing step comprises transfecting with a nucleic acid encoding the transposase.

13. The method of claim 11 wherein the providing step comprises inducing expression from a genomic sequence encoding the transposase.

14. The method of claim 11 wherein the first and second nucleic acid are introduced by microinjection, high velocity propulsion, permeabilization, fusion with DNA-containing entities, or electroporation.

15. The method of claim 11 wherein the pair of inverted repeats is a pair of 13 base-pair inverted repeats.

16. The method of claim 15 wherein the pair of 13 base-pair inverted repeats consists of SEQ ID NO 2 and SEQ ID NO 3.

17. The method of claim 11 wherein the pair of inverted repeats is a pair of 17 base-pair inverted repeats.

18. The method of claim 17 wherein the pair of 17 base-pair inverted repeats consists of SEQ ID NO 4 and SEQ ID NO 5.

19. The method of claim 11 wherein the non-transposon heterologous DNA sequence inserted between the pair of inverted repeats is inserted into an endonuclease restriction site within a polylinker sequence.

20. A cell comprising:
    (a) a first DNA comprising a non-transposon heterologous DNA sequence inserted between a pair of inverted repeats of a piggyBac transposon; and
    (b) a second DNA encoding a transposase active on a pair of inverted repeats, which second DNA is incapable of transposition caused by the transposase.

21. The cell of claim 20 wherein the second DNA sequence is operably linked to an inducible promoter.

22. The cell of claim 21 wherein the inducible promoter comprises a heat shock promoter, a metallothionein promoter, or a glucocorticoid response element.

23. The cell of claim 20 wherein the non-transposon heterologous DNA sequence comprises a selectable marker.

24. The cell of claim 23 wherein the selectable marker is antibiotic resistance, pesticide resistance, insecticide resistance, herbicide resistance, green fluorescent protein, amber mutation, or lacZ.

25. The cell of claim 20 wherein the second DNA is physically linked to the first DNA.

26. The cell of claim 20 wherein the second DNA is a separate DNA molecule from the first DNA.

27. A cell comprising:
(a) a first DNA comprising a non-transposon heterologous DNA sequence operably linked to an inducible promoter and inserted between a pair on inverted repeats of a pigyyBac transposon; and
(b) a second DNA encoding a transposase active on a pair of inverted repeats.

28. The cell of claim 27 wherein the second DNA is a separate DNA molecule from the first DNA.

\* \* \* \* \*

UNITED STATES PATENT AND TRADEMARK OFFICE
CERTIFICATE OF CORRECTION

PATENT NO.    : 6,218,185 B1
DATED         : April 17, 2001
INVENTOR(S)   : Malcolm J. Fraser Jr. et al.

It is certified that error appears in the above-identified patent and that said Letters Patent is hereby corrected as shown below:

<u>Title page,</u>
Item [75], the first named inventor should be -- Malcolm J. Fraser, Jr. --not "Paul D. Shirk."

Signed and Sealed this

First Day of April, 2003

JAMES E. ROGAN
*Director of the United States Patent and Trademark Office*

SEQUENCE LISTING

<160> NUMBER OF SEQ ID NOS: 22

<210> SEQ ID NO 1
<211> LENGTH: 7
<212> TYPE: DNA
<213> ORGANISM: Artificial Sequence
<220> FEATURE:
<223> OTHER INFORMATION: Description of Artificial Sequence:F1-2

<400> SEQUENCE: 1 ttaaccc                                                                    7

<210> SEQ ID NO 2
<211> LENGTH: 13
<212> TYPE: DNA
<213> ORGANISM: Artificial Sequence
<220> FEATURE:
<223> OTHER INFORMATION: Description of Artificial Sequence:M17-4

<400> SEQUENCE: 2
ccctagaaag ata                                                             13

<210> SEQ ID NO 3
<211> LENGTH: 13
<212> TYPE: DNA
<213> ORGANISM: Artificial Sequence
<220> FEATURE:
<223> OTHER INFORMATION: Description of Artificial Sequence:M17-4

<400> SEQUENCE: 3
tatctttcta ggg                                                             13

<210> SEQ ID NO 4
<211> LENGTH: 17
<212> TYPE: DNA
<213> ORGANISM: Trichoplusia ni

<400> SEQUENCE: 4
ttaaccctag aaagata                                                         17

<210> SEQ ID NO 5
<211> LENGTH: 17
<212> TYPE: DNA
<213> ORGANISM: Trichoplusia ni

<400> SEQUENCE: 5
tatctttcta gggttaa                                                         17

<210> SEQ ID NO 6
<211> LENGTH: 7
<212> TYPE: DNA
<213> ORGANISM: Trichoplusia ni

<400> SEQUENCE: 6 gggttaa                                                                    7

<210> SEQ ID NO 7
<211> LENGTH: 29
<212> TYPE: DNA
<213> ORGANISM: Artificial Sequence
<220> FEATURE:
<223> OTHER INFORMATION: Description of Artificial
      Sequence:primer olignucleotide MF34

-continued

<400> SEQUENCE: 7
ggatcctcta gattaaccct agaaagata                29

<210> SEQ ID NO 8
<211> LENGTH: 29
<212> TYPE: DNA
<213> ORGANISM: Trichoplusia ni

<400> SEQUENCE: 8
ggatcctcta gattaactct agaggatcc                29

<210> SEQ ID NO 9
<211> LENGTH: 6
<212> TYPE: DNA
<213> ORGANISM: Artificial Sequence
<220> FEATURE:
<223> OTHER INFORMATION: Description of Artificial Sequence:AseI site

<400> SEQUENCE: 9 attaat                                          6

<210> SEQ ID NO 10
<211> LENGTH: 5679
<212> TYPE: DNA
<213> ORGANISM: Artificial Sequence
<220> FEATURE:
<223> OTHER INFORMATION: Description of Artificial
      Sequence:p3E1.2 delta TRL

<400> SEQUENCE: 10
tcgcgcgttt cggtgatgac ggtgaaaacc tctgacacat gcagctcccg gagacggtca    60
cagcttgtct gtaagcggat gccgggagca gacaagcccg tcaggcgcg tcagcgggtg    120 ttggcgggtg tcggggctgg cttaactatg cggcatcaga gcagattgta ctgagagtgc    180
accatatgcg gtgtgaaata ccgcacagat gcgtaaggag aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gctttgttta aaatataaca    420
aaattgtgat cccacaaaat gaagtggggc aaaatcaaat aattaactag tgtccgtaaa    480
cttgttggtc ttcaactttt tgaggaacac gttggacggc aaatcgtgac ataacacaa    540 gttgatttaa taattttagc caacacgtcg ggctgcgtgt tttttgcgct ctgtgtacac    600
gttgattaac tggtcgatta aataatttaa ttttggttc ttctttaaat ctgtgatgaa    660 atttttttaaa ataactttaa attcttcatt ggtaaaaat gccacgtttt gcaacttgtg    720
agggtctaat atgaggtcaa actcagtagg agtttatcc aaaaagaaa acatgattac    780 gtctgtacac gaacgcgtat taacgcagag tgcaaagtat aagagggtta aaaatatat    840 tttacgcacc atatacgcat cgggttgata tcgttaatat ggatcaattt gaacagttga    900
ttaacgtgtc tctgctcaag tctttgatca aaacgcaaat cgacgaaaat gtgtcggaca    960
atatcaagtc gatgagcgaa aaactaaaaa ggctagaata cgacaatctc acagacagcg    1020
ttgagatata cggtattcac gacagcaggc tgaataataa aaaaattaga aactattatt    1080
taaccctaga aagataatca tattgtgacg tacgttaaag ataatcatgc gtaaaattga    1140
cgcatgtgtt tttatcggtc tgtatatcga ggtttatta ttaatttgaa tagatattaa    1200
gttttattat atttacactt acatactaat aataaattca acaaacaatt tatttatgtt    1260

-continued

```
tatttattta ttaaaaaaaa acaaaaactc aaaatttctt ctaaagtaac aaaactttta    1320
aacattctct cttttacaaa aataaactta ttttgtactt taaaaacagt catgttgtat    1380
tataaaataa gtaattagct taacttatac ataatagaaa caaattatac ttattagtca    1440
gtccagaaac aactttggca catatcaata ttatgctctc gacaaataac ttttttgcat    1500
tttttgcacg atgcatttgc ctttcgcctt attttagagg ggcagtaagt acagtaagta    1560
cgttttccta ttactggctc ttcagtactg tcatctgatg taccaggcac ttcatttggc    1620
aaaatattag agatattatc gcgcaaatat ctcttcaaag taggagcttc taaacggtta    1680
cgcataaacg atgacgtcag gctcatgtaa aggtttctca taaattttttt gcgactttga    1740 acctttctc ccttgctact gacattatgg ctgtatataa taaaagaatt tatgcaggca    1800
atgtttatca ttccgtacaa taatgccata ggccacctat tcgtcttcct actgcaggtc    1860
atcacagaac acatttggtc tagcgtgtcc actccgcctt tagtttgatt ataatacata    1920
accatttgcg gtttaccggt actttcgttg atagaagcat cctcatcaca agatgataat    1980
aagtatacca tcttagctgg cttcggttta tatgagacga gagtaagggg tccgtcaaaa    2040
caaaacatcg atgttcccac tggcctggag cgactgtttt tcagtacttc cggtatctcg    2100
cgtttgtttg atcgcacggt tcccacaatg gttaacttat acggttcttg tagtaagttt    2160
tttgccaaag ggattgaggt gaaccaattg tcacacgtaa tattacgaca actaccgtgc    2220
acaggctttg ataactcctt cacgtagtat tcaccgagtg gtactccgtt ggtctgtgtt    2280
cctcttccca aataaggcat tccatttatc atatacttcg taccactgtc acacatcatg    2340
aggattttta ttccatactt acttggcttg tttgggatat acatcctaaa cggacaccgt    2400
cctctaaaac caagtaactg ttcatctatg gtcaaatgag cccctggagt gtaattttgt    2460
atgcactgat ggataaagag atcccatatt tttctaacag gagtaaatac atcgttttct    2520
cgaagtgtgg gccgtatact tttgtcatcc attctaagac atcgtatcaa aaatccaaa    2580 acgatccaca gactcattac agagacgtac acattgacaa agatcgatcc aaagaggtca    2640
tctgtggaca tgtggttatc ttttctcact gctgtcatta ccagaatacc aaagaaagca    2700
tagatttcat cttcattcgt gtcacgaaat gtagcacctg tcatagattc ccgacgtttc    2760
aatgatatct cagcatttgt ccattttaca atttgcgaaa ttatctcatc agtaaaaaat    2820
agtttgaagc ataaaagtgg gtcatatata ttgcggcaca tacgcgtcgg acctctttga    2880
gatctgacaa tgttcagtgc agagactcgg ctaccgctcg tggactttga agttgaccaa    2940
caatgtttat tcttacctct aatagtcctc tgtggcaagg tcaagattct gttagaagcc    3000
aatgaagaac ctggttgttc aataacattt tgttcgtcta atatttcact acgcttgacg    3060
ttggctgaca cttcatgtac ctcatctata aacgcttctt ctgtatcgct ctggacgtct    3120
tcacttacgt gatctgatat ttcactgtca gaatcctcac caacaagctc gtcatcgcct    3180
tgcagaagag cagagaggat atgctcatcg tctaaagaac atcccatttt attatatatt    3240
agtcacgata tctataacaa gaaaatatat atataataag ttatcacgta agtagaacat    3300
gaaataacaa tattaattat cgtatgagtt aaatcttaaa agtcacgtaa aagataatca    3360
tgcgtcattt tgactcacgc ggtcgttata gttcaaaatc agtgacactt accgcattga    3420
caagcacgcc tcagccgagc tcgaattcgt aatcatggtc atagctgttt cctgtgtgaa    3480
attgttatcc gctcacaatt ccacacaaca tacgagccgg aagcataaag tgtaaagcct    3540
ggggtgccta atgagtgagc taactcacat taattgcgtt gcgctcactg cccgctttcc    3600
agtcgggaaa cctgtcgtgc cagctgcatt aatgaatcgg ccaacgcgcg gggagaggcg    3660
```

```
gtttgcgtat tgggcgctct tccgcttcct cgctcactga ctcgctgcgc tcggtcgttc    3720
ggctgcggcg agcggtatca gctcactcaa aggcggtaat acggttatcc acagaatcag    3780
gggataacgc aggaaagaac atgtgagcaa aaggccagca aaaggccagg aaccgtaaaa    3840
aggccgcgtt gctggcgttt ttccataggc tccgccccc tgacgagcat cacaaaaatc    3900
gacgctcaag tcagaggtgg cgaaacccga caggactata agataccag gcgtttcccc    3960 ctggaagctc cctcgtgcgc tctcctgttc cgaccctgcc gcttaccgga tacctgtccg    4020
cctttctccc ttcgggaagc gtggcgcttt ctcaatgctc acgctgtagg tatctcagtt    4080
cggtgtaggt cgttcgctcc aagctgggct gtgtgcacga accccccgtt cagcccgacc    4140
gctgcgcctt atccggtaac tatcgtcttg agtccaaccc ggtaagacac gacttatcgc    4200
cactggcagc agccactggt aacaggatta gcagagcgag gtatgtaggc ggtgctacag    4260
agttcttgaa gtggtggcct aactacggct acactagaag gacactattt ggtatctgcg    4320
ctctgctgaa gccagttacc ttcggaaaaa gagttggtag ctcttgatcc ggcaaacaaa    4380
ccaccgctgg tagcggtggt ttttttgttt gcaagcagca gattacgcgc agaaaaaaag    4440
gatctcaaga agatcctttg atcttttcta cggggtctga cgctcagtgg aacgaaaact    4500
cacgttaagg gattttggtc atgagattat caaaaaggat cttcacctag atccttttaa    4560
attaaaaatg aagttttaaa tcaatctaaa gtatatatga gtaaacttgg tctgacagtt    4620
accaatgctt aatcagtgag gcacctatct cagcgatctg tctatttcgt tcatccatag    4680
ttgcctgact ccccgtcgtg tagataacta cgatacggga gggcttacca tctggcccca    4740
gtgctgcaat gataccgcga gacccacgct caccggctcc agatttatca gcaataaacc    4800
agccagccgg aagggccgag cgcagaagtg gtcctgcaac tttatccgcc tccatccagt    4860
ctattaattg ttgccgggaa gctagagtaa gtagttcgcc agttaatagt ttgcgcaacg    4920
ttgttgccat tgctacaggc atcgtggtgt cacgctcgtc gtttggtatg gcttcattca    4980
gctccggttc ccaacgatca aggcgagtta catgatcccc catgttgtgc aaaaaagcgg    5040
ttagctcctt cggtcctccg atcgttgtca gaagtaagtt ggccgcagtg ttatcactca    5100
tggttatggc agcactgcat aattctctta ctgtcatgcc atccgtaaga tgcttttctg    5160
tgactggtga gtactcaacc aagtcattct gagaatagtg tatgcggcga ccgagttgct    5220
cttgcccggc gtcaatacgg gataataccg cgccacatag cagaacttta aaagtgctca    5280
tcattggaaa acgttcttcg gggcgaaaac tctcaaggat cttaccgctg ttgagatcca    5340
gttcgatgta acccactcgt gcacccaact gatcttcagc atcttttact ttcaccagcg    5400
tttctgggtg agcaaaaaca ggaaggcaaa atgccgcaaa aaagggaata agggcgacac    5460
ggaaatgttg aatactcata ctcttccttt ttcaatatta ttgaagcatt tatcagggtt    5520
attgtctcat gagcggatac atatttgaat gtatttagaa aaataaacaa ataggggttc    5580
cgcgcacatt tccccgaaaa gtgccacctg acgtctaaga aaccattatt atcatgacat    5640
taacctataa aaataggcgt atcacgaggc cctttcgtc                           5679
```

<210> SEQ ID NO 11

<211> LENGTH: 2476

<212> TYPE: DNA
<213> ORGANISM: Trichoplusia ni
<220> FEATURE:
<221> NAME/KEY: CDS
<222> LOCATION: (333)..(2123)

<400> SEQUENCE: 11

```
ccctagaaag atagtctgcg taaaattgac gcatgcattc ttgaaatatt gctctctctt      60
tctaaatagc gcgaatccgt cgctgtttgc aatttaggac atctcagtcg ccgcttggag     120
ctcggctgag gcgtgcttgt caatgcggta agtgtcactg attttgaact ataacgaccg     180
cgtgagtcaa aatgacgcat gattatcttt tacgtgactt ttaagattta actcatacga    240
taattaatat tgttatttca tgttctactt acgtgataac ttattatata tatattttct    300
tgttatagat atcgtgacta atatataata aa atg gga tgt tct tta gac gat      353
                                    Met Gly Cys Ser Leu Asp Asp
                                      1               5 gag cat atc ctc tct gct ctt ctg caa ggc gat gac gag ctt gtt ggt      401
Glu His Ile Leu Ser Ala Leu Leu Gln Gly Asp Asp Glu Leu Val Gly
         10                  15                  20 gag gat tct gac agt gaa ata tca gat cac gta agt gaa gac gtc cag      449
Glu Asp Ser Asp Ser Glu Ile Ser Asp His Val Ser Glu Asp Val Gln
     25                  30                  35 agc gat aca gaa gaa gcg ttt ata gat gag gta cat gaa gtg tca gcc      497
Ser Asp Thr Glu Glu Ala Phe Ile Asp Glu Val His Glu Val Ser Ala
 40                  45                  50                  55 aac gtc aag cgt agt gaa ata tta gac gaa caa aat gtt att gaa caa      545
Asn Val Lys Arg Ser Glu Ile Leu Asp Glu Gln Asn Val Ile Glu Gln
                 60                  65                  70 cca ggt tct tca ttg gct tct aac aga atc ttg acc ttg cca cag agg      593
Pro Gly Ser Ser Leu Ala Ser Asn Arg Ile Leu Thr Leu Pro Gln Arg
             75                  80                  85 act att aga ggt aag aat aaa cat tgt tgg tca act tca aag tcc acg      641
Thr Ile Arg Gly Lys Asn Lys His Cys Trp Ser Thr Ser Lys Ser Thr
         90                  95                 100 agc ggt agc cga gtc tct gca ctg aac att gtc aga tct caa aga ggt      689
Ser Gly Ser Arg Val Ser Ala Leu Asn Ile Val Arg Ser Gln Arg Gly
    105                 110                 115 ccg acg cgt atg tgc cgc aat ata tat gac cca ctt tta tgc ttc aaa      737
Pro Thr Arg Met Cys Arg Asn Ile Tyr Asp Pro Leu Leu Cys Phe Lys
120                 125                 130                 135 cta ttt ttt act gat gag ata att tcg caa att gta aaa tgg aca aat      785
Leu Phe Phe Thr Asp Glu Ile Ile Ser Gln Ile Val Lys Trp Thr Asn
                140                 145                 150 gct gag ata tca ttg aaa cgt cgg gaa tct atg aca ggt gct aca ttt      833
Ala Glu Ile Ser Leu Lys Arg Arg Glu Ser Met Thr Gly Ala Thr Phe
            155                 160                 165 cgt gac acg aat gaa gat gaa atc tat gct ttc ttt ggt att ctg gta      881
Arg Asp Thr Asn Glu Asp Glu Ile Tyr Ala Phe Phe Gly Ile Leu Val
        170                 175                 180 atg aca gca gtg aga aaa gat aac cac atg tcc aca gat gac ctc ttt      929
Met Thr Ala Val Arg Lys Asp Asn His Met Ser Thr Asp Asp Leu Phe
    185                 190                 195 gga tcg atc ttt gtc aat gtg tac gtc tct gta atg agt ctg tgg atc      977
Gly Ser Ile Phe Val Asn Val Tyr Val Ser Val Met Ser Leu Trp Ile
200                 205                 210                 215 gtt ttg gat ttt ttg ata cga tgt ctt aga atg gat gac aaa agt ata     1025
Val Leu Asp Phe Leu Ile Arg Cys Leu Arg Met Asp Asp Lys Ser Ile
                220                 225                 230 cgg ccc aca ctt cga gaa aac gat gta ttt act cct gtt aga aaa ata     1073
Arg Pro Thr Leu Arg Glu Asn Asp Val Phe Thr Pro Val Arg Lys Ile
            235                 240                 245 tgg gat ctc ttt atc cat cag tgc ata caa aat tac act cca ggg gct     1121
Trp Asp Leu Phe Ile His Gln Cys Ile Gln Asn Tyr Thr Pro Gly Ala
```

-continued

```
            250                 255                 260
cat ttg acc ata gat gaa cag tta ctt ggt ttt aga gga cgg tgt ccg    1169
His Leu Thr Ile Asp Glu Gln Leu Leu Gly Phe Arg Gly Arg Cys Pro
        265                 270                 275 ttt agg atg tat atc cca aac aag cca agt aag tat gga ata aaa atc    1217
Phe Arg Met Tyr Ile Pro Asn Lys Pro Ser Lys Tyr Gly Ile Lys Ile
280                 285                 290                 295 ctc atg atg tgt gac agt ggt acg aag tat atg ata aat gga atg cct    1265
Leu Met Met Cys Asp Ser Gly Thr Lys Tyr Met Ile Asn Gly Met Pro
                300                 305                 310 tat ttg gga aga gga aca cag acc aac gga gta cca ctc ggt gaa tac    1313
Tyr Leu Gly Arg Gly Thr Gln Thr Asn Gly Val Pro Leu Gly Glu Tyr
            315                 320                 325 tac gtg aag gag tta tca aag cct gtg cac ggt agt tgt cgt aat att    1361
Tyr Val Lys Glu Leu Ser Lys Pro Val His Gly Ser Cys Arg Asn Ile
        330                 335                 340 acg tgt gac aat tgg ttc acc tca atc cct ttg gca aaa aac tta cta    1409
Thr Cys Asp Asn Trp Phe Thr Ser Ile Pro Leu Ala Lys Asn Leu Leu
    345                 350                 355 caa gaa ccg tat aag tta acc att gtg gga acc gtg cga tca aac aaa    1457
Gln Glu Pro Tyr Lys Leu Thr Ile Val Gly Thr Val Arg Ser Asn Lys
360                 365                 370                 375 cgc gag ata ccg gaa gta ctg aaa aac agt cgc tcc agg cca gtg gga    1505
Arg Glu Ile Pro Glu Val Leu Lys Asn Ser Arg Ser Arg Pro Val Gly
                380                 385                 390 aca tcg atg ttt tgt ttt gac gga ccc ctt act ctc gtc tca tat aaa    1553
Thr Ser Met Phe Cys Phe Asp Gly Pro Leu Thr Leu Val Ser Tyr Lys
            395                 400                 405 ccg aag cca gct aag atg gta tac tta tta tca tct tgt gat gag gat    1601
Pro Lys Pro Ala Lys Met Val Tyr Leu Leu Ser Ser Cys Asp Glu Asp
        410                 415                 420 gct tct atc aac gaa agt acc ggt aaa ccg caa atg gtt atg tat tat    1649
Ala Ser Ile Asn Glu Ser Thr Gly Lys Pro Gln Met Val Met Tyr Tyr
    425                 430                 435 aat caa act aaa ggc gga gtg gac acg cta gac caa atg tgt tct gtg    1697
Asn Gln Thr Lys Gly Gly Val Asp Thr Leu Asp Gln Met Cys Ser Val
440                 445                 450                 455 atg acc tgc agt agg aag acg aat agg tgg cct atg gca tta ttg tac    1745
Met Thr Cys Ser Arg Lys Thr Asn Arg Trp Pro Met Ala Leu Leu Tyr
                460                 465                 470 gga atg ata aac att gcc tgc ata aat tct ttt att ata tac agc cat    1793
Gly Met Ile Asn Ile Ala Cys Ile Asn Ser Phe Ile Ile Tyr Ser His
            475                 480                 485 aat gtc agt agc aag gga gaa aag gtt caa agt cgc aaa aaa ttt atg    1841
Asn Val Ser Ser Lys Gly Glu Lys Val Gln Ser Arg Lys Lys Phe Met
        490                 495                 500 aga aac ctt tac atg agc ctg acg tca tcg ttt atg cgt aac cgt tta    1889
Arg Asn Leu Tyr Met Ser Leu Thr Ser Ser Phe Met Arg Asn Arg Leu
    505                 510                 515 gaa gct cct act ttg aag aga tat ttg cgc gat aat atc tct aat att    1937
Glu Ala Pro Thr Leu Lys Arg Tyr Leu Arg Asp Asn Ile Ser Asn Ile
520                 525                 530                 535 ttg cca aat gaa gtg cct ggt aca tca gat gac agt act gaa gag cca    1985
Leu Pro Asn Glu Val Pro Gly Thr Ser Asp Asp Ser Thr Glu Glu Pro
                540                 545                 550 gta atg aaa aaa cgt act tac tgt act tac tgc ccc tct aaa ata agg    2033
Val Met Lys Lys Arg Thr Tyr Cys Thr Tyr Cys Pro Ser Lys Ile Arg
            555                 560                 565 cga aag gca aat gca tcg tgc aaa aaa tgc aaa aaa gtt att tgt cga    2081
```

```
Arg Lys Ala Asn Ala Ser Cys Lys Lys Cys Lys Val Ile Cys Arg
        570             575             580 gag cat aat att gat atg tgc caa agt tgt ttc tgg act gac         2123
Glu His Asn Ile Asp Met Cys Gln Ser Cys Phe Trp Thr Asp
        585             590             595 taataagtat aatttgtttc tattatgtat aagttaagct aattacttat tttataatac    2183
aacatgactg tttttaaagt acaaataag tttattttg taaagagag aatgtttaaa      2243 agttttgtta ctttagaaga aattttgagt ttttgttttt ttttaataaa taaataaaca   2303
taaataaatt gtttgttgaa tttattatta gtatgtaagt gtaaatataa taaaacttaa   2363
tatctattca aattaataaa taaacctcga tatacagacc gataaaaaca catgcgtcaa   2423
ttttacgcat gattatcttt aacgtacgtc acaatatgat tatctttcta ggg         2476
```

<210> SEQ ID NO 12
<211> LENGTH: 597
<212> TYPE: PRT
<213> ORGANISM: Trichoplusia ni

<400> SEQUENCE: 12

```
Met Gly Cys Ser Leu Asp Asp Glu His Ile Leu Ser Ala Leu Leu Gln
  1               5                  10                  15

Gly Asp Asp Glu Leu Val Gly Glu Asp Ser Asp Ser Glu Ile Ser Asp
                 20                  25                  30

His Val Ser Glu Asp Val Gln Ser Asp Thr Glu Glu Ala Phe Ile Asp
             35                  40                  45

Glu Val His Glu Val Ser Ala Asn Val Lys Arg Ser Glu Ile Leu Asp
         50                  55                  60

Glu Gln Asn Val Ile Glu Gln Pro Gly Ser Ser Leu Ala Ser Asn Arg
 65                  70                  75                  80

Ile Leu Thr Leu Pro Gln Arg Thr Ile Arg Gly Lys Asn Lys His Cys
                 85                  90                  95

Trp Ser Thr Ser Lys Ser Thr Ser Gly Ser Arg Val Ser Ala Leu Asn
            100                 105                 110

Ile Val Arg Ser Gln Arg Gly Pro Thr Arg Met Cys Arg Asn Ile Tyr
        115                 120                 125

Asp Pro Leu Leu Cys Phe Lys Leu Phe Phe Thr Asp Glu Ile Ile Ser
    130                 135                 140

Gln Ile Val Lys Trp Thr Asn Ala Glu Ile Ser Leu Lys Arg Arg Glu
145                 150                 155                 160

Ser Met Thr Gly Ala Thr Phe Arg Asp Thr Asn Glu Asp Glu Ile Tyr
                165                 170                 175

Ala Phe Phe Gly Ile Leu Val Met Thr Ala Val Arg Lys Asp Asn His
            180                 185                 190

Met Ser Thr Asp Asp Leu Phe Gly Ser Ile Phe Val Asn Val Tyr Val
        195                 200                 205

Ser Val Met Ser Leu Trp Ile Val Leu Asp Phe Leu Ile Arg Cys Leu
    210                 215                 220

Arg Met Asp Asp Lys Ser Ile Arg Pro Thr Leu Arg Glu Asn Asp Val
225                 230                 235                 240

Phe Thr Pro Val Arg Lys Ile Trp Asp Leu Phe Ile His Gln Cys Ile
                245                 250                 255

Gln Asn Tyr Thr Pro Gly Ala His Leu Thr Ile Asp Glu Gln Leu Leu
            260                 265                 270

Gly Phe Arg Gly Arg Cys Pro Phe Arg Met Tyr Ile Pro Asn Lys Pro
```

```
                275                 280                 285
Ser Lys Tyr Gly Ile Lys Ile Leu Met Met Cys Asp Ser Gly Thr Lys
    290                 295                 300
Tyr Met Ile Asn Gly Met Pro Tyr Leu Gly Arg Gly Thr Gln Thr Asn
305                 310                 315                 320
Gly Val Pro Leu Gly Glu Tyr Tyr Val Lys Glu Leu Ser Lys Pro Val
                325                 330                 335
His Gly Ser Cys Arg Asn Ile Thr Cys Asp Asn Trp Phe Thr Ser Ile
                340                 345                 350
Pro Leu Ala Lys Asn Leu Leu Gln Glu Pro Tyr Lys Leu Thr Ile Val
                355                 360                 365
Gly Thr Val Arg Ser Asn Lys Arg Glu Ile Pro Glu Val Leu Lys Asn
    370                 375                 380
Ser Arg Ser Arg Pro Val Gly Thr Ser Met Phe Cys Phe Asp Gly Pro
385                 390                 395                 400
Leu Thr Leu Val Ser Tyr Lys Pro Lys Pro Ala Lys Met Val Tyr Leu
                405                 410                 415
Leu Ser Ser Cys Asp Glu Asp Ala Ser Ile Asn Glu Ser Thr Gly Lys
                420                 425                 430
Pro Gln Met Val Met Tyr Tyr Asn Gln Thr Lys Gly Gly Val Asp Thr
                435                 440                 445
Leu Asp Gln Met Cys Ser Val Met Thr Cys Ser Arg Lys Thr Asn Arg
    450                 455                 460
Trp Pro Met Ala Leu Leu Tyr Gly Met Ile Asn Ile Ala Cys Ile Asn
465                 470                 475                 480
Ser Phe Ile Ile Tyr Ser His Asn Val Ser Ser Lys Gly Glu Lys Val
                485                 490                 495
Gln Ser Arg Lys Lys Phe Met Arg Asn Leu Tyr Met Ser Leu Thr Ser
                500                 505                 510
Ser Phe Met Arg Asn Arg Leu Glu Ala Pro Thr Leu Lys Arg Tyr Leu
                515                 520                 525
Arg Asp Asn Ile Ser Asn Ile Leu Pro Asn Glu Val Pro Gly Thr Ser
    530                 535                 540
Asp Asp Ser Thr Glu Glu Pro Val Met Lys Lys Arg Thr Tyr Cys Thr
545                 550                 555                 560
Tyr Cys Pro Ser Lys Ile Arg Arg Lys Ala Asn Ala Ser Cys Lys Lys
                565                 570                 575
Cys Lys Lys Val Ile Cys Arg Glu His Asn Ile Asp Met Cys Gln Ser
                580                 585                 590
Cys Phe Trp Thr Asp
        595

<210> SEQ ID NO 13
<211> LENGTH: 6723
<212> TYPE: DNA
<213> ORGANISM: Artificial Sequence
<220> FEATURE:
<223> OTHER INFORMATION: Description of Artificial
      Sequence:Clone p3e1.2H/S

<400> SEQUENCE: 13
tcgcgcgttt cggtgatgac ggtgaaaacc tctgacacat gcagctcccg gagacggtca      60
cagcttgtct gtaagcggat gccgggagca gacaagcccg tcaggcgcgc tcagcgggtg     120
ttggcgggtg tcggggctgg cttaactatg cggcatcaga gcagattgta ctgagagtgc     180
```

```
accatatgcg gtgtgaaata ccgcacagat gcgtaaggat aaaataccgc atcaggcgcc    240
attcgccatt caggctgcgc aactgttggg aagggcgatc ggtgcgggcc tcttcgctat    300
tacgccagct ggcgaaaggg ggatgtgctg caaggcgatt aagttgggta acgccagggt    360
tttcccagtc acgacgttgt aaaacgacgg ccagtgccaa gctttgttta aaatataaca    420
aaattgtgat cccacaaaat gaagtggggc aaaatcaaat aattaactag tgtccgtaaa    480
cttgttggtc ttcaacttt tgaggaacac gttggacggc aaatcgtgac tataacacaa    540
gttgatttaa taattttagc caacacgtcg ggctgcgtgt tttttgcgct ctgtgtacac    600
gttgattaac tggtcgatta ataatttaa ttttggttc ttctttaaat ctgtgatgaa    660
attttttaaa ataactttaa attcttcatt ggtaaaaaat gccacgtttt gcaacttgtg    720
agggtctaat atgaggtcaa actcagtagg agttttatcc aaaaaagaaa acatgattac    780
gtctgtacac gaacgcgtat taacgcagag tgcaaagtat aagagggtta aaaaatatat    840
tttacggcac cataacgcat cgggttgata tcgttaatat ggatcaattt gaacagttga    900
ttaacgtgtc tctgctcaag tctttgatca aaacgcaaat cgacgaaaat gtgtcggaca    960
atatcaagtc gatgagcgaa aaactaaaaa ggctagaata cgacaatctc acagacagcg   1020
ttgagatata cggtattcac gacagcaggc tgaataataa aaaaattaga aactattatt   1080
taaccctaga aagataatca tattgtgacg tacgttaaag ataatcatgc gtaaaattga   1140
cgcatgtgtt tttatcggtc tgtatatcga ggtttattta ttaatttgaa tagatattaa   1200
gttttattat atttacactt acatactaat aataaattca acaaacaatt tatttatgtt   1260
tatttattta ttaaaaaaaa acaaaaaactc aaaatttctt ctaaagtaac aaaactttta   1320
aacattctct cttttacaaa aataaactta ttttgtactt taaaaacagt catgttgtat   1380
tataaaataa gtaattagct taacttatac ataatagaaa caaattatac ttattagtca   1440
gtccagaaac aactttggca catatcaata ttatgctctc gacaaataac tttttgcat    1500 tttttgcacg atgcatttgc ctttcgcctt attttagagg ggcagtaagt acagtaagta   1560
cgttttttca ttactggctc ttcagtactg tcatctgatg taccaggcac ttcatttggc   1620
aaaatattag agatattatc gcgcaaatat ctcttcaaag taggagcttc taaacggtta   1680
cgcataaacg atgacgtcag gctcatgtaa aggtttctca taaatttttt gcgactttga   1740
accttttctc ccttgctact gacattatgg ctgtatataa taaaagaatt tatgcaggca   1800
atgtttatca ttccgtacaa taatgccata ggccaccctat tcgtcttcct actgcaggtc   1860
atcacagaac acatttggtc tagcgtgtcc actccgcctt tagtttgatt ataatacata   1920
accatttgcg gttaccggt actttcgttg atagaagcat cctcatcaca agatgataat   1980
aagtatacca tcttagctgg cttcggttta tatgagacga gagtaagggg tccgtcaaaa   2040
caaaacatcg tgcacagggc ccccctcga gaaatttctc tggccgttat tcgttattct   2100 ctctttctt tttgggtctc tccctctctg cactaatgct ctctcactct gtcacacagt   2160
aaacggcata ctgctctcgt tggttcgaga gagcgcgcct cgaatgttcg cgaaaagagc   2220
gccggagtat aaatagaggc gctcgtctac cggagcgaca attcaattca aacaagcaaa   2280
gtgaacacgt cgctaagcga aagctaagca aataaacaag cgcagctgaa caagctaaac   2340
aatctgcagt aaagtgcaag ttaaagtgaa tcaattaaaa gtaaccagca accaagtaaa   2400
tcaactgcaa ctactgaaat ctgccaagaa gtaattattg aatacaagaa gagaactctg   2460
aatagggaat tgggaattag gtaccgaatt acacagaatg aattccggcg atcggatcaa   2520
taccgtgcgc ggtcctatca caatctctga agcgggtttc acactgactc acgagcacat   2580
```

```
ctgcggcagc tcggcaggat tcttgcgtgc ttggccagag ttcttcggta gccgcaaagc    2640
tctagcggaa aaggctgtga gaggattgcg ccgcgccaga gcggctggcg tgcgaacgat    2700
tgtcgatgtg tcgactttcg atatcggtcg cgacgtcagt ttattggccg aggtttcgcg    2760
ggctgccgac gttcatatcg tggcggcgac cggcttgtgg ttcgacccgc cactttcgat    2820
gcgattgagg agtgtagagg aactcacaca gttcttcctg cgtgagattc aatatggcat    2880
cgaagacacc ggaattaggg cgggcattat caaggtcgcg accacaggca aggcgacccc    2940
ctttcaggag ttagtgttaa aggcggccgc ccgggccagc ttggccaccg tgttccgtt     3000 aaccactcac acggcagcaa gtcagcgcga tggtgagcag caggccgcca ttttgagtc     3060 cgaaggcttg agcccctcac gggtttgtat tggtcacagc gatgatactg acgatttgag    3120
ctatctcacc gccctcgctg cgcgcggata cctcatcggt ctagaccaca tcccgcacag    3180
tgcgattggt ctagaagata tgcgagtgc atcagccctc ctgggcatcc gttcgtggca     3240
aacacgggct ctcttgatca aggcgctcat cgaccaaggc tacatgaaac aaatcctcgt    3300
ttcgaatgac tggctgttcg ggttttcgag ctatgtcacc aacatcatgg acgtgatgga    3360
tcgcgtgaac cccgacggga tggccttcat tccactgaga gtgatcccat tcctacgaga    3420
gaagggcgtc ccacaggaaa cgctggcagg catcactgtc actaacccgg cgcggttctt    3480
gtcaccgacc ttgcgggcgt catgacgcca tctggatcta aatggtttta tttgtacaca    3540
tttactttaa atttaataaa atttacttta gccgttgtcc gataattctt atatttaatt    3600
taaaccacct gcaagctttt aataaatcta tatgttcccg ggatctgaca atgttcagtg    3660
cagagactcg gctaccgctc gtggactttg aagttgacca acaatgttta ttcttacctc    3720
taatagtcct ctgtggcaag gtcaagattc tgttagaagc caatgaagaa cctggttgtt    3780
caataacatt ttgttcgtct aatatttcac tacgcttgac gttggctgac acttcatgta    3840
cctcatctat aaacgcttct tctgtatcgc tctggacgtc ttcacttacg tgatctgata    3900
tttcactgtc agaatcctca ccaacaagct cgtcatcgcc ttgcagaaga gcagagagga    3960
tatgctcatc gtctaaagaa catcccattt tattatatat tagtcacgat atctataaca    4020
agaaaatata tatataataa gttatcacgt aagtagaaca tgaaataaca atattaatta    4080
tcgtatgagt taaatcttaa aagtcacgta aaagataatc atgcgtcatt ttgactcacg    4140
cggtcgttat agttcaaaat cagtgacact taccgcattg acaagcacgc ctcagccgag    4200
ctccaagcgg cgactgagat gtcctaaatt gcaaacagcg acggattcgc gctatttaga    4260
aagagagagc aatatttcaa gaatgcatgc gtcaatttta cgcagactat ctttctaggg    4320
ttaaaaaaga tttgcgcttt actcgaccta aactttaaac acgtcataga atcttcgttt    4380
gacaaaaacc acattgtggc caagctgtgt gacgcgacgc gcgctaaaga atggcaaacc    4440
aagtcgcgcg agcgtcgact ctagaggatc cccgggtacc gagctcgaat tcgtaatcat    4500
ggtcatagct gtttcctgtg tgaaattgtt atccgctcac aattccacac aacatacgag    4560
ccggaagcat aaagtgtaaa gcctggggtg cctaatgagt gagctaactc acattaattg    4620
cgttgcgctc actgcccgct ttccagtcgg gaaacctgtc gtgccagctg cattaatgaa    4680
tcggccaacg cgcggggaga ggcggtttgc gtattgggcg ctcttccgct tcctcgctca    4740
ctgactcgct gcgctcggtc gttcggctgc ggcgagcggt atcagctcac tcaaaggcgg    4800
taatacggtt atccacagaa tcaggggata acgcaggaaa gaacatgtga gcaaaaggcc    4860
agcaaaaggc caggaaccgt aaaaaggccg cgttgctggc gtttttccat aggctccgcc    4920
```

-continued

```
cccctgacga gcatcacaaa aatcgacgct caagtcagag gtggcgaaac ccgacaggac      4980
tataaagata ccagccgttt ccccctggaa gctccctcgt gcgctctcct gttccgaccc      5040
tgccgcttac cggatacctg tccgcctttc tcccttcggg aagcgtggcg ctttctcaat      5100
gctcacgctg taggtatctc agttcggtgt aggtcgttcg ctccaagctg gctgtgtgc      5160 acgaaccccc cgttcagccc gaccgctgcg ccttatccgg taactatcgt cttgagtcca      5220
acccggtaag acacgactta tcgccactgg cagcagccac tggtaacagg attagcagag      5280
cgaggtatgt aggcggtgct acagagttct gaagtggtg gcctaactac ggctacacta      5340
gaaggacagt atttggtatc tgcgctctgc tgaagccagt taccttcgga aaaagagttg      5400
gtagctcttg atccggcaaa caaccaccg ctggtagcgg tggttttttt gtttgcaagc      5460
agcagattac gcgcagaaaa aaaggatctc aagaagatcc tttgatcttt tctacggggt      5520
ctgacgctca gtggaacgaa aactcacgtt aagggatttt ggtcatgaga ttatcaaaaa      5580
ggatcttcac ctagatcctt ttaaattaaa aatgaagttt taaatcaatc taagtatat      5640 atgagtaaac ttggtctgac agttaccaat gcttaatcag tgaggcacct atctcagcga      5700
tctgtctatt tcgttcatcc atagttgcct gactccccgt cgtgtagata actacgatac      5760
gggagggctt accatctggc cccagtgctg caatgatacc gcgagaccca cgctcaccgg      5820
ctccagattt atcagcaata aaccagccag ccggaagggc cgagcgcaga agtggtcctg      5880
caactttatc cgcctccatc cagtctatta attgttgccg ggaagctaga gtaagtagtt      5940
cgccagttaa tagtttgcgc aacgttgttg ccattgctac aggcatcgtg gtgtcacgct      6000
cgtcgtttgg tatggcttca ttcagctccg gttcccaacg atcaaggcga gttacatgat      6060
cccccatgtt gtgcaaaaaa gcggttagct ccttcggtcc tccgatcgtt gtcagaagta      6120
agttggccgc agtgttatca ctcatggtta tggcagcact gcataattct cttactgtca      6180
tgccatccgt aagatgcttt tctgtgactg gtgagtactc aaccaagtca ttctgagaat      6240
agtgtatgcg gcgaccgagt tgctcttgcc cggcgtcaat acgggataat accgcgccac      6300
atagcagaac tttaaaagtg ctcatcattg gaaaacgttc ttcggggcga aaactctcaa      6360
ggatcttacc gctgttgaga tccagttcga tgtaacccac tcgtgcaccc aactgatctt      6420
cagcatcttt tactttcacc agcgtttctg ggtgagcaaa aacaggaagg caaaatgccg      6480
caaaaaaggg aataagggcg cacggaaat gttgaatact catactcttc cttttcaat      6540 attattgaag catttatcag ggttattgtc tcatgagcgg atacatattt gaatgtattt      6600
agaaaaataa acaaataggg gttccgcgca catttccccg aaaagtgcca cctgacgtct      6660
aagaaaccat tattatcatg acattaacct ataaaaatag gcgtatcacg aggccctttc      6720
gtc                                                                   6723
```

<210> SEQ ID NO 14
<211> LENGTH: 6723
<212> TYPE: DNA
<213> ORGANISM: Artificial Sequence
<220> FEATURE:
<223> OTHER INFORMATION: Description of Artificial
      Sequence:piggyBac/opd

<400> SEQUENCE: 14

```
gacgaaaggg cctcgtgata cgcctatttt tataggttaa tgtcatgata ataatggttt       60
cttagacgtc aggtggcact tttcggggaa atgtgcgcgg aacccctatt tgtttatttt      120
tctaaataca ttcaaatatg tatccgctca tgagacaata accctgataa atgcttcaat      180
```

-continued

| | |
|---|---|
| aatattgaaa aaggaagagt atgagtattt caacatttcc gtgtcgcctt attcccttt | 240 |
| ttgcggcatt ttgccttcct gttttttgctc acccagaaac gctggtgaaa gtaaaagatg | 300 |
| ctgaagatca gttgggtgca cgagtgggtt acatcgaact ggatctcaac agcggtaaga | 360 |
| tccttgagag ttttcgcccc gaagaacgtt ttccaatgat gagcactttt aaagttctgc | 420 |
| tatgtggcgc ggtattatcc cgtattgacg ccgggcaaga gcaactcggt cgccgcatac | 480 |
| actattctca gaatgacttg gttgagtact caccagtcac agaaaagcat cttacggatg | 540 |
| gcatgacagt aagagaatta tgcagtgctg ccataaccat gagtgataac actgcggcca | 600 |
| acttacttct gacaacgatc ggaggaccga aggagctaac cgcttttttg cacaacatgg | 660 |
| gggatcatgt aactcgcctt gatcgttggg aaccggagct gaatgaagcc ataccaaacg | 720 |
| acgagcgtga caccacgatg cctgtagcaa tggcaacaac gttgcgcaaa ctattaactg | 780 |
| gcgaactact tactctagct tcccggcaac aattaataga ctggatggag gcggataaag | 840 |
| ttgcaggacc acttctgcgc tcggcccttc cggctggctg gtttattgct gataaatctg | 900 |
| gagccggtga gcgtgggtct cgcggtatca ttgcagcact ggggccagat ggtaagccct | 960 |
| cccgtatcgt agttatctac acgacgggga gtcaggcaac tatggatgaa cgaaatagac | 1020 |
| agatcgctga gataggtgcc tcactgatta agcattggta actgtacgac caagtttact | 1080 |
| catatatact ttagattgat ttaaaacttc attttaatt taaaaggatc taggtgaaga | 1140 |
| tcctttttga taatctcatg accaaaatcc cttaacgtga gttttcgttc cactgagcgt | 1200 |
| cagaccccgt agaaaagatc aaaggatctt cttgagatcc ttttttttctg cgcgtaatct | 1260 |
| gctgcttgca acaaaaaaa ccaccgctac cagcggtggt ttgtttgccg gatcaagagc | 1320 |
| taccaactct ttttccgaag gtaactggct tcagcagagc gcagatacca aatactgtcc | 1380 |
| ttctcatgta gccgtagtta ggccaccact tcaagaactc tgtagcaccg cctacatacc | 1440 |
| tcgctctgct aatcctgtta ccagtggctg ctgccagtgg cgataagtcg tgtcttaccg | 1500 |
| ggttggactc aagacgatag ttaccggata aggcgcagcg gtcgggctga acggggggtt | 1560 |
| cgtgcacaca gcccagcttg gagcgaacga cctaccacga actgagatac ctacagcgtg | 1620 |
| agcattgaga aagcgccacg cttcccgaag ggagaaaggc ggacaggtat ccggtaagcc | 1680 |
| gcagggtcgg aacaggagag cgcacgaggg agcttccagg gggaaacgcc tggtatcttt | 1740 |
| atagtcctgt cgggtttcgc cacctctgac ttgagcgtcg attttttgtga tgctcgtcag | 1800 |
| gggggcggag cctatggaaa aacgccagca acgcggcctt tttacggttc ctggccttt | 1860 |
| gctggccttt tgctcacatg ttctttcctg cgttatcccc tgattctgtg gataaccgta | 1920 |
| ttaccgcctt tgagtgagct gataccgctc gccgcagccg aacgaccgag cgcagcgagt | 1980 |
| cagtgagcga ggaagcggaa gagcgcccaa tacgcaaacc gcctctcccc gcgcgttggc | 2040 |
| cgattcatta atgcagctgg cacgacaggt ttcccgactg gaaagcgggc agtgagcgca | 2100 |
| acgcaattaa tgtgagttag ctcactcatt aggcacccca ggctttacac tttatgcttc | 2160 |
| cggctcgtat gttgtgtgga attgtgagcg gataacaatt tcacacagga aacagctatg | 2220 |
| accatgatta cgaattcgag ctcggtaccc ggggatcctc tagagtcgac gctcgcgcga | 2280 |
| cttggtttgc cattcttag cgcgcgtcgc gtcacacagc ttggccacaa tgtggttttt | 2340 |
| gtcaaacgaa gattctatga cgtgtttaaa gtttaggtcg agtaaagcgc aaatcttttt | 2400 |
| taaccctaga aagatagtct gcgtaaaatt gacgcatgca ttcttgaaat attgctctct | 2460 |
| cttttctaaat agcgcgaatc cgtcgctgtt tgcaatttag gacatctcag tcgccgcttg | 2520 |
| gagctcggct gaggcgtgct tgtcaatgcg gtaagtgtca ctgattttga actataacga | 2580 |

-continued

```
ccgcgtgagt caaaatgacg catgattatc ttttacgtga cttttaagat ttaactcata    2640
cgataattaa tattgttatt tcatgttcta cttacgtgat aacttattat atatatattt    2700
tcttgttata gatatcgtga ctaatatata ataaaatggg atgttcttta gacgatgagc    2760
atatcctctc tgctcttctg caaggcgatg acgagcttgt tggtgaggat tctgacagtg    2820
aaatatcaga tcacgtaagt gaagacgtcc agagcgatac agaagaagcg tttatagatg    2880
aggtacatga agtgtcagcc aacgtcaagc gtagtgaaat attagacgaa caaaatgtta    2940
ttgaacaacc aggttcttca ttggcttcta acagaatctt gaccttgcca cagaggacta    3000
ttagaggtaa gaataaacat tgttggtcaa cttcaaagtc cacgagcggt agccgagtct    3060
ctgcactgaa cattgtcaga tcccgggaac atatagattt attaaaagct tgcaggtggt    3120
ttaaattaaa tataagaatt atcggacaac ggctaaagta aattttatta aatttaaagt    3180
aaatgtgtac aaataaacca ttctagatcc agatggcgtc atgacgcccg caaggtcggt    3240
gacaagaacc gcgccgggtt agtcacagtg atgcctgcca gcgtttcctg tgggacgccc    3300
ttctctcgta ggaatgggat cactctcagt ggaatgaagg ccatcccgtc ggggttcacg    3360
cgatccatca cgtccatgat gttggtgaca tagctcgaaa acccgaacag ccagtcattc    3420
gaaacgagga tttgtttcat gtagccttgg tcgatgagcg ccttgatcaa gagagcccgt    3480
gtttgccacg aacggatgcc caggagggct gatgcactcg cattatcttc tagaccaatc    3540
gcactgtgcg ggatgtggtc tagaccgatg aggtatccgc gcgcagcgag ggcggtgaga    3600
tagctcaaat cgtcagtatc atcgctgtga ccaatacaaa cccgtgaggg gctcaagcct    3660
tcggactcaa aaatgcggc ctgctgctca ccatcgcgct gacttgctgc cgtgtgagtg    3720
gttaccggaa caccggtggc caagctggcc cgggcggccg cctttaacac taactcctga    3780
aaggggtcg ccttgcctgt ggtcgcgacc ttgataatgc ccgccctaat tccggtgtct    3840
tcgatgccat attgaatctc acgcaggaag aactgtgtga gttcctctac actcctcaat    3900
cgcatcgaaa gtggcgggtc gaaccacaag ccggtcgccg ccacgatatg aacgtcggca    3960
gcccgcgaaa cctcggccaa taaactgacg tcgcgaccga tatcgaaagt cgacacatcg    4020
acaatcgttc gcacgccagc cgctctggcg cggcgcaatc ctctcacagc cttttccgct    4080
agagctttgc ggctaccgaa gaactctggc caagcacgca agaatcctgc cgagctgccg    4140
cagatgtgct cgtgagtcag tgtgaaaccc gcttcagaga ttgtgatagg accgcgcacg    4200
gtattgatcc gatcgccgga attcattctg tgtaattcgg tacctaattc ccaattccct    4260
attcagagtt ctcttcttgt attcaataat tacttcttgg cagatttcag tagttgcagt    4320
tgatttactt ggttgctggt tactttaat tgattcactt taacttgcac tttactgcag    4380
attgtttagc ttgttcagct gcgcttgttt atttgcttag ctttcgctta gcgacgtgtt    4440
cactttgctt gtttgaattg aattgtcgct ccgtagacga agcgcctcta tttatactcc    4500
ggcgctcttt tcgcgaacat tcgaggcgcg ctctctcgaa ccaacgagag cagtatgccg    4560
tttactgtgt gacagagtga gagagcatta gtgcagagag ggagagaccc aaaaagaaaa    4620
gagagaataa cgaataacgg ccagagaaat ttctcgaggg ggggccctgt gcacgatgtt    4680
ttgttttgac ggacccctta ctctcgtctc atataaaccg aagccagcta agatggtata    4740
cttattatca tcttgtgatg aggatgcttc tatcaacgaa agtaccggta aaccgcaaat    4800
ggttatgtat tataatcaaa ctaaaggcgg agtggacacg ctagaccaaa tgtgttctgt    4860
gatgacctgc agtaggaaga cgaataggtg gcctatggca ttattgtacg gaatgataaa    4920
```

-continued

```
cattgcctgc ataaattctt ttattatata cagccatatt gtcagtagca agggagaaaa    4980
ggttcaaagt cgcaaaaaat ttatgagaaa cctttacatg agcctgacgt catcgtttat    5040
gcgtaaccgt ttagaagctc ctactttgaa gagatatttg cgcgataata tctctaatat    5100
tttgccaaat gaagtgcctg gtacatcaga tgacagtact gaagagccag taatgaaaaa    5160
acgtacttac tgtacttact gcccctctaa aataaggcga aaggcaaatg catcgtgcaa    5220
aaaatgcaaa aaagttattt gtcgagagca taatattgat atgtgccaaa gttgtttctg    5280
gactgactaa taagtataat ttgtttctat tatgtataag ttaagctaat tacttatttt    5340
ataatacaac atgactgttt ttaaagtaca aaataagttt atttttgtaa aagagagaat    5400
gtttaaaagt tttgttactt tagaagaaat tttgagtttt tgtttttttt taataaataa    5460
ataaacataa ataaattgtt tgttgaattt attattagta tgtaagtgta aatataataa    5520
aacttaatat ctattcaaat taataaataa acctcgatat acagaccgat aaaaacacat    5580
gcgtcaattt tacgcatgat tatctttaac gtacgtcaca atatgattat ctttctaggg    5640
ttaaataata gtttctaatt tttttattat tcagcctgct gtcgtgaata ccgtatatct    5700
caacgctgtc tgtgagattg tcgtattcta gccttttag tttttcgctc atcgacttga    5760
tattgtccga cacattttcg tcgatttgcg ttttgatcaa agacttgagc agagacacgt    5820
taatcaactg ttcaaattga tccatattaa cgatatcaac ccgatgcgta tatggtgcgt    5880
aaaatatatt ttttaaccct cttatacttt gcactctgcg ttaatacgcg ttcgtgtaca    5940
gacgtaatca tgttttcttt tttggataaa actcctactg agtttgacct catattagac    6000
cctcacaagt tgcaaaacgt ggcatttttt accaatgaag aatttaaagt tatttttaaa    6060
aatttcatca cagatttaaa gaagaaccaa aaattaaatt atttaatcga ccagttaatc    6120
aacgtgttac acagacgcaa aaaacacgca gcccgacgtg ttggctaaaa ttattaaatc    6180
aacttgtgtt atagtcacga tttgccgtcc aacgtgttcc tcaaaaagtt gaagaccaac    6240
aagtttacgg acactagtta attatttgat tttgccccac ttcattttgt gggatcacaa    6300
ttttgttata ttttaaacaa agcttggcac tggccgtcgt tttacaacgt cgtgactggg    6360
aaaaccctgg cgttacccaa cttaatcgcc ttgcagcaca tccccctttc gccagctggc    6420
gtaatagcga agaggcccgc accgatcgcc cttcccaaca gttgcgcagc ctgaatggcg    6480
aatggcgcct gatgcggtat tttctcctta cgcatctgtg cggtatttca caccgcatat    6540
ggtgcactct cagtacaatc tgctctgatg ccgcatagtt aagccagccc cgacacccgc    6600
caacacccgc tgacgcgccc tgacgggctt gtctgctccc ggcatccgct tacagacaag    6660
ctgtgaccgt ctccgggagc tgcatgtgtc agaggttttc accgtcatca ccgaaacgcg    6720
cga                                                                  6723
```

<210> SEQ ID NO 15
<211> LENGTH: 6448
<212> TYPE: DNA
<213> ORGANISM: Artificial Sequence
<220> FEATURE:
<223> OTHER INFORMATION: Description of Artificial Sequence:pcrII clone of piggyBac sequence

<400> SEQUENCE: 15

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
```

-continued

```
ttgtgagcga ataacaattt cacacaggaa acagctatga ccatgattac gccaagctat    240
ttaggtgaca ctatagaata ctcaagctat gcatcaagct tggtaccgag ctcggatcca    300
ctagtaacgg ccgccagtgt gctggaattc ggcttggatc ctctagaccc tagaaagata    360
gtctgcgtaa aattgacgca tgcattcttg aaatattgct ctctctttct aaatagcgcg    420
aatccgtcgc tgtttgcaat ttaggacatc tcagtcgccg cttggagctc ggctgaggcg    480
tgcttgtcaa tgcggtaagt gtcactgatt tgaactata acgaccgcgt gagtcaaaat    540
gacgcatgat tatcttttac gtgacttta agatttaact catacgataa ttaatattgt    600
tatttcatgt tctacttacg tgataactta ttatatatat attttcttgt tatagatatc    660
gtgactaata tataataaaa tgggatgttc tttagacgat gagcatatcc tctctgctct    720
tctgcaaggc gatgacgagc ttgttggtga ggattctgac agtgaaatat cagatcacgt    780
aagtgaagac gtccagagcg atacagaaga agcgtttata tgatgaggtac atgaagtgtc    840 agccaacgtc aagcgtagtg aaatattaga cgaacaaaat gttattgaac aaccaggttc    900
ttcattggct tctaacagaa tcttgacctt gccacagagg actattagag gtaagaataa    960
acattgttgg tcaacttcaa agtccacgag cggtagccga gtctctgcac tgaacattgt   1020
cagatctcaa agaggtccga cgcgtatgtg ccgcaatata tatgacccac ttttatgctt   1080
caaactattt tttactgatg agataatttc gcaaattgta aaatggacgg atgctgagat   1140
atcattgaaa cgtcgggaat ctatgacagg tgctacattt cgtgacacga atgaagatga   1200
aatctatgct ttctttggta ttctggtaat gacagcagtg agaaaagata accacatgtc   1260
cacagatgac ctcttggat cgatcttgt caatgtgtac gtctctgtaa tgagtctgtg   1320
gatcgttttg gattttttga tacgatgtct tagaatggat gacaaaagta tacggcccac   1380
acttcgagaa aacgatgtat ttactcctgt tagaaaaata tgggatctct ttatccatca   1440
gtgcatacaa aattacactc caggggctca tttgaccata tgaacagt tacttggttt    1500 tagaggacgg tgtccgttta ggatgtatat cccaaacaag ccaagtaagt atggaataaa   1560
aatcctcatg atgtgtgaca gtggtacgaa gtatatgata aatggaatgc ttatttggg    1620 aagaggaaca cagaccaacg gagtaccact cggtgaatac tacgtgaagg agttatcaaa   1680
gcctgtgcac ggtagttgtc gtaatattac gtgtgacaat tggttcacct caatcccttt   1740
ggcaaaaaac ttactacaag aaccgtataa gttaaccatt gtgggaaccg tgcgatcaaa   1800
caaacgcgag ataccggaag tactgaaaaa cagtcgctcc aggccagtgg gaacatcgat   1860
gttttgtttt gacggacccc ttactctcgt ctcatataaa ccgaagccag ctaagatggt   1920
atacttatta tcatccttgtg atgaggatgc ttctatcaac gaaagtaccg gtaaaccgca   1980
aatggttatg tattataatc aaactaaagg cggagtggac acgctagacc aaatgtgttc   2040
tgtgatgacc tgcagtagga agacgaatag gtggcctatg gcattattgt acggaatgat   2100
aaacattgcc tgcataaatt ctttttattat atacagccat aatgtcagta gcaagggaga   2160
aaaggttcaa agtcgcaaaa aatttatgag aaacctttac atgagcctga cgtcatcgtt   2220
tatgcgtaac cgtttagaag ctcctacttt gaagagatat ttgcgcgata atatctctaa   2280
tattttgcca aatgaagtgc gtggtacatg agatgacagt actgaagagc cagtaatgaa   2340
aaaacgtact tactgtactt actgcccctc taaaataagg cgaaaggcaa atgcatcgtg   2400
caaaaaatgc aaaaaagtta tttgtcgaga gcataatatt gatatgtgcc aaagttgttt   2460
ctggactgac taataagtat aatttgtttc tattatgtat aagttaagct aattacttat   2520
tttataatac aacatgactg tttttaaagt acaaaataag tttattttg taaaagagag   2580
```

```
aatgtttaaa agttttgtta ctttagaaga aattttgagt ttttgttttt ttttaataaa      2640
taaataaaca taaataaatt gtttgttgaa tttattatta gtatgtaagt gtaaatataa      2700
taaaacttaa tatctattca aattaataaa taaacctcga tatacagacc gataaaaaca      2760
catgcgtcaa ttttacgcat gattatcttt aacgtacgtc acaatatgat tatctttcta      2820
gggggatcct ctagaaagcc gaattctgca gatatccatc acactggcgg ccgctcgagc      2880
atgcatctag agggcccaat tcgccctata gtgagtcgta ttacaattca ctggccgtcg      2940
ttttacaacg tcgtgactgg gaaaaccctg gcgttaccca acttaatcgc cttgcagcac      3000
atcccccttt cgccagctgg cgtaatagcg aagaggcccg caccgatcgc ccttcccaac      3060
agttgcgcag cctgaatggc gaatgggacg cgccctgtag cggcgcatta agcgcggcgg      3120
gtgtggtggt tacgcgcagc gtgaccgcta cacttgccag cgccctagcg cccgctcctt      3180
tcgctttctt cccttccttt ctcgccacgt tcgccggctt tccccgtcaa gctctaaatc      3240
gggggctccc tttagggttc cgatttagag ctttacggca cctcgaccgc aaaaaacttg      3300
atttgggtga tggttcacgt agtgggccat cgccctgata cacggttttt cgccctttga      3360
cgttggagtc cacgttcttt aatagtggac tcttgttcca aactggaaca acactcaacc      3420
ctatcgcggt ctattctttt gatttataag gattttgcc gatttcggcc tattggttaa       3480
aaaatgagct gatttaacaa attcagggcg caagggctgc taaggaacc ggaacacgta       3540 gaaagccagt ccgcagaaac ggtgctgacc ccggatgaat gtcagctact gggctatctg      3600
gacaagggaa aacgcaagcg caaagagaaa gcaggtagct tgcagtgggc ttacatggcg      3660
atagctagac tgggcggttt tatggacagc aagcgaaccg gaattgccag ctggggcgcc      3720
ctctggtaag gttgggaagc cctgcaaagt aaactggatg gctttcttgc cgccaaggat      3780 ctgatgcgc aggggatcaa gatctgatca agagacagga tgaggatcgt ttcgcatgat       3840
tgaacaagat ggattgcacg caggttctcc ggccgcttgg gtggagaggc tattcggcta      3900
tgactgggca acaacagacaa tcggctgctc tgatgccgcc gtgttccggc tgtcagcgca    3960
ggggcgcccg gttcttttg tcaagaccga cctgtccggt gccctgaatg aactgcagga      4020
cgaggcagcg cggctatcgt ggctggccac gacgggcgtt ccttgcgcag ctgtgctcga      4080
cgttgtcact gaagcgggaa gggactggct gctattgggc gaagtgccgg ggcaggatct      4140
cctgtcatct cgccttgctc ctgccgagaa agtatccatc atggctgatg caatgcggcg      4200
gctgcatacg cttgatccgg ctacctgccc attcgaccac caagcgaaac atcgcatcga      4260
gcgagcacgt actcggatgg aagccggtct tgtcgatcag gatgatctgg acgaagagca      4320 tcagggctc gcgccagccg aactgttcgc caggctcaag gcgcgcatgc ccgacggcga       4380
ggatctcgtc gtgatccatg gcgatgcctg cttgccgaat atcatggtgg aaaatggccg      4440
cttttctgga ttcaacgact gtggccggct gggtgtggcg accgctctc aggacatagc       4500 gttggatacc cgtgatattg ctgaagagct tggcggcgaa tgggctgacc gcttcctcgt      4560
gctttacggt atcgccgctc ccgattcgca gcgcatcgcc ttctatcgcc ttcttgacga      4620
gttcttctga attgaaaaag gaagagtatg agtattcaac atttccgtgt cgcccttatt      4680
cccttttttg cggcattttg ccttcctgtt tttgctcacc cagaaacgct ggtgaaagta      4740
aaagatgctg aagatcagtt gggtgcacga gtgggttaca tcgaactgga tctcaacagc      4800
ggtaagatcc ttgagagttt tcgccccgaa gaacgttttc caatgatgag cacttttaaa      4860
gttctgctat gtgatacact attatcccgt attgacgccg ggcaagagca actcggtcgc      4920
```

-continued

```
cgcatacact attctcagaa tgacttggtt gagtactcac cagtcacaga aaagcatctt      4980
acggatggca tgacagtaag agaattatgc agtgctgcca taaccatgag tgataacact      5040
gcggccaact tacttctgac aacgatcgga ggaccgaagg agctaaccgc ttttttgcac      5100
aacatggggg atcatgtaac tcgccttgat cgttgggaac cggagctgaa tgaagccata      5160
ccaaacgacg agagtgacac cacgatgcct gtagcaatgc caacaacgtt gcgcaaacta      5220
ttaactggcg aactacttac tctagcttcc cggcaacaat aatagactg aatggaggcg       5280 gataaagttg caggaccact tctgcgctcg gcccttccgg ctggctggtt tattgctgat      5340
aaatctggag ccggtgagcg tgggtctcgc ggtatcattg cagcactggg gccagatggt      5400
aagcgctccc gtatcgtagt tatctacacg acggggagtc aggcaactat ggatgaacga      5460
aatagacaga tcgctgagat aggtgcctca ctgattaagc attggtaact gtcagaccaa      5520
gtttactcat atatacttta gattgattta aaacttcatt tttaatttaa aaggatctag      5580
gtgaagatcc ttttgataa tctcatgacc aaaatccctt aacgtgagtt tcgttccac       5640 tgagcgtcag accccgtaga aaagatcaaa ggatcttctt gagatccttt ttttctgcgc      5700
gtaatctgct gcttgcaaac aaaaaaacca ccgctaccag cggtggtttg tttgccggat      5760
caagagctac caactctttt tccgaaggta actggcttca gcagagcgca gataccaaat      5820
actgtccttc tagtgtagcc gtagttaggc caccacttca agaactctgt agcaccgcct      5880
acatacctcg ctctgctaat cctgttacca gtggctgctg ccagtggcga taagtcgtgt      5940
cttaccgggt tggactcaag acgatagtta ccggataagg cgcagcggtc gggctgaacg      6000
gggggttcgt gcacacagcc cagcttggag cgaacgacct acaccgaact gagatacctta    6060 cagcgtgagc tatgagaaag cgccacgctt cccgaaggga gaaaggcgga caggtatccg     6120
gtaagcggca gggtcggaac aggagagcgc acgagggagc ttccagggg aaacgcctgg      6180 tatctttata gtcctgtcgg gtttcgccac ctctgacttg agcgtcgatt tttgtgatgc      6240
tcgtcagggg ggcggagcct atgaaaaac gccagcaacg cggccttttt acggttcctg      6300
ggcttttgct ggccttttgc tcacatgttc tttcctgcgt tatcccctga ttctgtggat      6360
aaccgtatta ccgcctttga gtgagctgat accgctcgcc gcagccgaac gaccgagcgc     6420
agcgagtcag tgagcgagga agcggaag                                        6448
```

<210> SEQ ID NO 16
<211> LENGTH: 5194
<212> TYPE: DNA
<213> ORGANISM: Artificial Sequence
<220> FEATURE:
<223> OTHER INFORMATION: Description of Artificial Sequence:plasmid IFP2B/Xpuc18.1

<400> SEQUENCE: 16

```
tcgcgcgttt cggtgatgac ggtgaaaacc tctgacacat gcagctcccg gagacggtca       60
cagcttgtct gtaagcggat gccgggagca gacaagcccg tcaggcgcg tcagcgggtg       120 ttggcgggtg tcgggctgg cttaactatg cggcatcaga gcagattgta ctgagagtgc       180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgccaa gcttgcatgc ctgcaggtcg      420
actctagagg gatccctag attaacccta gaaagatagt ctgcgtaaaa ttgacgcatg      480
```

-continued

| | |
|---|---|
| cattcttgaa atattgctct ctctttctaa atagcgcgaa tccgtcgctg tttgcaattt | 540 |
| aggacatctc agtcgccgct tggagctcgg ctgaggcgtg cttgtcaatg cggtaagtgt | 600 |
| cactgatttt gaactataac gaccgcgtga gtcaaaatga cgcatgatta tcttttacgt | 660 |
| gacttttaag atttaactca tacgataatt aatattgtta tttcatgttc tacttacgtg | 720 |
| ataacttatt atatatatat tttcttgtta tagatatcgt gactaatata taataaaatg | 780 |
| ggatgttctt tagacgatga gcatatcctc tctgctcttc tgcaaggcga tgacgagctt | 840 |
| gttggtgagg attctgacag tgaaatatca gatcacgtaa gtgaagacgt ccagagcgat | 900 |
| acagaagaag cgtttataga tgaggtacat gaagtgtcag ccaacgtcaa gcgtagtgaa | 960 |
| atattagacg aacaaaatgt tattgaacaa ccaggttctt cattggcttc taacagaatc | 1020 |
| ttgaccttgc cacagaggac tattagaggt aagaataaac attgttggtc aacttcaaag | 1080 |
| tccacgagcc gtagccgagt ctctgcactg aacattgtca gatctcaaag aggtccgacg | 1140 |
| cgtatgtgcc gcaatatata tgacccactt ttatgcttca aactatttt tactgatgag | 1200 |
| ataatttcgc aaattgtaaa atggacaaat gctgagatat cattgaaacg tcggaatct | 1260 |
| atgacaggtg ctacatttcg tgacacgaat gaagatgaaa tctatgcttt ctttggtatt | 1320 |
| ctggtaatga cagcagtgag aaaagataac cacatgtcca cagatgacct ctttggatcg | 1380 |
| atctttgtca atgtgtacgt ctctgtaatg agtctgtgga tcgttttgga ttttttgata | 1440 |
| cgatgtctta gaatggatga caaaagtata cggcccacac ttcgagaaaa cgatgtattt | 1500 |
| actcctgtta gaaaaatatg ggatctcttt atccatcagt gcatacaaaa ttacactcca | 1560 |
| ggggctcatt tgaccataga tgaacagtta cttggtttta gaggacggtg tccgtttagg | 1620 |
| atgtatatcc caaacaagcc aagtaagtat ggaataaaaa tcctcatgat gtgtgacagt | 1680 |
| ggtacgaagt atatgataaa tggaatgcct tatttgggaa gaggaacaca gaccaacgga | 1740 |
| gtaccactcg gtgaatacta cgtgaaggag ttatcaaagc ctgtgcacgg tagttgtcgt | 1800 |
| aatattacgt gtgacaattg gttcacctca atccctttgg caaaaaactt actacaagaa | 1860 |
| ccgtataagt taaccattgt gggaaccgtg cgatcaaaca aacgcgagat accggaagta | 1920 |
| ctgaaaaaca gtcgctccag gccagtggga acatcgatgt tttgttttga cggacccctt | 1980 |
| actctcgtct catataaacc gaagccagct aagatggtat acttattatc atcttgtgat | 2040 |
| gaggatgctt ctatcaacga aagtaccggt aaaccgcaaa tggttatgta ttataatcaa | 2100 |
| actaaaggcg gagtggacac gctagaccaa atgtgttctg tgatgacctg cagtaggaag | 2160 |
| acgaataggt ggcctatggc attattgtac ggaatgataa acattgcctg cataaattct | 2220 |
| tttattatat acagccataa tgtcagtagc aagggagaaa aggttcaaag tcgcaaaaaa | 2280 |
| tttatgagaa acctttacat gagcctgacg tcatcgttta tgcgtaaccg tttagaagct | 2340 |
| cctactttga agagatattt gcgcgataat atctctaata ttttgccaaa tgaagtgcct | 2400 |
| ggtacatcag atgacagtac tgaagagcca gtaatgaaaa aacgtactta ctgtacttac | 2460 |
| tgcccctcta aaataaggcg aaaggcaaat gcatcgtgca aaaatgcaa aaagttatt | 2520 |
| tgtcgagagc ataatattga tatgtgccaa agttgtttct ggactgacta ataagtataa | 2580 |
| tttgtttcta ttatgtataa gttaagctaa ttacttattt tataatacaa catgactgtt | 2640 |
| tttaaagtac aaaataagtt tattttgta aagagagaa tgtttaaaag ttttgttact | 2700 |
| ttagaagaaa ttttgagttt ttgttttttt ttaataaaata aataaacata aataaattgt | 2760 |
| ttgttgaatt tattattagt atgtaagtgt aaatataata aaacttaata tctattcaaa | 2820 |
| ttaataaata aacctcgata tacagaccga taaaaacaca tgcgtcaatt ttacgcatga | 2880 |

-continued

```
ttatctttaa cgtacgtcac aatatgatta tctttctagg gttaatctag aggatccgat   2940
ccccgggtac cgagctcgaa ttcgtaatca tggtcatagc tgtttcctgt gtgaaattgt   3000
tatccgctca caattccaca acaatacga gccggaagca taaagtgtaa agcctggggt   3060
gcctaatgag tgagctaact cacattaatt gcgttgcgct cactgcccgc tttccagtcg   3120
ggaaacctgt cgtgccagct gcattaatga atcggccaac gcgcggggag aggcggtttg   3180
cgtattgggc gctcttccgc ttcctcgctc actgactcgc tgcgctcggt cgttcggctg   3240
cggcgagcgg tatcagctca ctcaaaggcg gtaattcggt tatccacaga atcagggggat   3300
aacgcaggaa agaacatgtg agcaaaaggc cagcaaaagg ccaggaaccg taaaaaggcc   3360
gcgttgctgg cgttttccca taggctccgc cccctgacg agcatcacaa aaatcgacgc   3420
tcaagtcaga ggtggcgaaa cccgacagga ctataaagat accaggcgtt ccccctggaa   3480
agctccctcg tgcgctctcc tgttccgacc ctgccgctta ccggatacct gtccgccttt   3540
ctcccttcgg gaagcgtggc gctttctcaa tgctcacgct gtaggtatct cagttcggtg   3600
taggtcgttc gctccaagct gggctgtgtg cacgaacccc ccgttcagcc cgaccgctgc   3660
gccttatccg gtaactatcg tcttgagtcc aacccggtaa gacacgactt atcgccactg   3720
gcagcagcca ctggtaacag gattagcaga gcgaggtatg taggcggtgc tacagagttc   3780
ttgaagtggt ggcctaacta cggctacact agaaggacag tatttggtat ctgcgctctg   3840
ctgaagccag ttaccttcgg aaaaagagtt ggtagctctt gatccggcaa acaaaccacc   3900
gctggtagcg gtggtttttt tgtttgcaag cagcagatta cgcgcagaaa aaaggatct   3960
caagaagatc ctttgatctt ttctacgggg tctgacgctc agtggaacga aaactcacgt   4020
taagggattt tggtcatgag attatcaaaa aggatcttca cctagatcct tttaaattaa   4080
aaatgaagtt ttaaatcaat ctaaagtata tatgagtaaa cttggtctga cagttaccaa   4140
tgcttaatca gtgaggcacc tatctcagcg atctgtctat ttcgttcatc catagttgcc   4200
tgactccccg tcgtgtagat aactacgata cgggagggct taccatctgg ccccagtgct   4260
gcaatgatac cgcgagaccc acgctcaccg gctccagatt tatcagcaat aaaccagcca   4320
gccggaaggg ccgagcgcag aagtggtcct gcaactttat ccgcctccat ccagtctatt   4380
aattgttgcc gggaagctag agtaagtagt tcgccagtta atagtttgcg caacgttgtt   4440
gccattgcta caggcatcgt ggtgtcacgc tcgtcgtttg gtatggcttc attcagctcc   4500
ggttcccaac gatcaaggcg agttacatga tcccccatgt tgtgcaaaaa agcggttagc   4560
tccttcggtc ctccgatcgt tgtcagaagt aagttggccg cagtgttatc actcatggtt   4620
atggcagcac tgcataattc tcttactgtc atgccatccg taagatgctt ttctgtgact   4680
ggtgagtact caaccaagtc attctgagaa tagtgtatgc ggcgaccgag ttgctcttgc   4740
ccggcgtcaa tacgggataa taccgcgcca catagcagaa ctttaaaagt gctcatcatt   4800
ggaaaacgtt cttcggggcg aaaactctca aggatcttac cgctgttgag atccagttcg   4860
atgtaaccca ctcgtgcacc caactgatct tcagcatctt ttactttcac cagcgtttct   4920
gggtgagcaa aaacaggaag gcaaatgcc gcaaaaaagg gaataagggc gacacggaaa   4980
tattgattac tcatactctt ccttttcaa tattattgaa gcatttatca gggttattgt   5040
ctcatgagcg gatacatatt tgaatgtatt tagaaaaata acaaataggg gttccgcgc   5100
acatttcccc gaaaagtgcc acctgacgtc taagaaacca ttattatcat gacattaacc   5160
tataaaaata ggcgtatcac gaggcccttt cgtc                              5194
```

<210> SEQ ID NO 17
<211> LENGTH: 5194
<212> TYPE: DNA
<213> ORGANISM: Artificial Sequence
<220> FEATURE:
<223> OTHER INFORMATION: Description of Artificial Sequence:plasmid IFP2B/XsupF4H

<400> SEQUENCE: 17

| | | | | | |
|---|---|---|---|---|---|
| gacgaaaggg | cctcgtgata | cgcctatttt | tataggttaa | tgtcatgata | ataatggttt | 60 |
| cttagacgtc | aggtggcact | tttcggggaa | atgtgcgcgg | aacccctatt | tgtttatttt | 120 |
| tctaaataca | ttcaaatatg | tatccgctca | tgagacaata | accctgataa | atgcttcaat | 180 |
| aatattgaaa | aaggaagagt | atgagtattc | aacatttccg | tgtcgccctt | attccctttt | 240 |
| ttgcggcatt | ttgccttcct | gtttttgctc | acccagaaac | gctggtgaaa | gtaaaagatg | 300 |
| ctgaagatca | gttgggtgca | cgagtgggtt | acatcgaact | ggatctcaac | agcggtaaga | 360 |
| tccttgagag | ttttcgcccc | gaagaacgtt | ttccaatgat | gagcactttt | aaagttctgc | 420 |
| tatgtggcgc | ggtattatcc | cgtattgacg | ccgggcaaga | gcaactcggt | cgccgcatac | 480 |
| actattctca | gaatgacttg | gttgagtact | caccagtcac | agaaaagcat | cttacggatg | 540 |
| gcatgacagt | aagagaatta | tgcagtgctg | ccataaccat | gagtgataac | actgcggcca | 600 |
| acttacttct | gacaacgatc | ggaggaccga | aggagctaac | cgcttttttg | cacaacatgg | 660 |
| gggatcatgt | aactcgcctt | gatcgttggg | aaccggagct | gaatgaagcc | ataccaaacg | 720 |
| acgagcgtga | caccacgatg | cctgtagcaa | tggcaacaac | gttgcgcaaa | ctattaactg | 780 |
| gcgaactact | tactctagct | tcccggcaac | aattaataga | ctggatggag | gcggataaag | 840 |
| ttgcaggacc | acttctgcgc | tcggcccttc | cggctggctg | gtttattgct | gataaatctg | 900 |
| gagccggtga | gcgtgggtct | cgcggtatca | ttgcagcact | ggggccagat | ggtaagccct | 960 |
| cccgtatcgt | agttatctac | acgacgggga | gtcaggcaac | tatggatgaa | cgaaatagac | 1020 |
| agatcgctga | gataggtgcc | tcactgatta | agcattggta | actgtcagac | caagtttact | 1080 |
| catatatact | ttagattgat | ttaaaacttc | attttaatt | taaaaggatc | taggtgaaga | 1140 |
| tcctttttga | taatctcatg | accaaaatcc | cttaacgtga | gttttcgttc | cactgagcgt | 1200 |
| cagaccccgt | agaaaagatc | aaaggatctt | cttgagatcc | tttttttctg | cgcgtaatct | 1260 |
| gctgcttgca | aacaaaaaaa | ccaccgctac | cagcggtgtt | tgtttgccg | gatcaagagc | 1320 |
| taccaactct | ttttccgaag | gtaactggct | tcagcagagc | gcagatacca | aatactgtcc | 1380 |
| ttctagtgta | gccgtagtta | ggccaccact | tcaagaactc | tgtagcaccg | cctacatacc | 1440 |
| tcgctctgct | aatcctgtta | ccagtggctg | ctgccagtgg | cgataagtcg | tgtcttaccg | 1500 |
| ggttggactc | aagacgatag | ttaccggata | aggcgcagcg | gtcgggctga | acggggggtt | 1560 |
| cgtgcacaca | gcccagcttg | gagcgaacga | cctacaccga | actgagatac | ctacagcgtg | 1620 |
| agcattgaga | aagcgccacg | cttcccgaag | ggagaaaggc | ggacaggtat | ccggtaagcg | 1680 |
| gcagggtcgg | aacaggagag | cgcacgaggg | agcttccagg | gggaaacgcc | tggtatcttt | 1740 |
| atagtcctgt | cgggtttcgc | cacctctgac | ttgagcgtcg | atttttgtga | tgctcgtcag | 1800 |
| gggggcggag | cctatggaaa | aacgccagca | acgcggcctt | tttacggttc | ctggcctttt | 1860 |
| gctggccttt | tgctcacatg | ttctttcctg | cgttatcccc | tgattctgtg | gataaccgta | 1920 |
| ttaccgcctt | tgagtgagct | gataccgctc | gccgcagccg | aacgaccgag | cgcagcgagt | 1980 |
| cagtgagcga | ggaagcggaa | gagcgcccaa | tacgcaaacc | gcctctcccc | gcgcgttggc | 2040 |

-continued

```
cgattcatta atgcagctgg cacgacaggt ttcccgactg gaaagcgggc agtgagcgca      2100
acgcaattaa tgtgagttag ctcactcatt aggcacccca ggctttacac tttatgcttc      2160
cggctcgtat gttgtgtgga attgtgagcg gataacaatt tcacacagga aacagctatg      2220
accatgatta cgaattcgag ctcggtaccc ggggatcgga tcctctagat taaccctaga      2280
aagatagtct gcgtaaaatt gacgcatgca ttcttgaaat attgctctct ctttctaaat      2340
agcgcgaatc cgtcgctgtt tgcaatttag gacatctcag tcgccgcttg gagctcggct      2400
gaggcgtgct tgtcaatgcg gtaagtgtca ctgattttga actataacga ccgcgtgagt      2460
caaaatgacg catgattatc ttttacgtga cttttaagat ttaactcata cgataattaa      2520
tattgttatt tcatgttcta cttacgtgat aacttattat atatatattt tcttgttata      2580
gatatcgtga ctaatatata ataaaatggg atgttcttta gacgatgagc atatcctctc      2640
tgctcttctg caaggcgatg acgagcttgt tggtgaggat tctgacagtg aaatatcaga      2700
tcacgtaagt gaagacgtcc agagcgatac agaagaagcg tttatagatg aggtacatga      2760
agtgtcagcc aacgtcaagc gtagtgaaat attagacgaa caaatgttat ttgaacaacc      2820
aggttcttca ttggcttcta acagaatctt gaccttgcca cagaggacta ttagaggtaa      2880
gaataaacat tgttggtcaa cttcaaagtc cacgagcggt agccgagtct ctgcactgaa      2940
cattgtcaga tctcaaagag gtccgacgcg tatgtgccgc aatatatatg acccactttt      3000
atgcttcaaa ctatttttta ctgatgagat aatttcgcaa attgtaaaat ggacaaatgc      3060
tgagatatca ttgaaacgtc gggaatctat gacaggtgct acatttcgtg acacgaatga      3120
agatgaaatc tatgctttct ttggtattct ggtaatgaca gcagtgagaa aagataacca      3180
catgtccaca gatgacctct ttggatcgat cttttgtcaat gtgtacgtct ctgtaatgag      3240
tctgtggatc gttttggatt ttttgatacg atgtcttaga atggatgaca aaagtatacg      3300
gcccacactt cgagaaaacg atgtatttac tcctgttaga aaaatatggg atctcttttat      3360 ccatcagtgc atacaaaatt acactccagg ggctcatttg accatagatg aacagttact      3420
tggttttaga ggacggtgtc cgtttaggat gtatatccca aacaagccaa gtaagtatgg      3480
aataaaaatc ctcatgatgt gtgacagtgg tacgaagtat atgataaatg gaatgcctta      3540
tttgggaaga ggaacacaga ccaacggagt accactcggt gaatactacg tgaaggagtt      3600
atcaaagcct gtgcacggta gttgtcgtaa tattacgtgt gacaattggt tcacctcaat      3660
ccctttggca aaaaacttac tacaagaacc gtataagtta accattgtgg gaaccgtgcg      3720
atcaaacaaa cgcgagatac cggaagtact gaaaaacagt cgctccaggc cagtgggaac      3780
atcgatgttt tgttttgacg gaccccttac tctcgtctca tataaaccga agccagctaa      3840
gatggtatac ttattatcat cttgtgatga ggatgcttct atcaacgaaa gtaccggtaa      3900
accgcaaatg gttatgtatt ataatcaaac taaaggcgga gtggacacgc tagaccaaat      3960
gtgttctgtg atgacctgca gtaggaagac gaataggtgg cctatggcat tattgtacgg      4020
aatgataaac attgcctgca taattctttt tattatatac agccataatg tcagtagcaa      4080
gggagaaaag gttcaaagtc gcaaaaaatt tatgagaaac ctttacatga gcctgacgtc      4140
atcgtttatg cgtaaccgtt tagaagctcc tactttgaag agatatttgc gcgataaatat      4200 ctctaatatt ttgccaaatg aagtgcctgg tacatcagat gacagtactg aagagccagt      4260
aatgaaaaaa cgtacttact gtacttactg cccctctaaa ataaggcgaa aggcaaatgc      4320
atcgtgcaaa aaatgcaaaa aagttatttg tcgagagcat aatattgata tgtgccaaag      4380
ttgtttctgg actgactaat aagtataatt tgtttctatt atgtataagt taagctaatt      4440
```

```
acttatttta taatacaaca tgactgtttt taaagtacaa aataagttta tttttgtaaa    4500
agagagaatg tttaaaagtt ttgttacttt agaagaaatt ttgagttttt gttttttttt    4560
aataaataaa taaacataaa taaattgttt gttgaattta ttattagtat gtaagtgtaa    4620 atataaataaa acttaatatc tattcaaatt aataaataaa cctcgatata cagaccgata   4680
aaaacacatg cgtcaatttt acgcatgatt atctttaacg tacgtcacaa tatgattatc    4740
tttctagggt taatctagag gatccctcta gagtcgacct gcaggcatgc aagcttggca    4800
ctggccgtcg ttttacaacg tcgtgactgg gaaaaccctg gcgttaccca acttaatcgc    4860
cttgcagcac atccccctttt cgccagctgg cgtaatagcg aagaggcccg caccgatcgc   4920
ccttcccaac agttgcgcag cctgaatggc gaatggcgcc tgatgcggta ttttctcctt    4980
acgcatctgt gcggtatttc acaccgcata tggtgcactc tcagtacaat ctgctctgat    5040
gccgcatagt taagccagcc ccgacacccg ccaacacccg ctgacgcgcc ctgacgggct    5100
tgtctgctcc cggcatccgc ttacagacaa gctgtgaccg tctccgggag ctgcatgtgt    5160
cagaggtttt caccgtcatc accgaaacgc gcga                                5194
```

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence:hsp/opd
      new-for

<400> SEQUENCE: 18

```
gaagatctat ttctctggcc gttattcgtt at                                   32
```

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence:hsp/opd
      nwe-rev

<400> SEQUENCE: 19

```
gaagatctga tcccgggaac atatagattt at                                   32
```

<210> SEQ ID NO 20
<211> LENGTH: 7560
<212> TYPE: DNA
<213> ORGANISM: Artificial Sequence
<220> FEATURE:
<223> OTHER INFORMATION: Description of Artificial Sequence:p3E1.2hs/opd

<400> SEQUENCE: 20

```
ttaaccctag aaagatagtc tgcgtaaaat tgacgcatgc attcttgaaa tattgctctc      60
tctttctaaa tagcgcgaat ccgtcgctgt ttgcaattta ggacatctca gtcgccgctt     120
ggagctcggc tgaggcgtgc ttgtcaatgc ggtaagtgtc actgattttg aactataacg     180
accgcgtgag tcaaaatgac gcatgattat cttttacgtg acttttaaga tttaactcat     240
acgataatta atattgttat ttcatgttct acttacgtga taacttatta tatatatatt     300
ttcttgttat agatatcgtg actaatatat aataaaatgg gatgttcttt agacgatgag    360
catatcctct ctgctcttct gcaaggcgat gacgagcttg ttggtgagga ttctgacagt    420
gaaatatcag atcacgtaag tgaagacgtc cagagcgata cagaagaagc gtttatagat    480
```

```
gaggtacatg aagtgtcagc caacgtcaag cgtagtgaaa tattagacga acaaaatgtt    540
attgaacaac caggttcttc attggcttct aacagaatct tgaccttgcc acagaggact    600
attagaggta agaataaaca ttgttggtca acttcaaagt ccacgagcgg tagccgagtc    660
tctgcactga acattgtcag atctgcgtct cgagaaattt ctctggccgt tattcgttat    720
tctctctttt cttttgggt ctctccctct ctgcactaat gctctctcac tctgtctcac     780
agtaaacggc atactgctct cgttggttcg agagagcgcg cctcgaatgt tcgcgaaaag    840
agcgccggag tataaataga ggcgcttcgt ctacggagcg acaattcaat tcaaacaagc    900
aaagtgaaca cgtcgctaag cgaaagctaa gcaaataaac aagcgcagct gaacaagcta    960
aacaatctgc agtaaagtgc aagttaaagt gaatcaatta aaagtaacca gcaaccaagt   1020
aaatcaactg caactactga atctgccaa gaagtaatta ttgaatacaa gaagagaact    1080
ctgaataggg aattgggaat taggtaccga attacacaga atgaattccg gcgatcggat   1140
caataccgtg cgcggtccta tcacaatctc tgaagcgggt ttcacactga ctcacgagca   1200
catctgcggc agctcggcag gattcttgcg tgcttggcca gagttcttcg gtagccgcaa   1260
agctctagcg gaaaaggctg tgagaggatt gcgccgcgcc agagcggctg gcgtgcgaac   1320
gattgtcgat gtgtcgactt tcgatatcgg tcgcgacgtg agtttattgg ccgaggtttc   1380
gcgggctgcc gacgttcata tcgtggcggc gaccggcttg tggttcgacc cgccactttc   1440
gatgcgattg aggagtgtag aggaactcac acagttcttc ctgcgtgaga ttcaatatgg   1500
catcgaagac accggaatta gggcgggcat tatcaaggtc gcgaccacag gcaaggcgac   1560
cccctttcag gagttagtgt taaaggcggc cgcccgggcc agcttggcca ccggtgttcc   1620
ggtaaccact cacacggcag caagtcagcg cgatggtgag cagcaggccg ccattttga    1680
gtccgaaggc ttgagcccct cacgggtttg tattggtcac agcgatgata ctgacgattt   1740
gagctatctc accgccctcg ctgcgcgcgg atacctcatc ggtctagacc acatcccgca   1800
cagtgcgatt ggtctagaag ataatgcgag tgcatcagcc ctcctgggca tccgttcgtg   1860
gcaaacacgg gctctcttga tcaaggcgct catcgaccaa ggctacatga aacaaatcct   1920
cgtttcgaat gactggctgt tcgggttttc gagctatgtc accaacatca tggacgtgat   1980
ggatcgcgtg aaccccgacg ggatggcctt cattccactg agagtgatcc cattcctacg   2040
agagaagggc gtcccacagg aaacgctggc aggcatcact gtgactaacc cggcgcggtt   2100
cttgtcaccg accttgcggg cgtcatgacg ccatctggat ctagaatggt ttatttgtac   2160
acatttactt taaatttaat aaaatttact ttagccgttg tccgataatt cttatattta   2220
atttaaacca cctgcaagct tttaataaat ctatatgttc ccgggtacca cacgcgagat   2280
ctcaaagagg tccgacgcgt atgtgccgca atataatatg cccacttttt atgcttcaac   2340
tatttttttac tgatgagata atttcgcaaa ttgtaaaatg acaaatgct gagatatcat    2400
tgaaacgtcg ggaatctatg acaggtgcta catttcgtga caccaatgaa gatgaaatct   2460
atgctttctt tggtattctg gtaatgacag cagtgagaaa agataaccac atgtccacag   2520
atgacctctt tggatcgatc tttgtcaatg tgtacgtctc tgtaatgagt ctgtggatcg   2580
ttttggattt tttgatacga tgtcttagaa tggatgacaa aagtatacgg cccacacttc   2640
gagaaaacga tgtatttact cctgttagaa aaatatggga tctctttatc catcagtgca   2700
tacaaaatta cactccaggg gctcatttga ccatagatga acagttactt ggttttagag   2760
gacggtgtcc gtttaggatg tatatcccaa acaagccaag taagtatgga ataaaaatcc   2820
tcatgatgtg tgacagtggt acgaagtata tgataaatgg aatgccttat ttgggaagag   2880
```

```
gaacacagac caacggagta ccactcggtg aatactacgt gaaggagtta tcaaagcctg    2940
tgcacggtag ttgtcgtaat attacgtgtg acaattggtt cacctcaatc cctttggcaa    3000
aaaacttact acaagaaccg tataagttaa ccattgtggg aaccgtgcga tcaaacaaac    3060
gcgagatacc ggaagtactg aaaaacagtc gctccaggcc agtgggaaca tcgatgtttt    3120
cttttgacgg accccttact ctcgtctcat ataaaccgaa gccagctaag atggtatact    3180
tattatcatc ttgtgatgag gatgcttcta tcaacgaaag taccggtaaa ccgcaaatgg    3240
ttatgtatta taatcaaact aaaggcggag tggacacgct agaccaaatg tgttctgtga    3300
tgacctgcag taggaagacg aataggtggc ctatggcatt attgtacgga atgataaaca    3360
ttgcctgcat aaattctttt attatataca gccataatgt cagtagcaag ggagaaaagg    3420
ttcaaagtct caaaaaattt atgagaaacc tttacatgag cctgacgtca tcgtttatgc    3480
gtaaccgttt agaagctcct actttgaaga gatatttgcg cgataatatc tctaatattt    3540
tgccaaatga agtgcctggt acatcagatg acagtactga agagccagta atgaaaaaac    3600
gtacttactg tacttactgc ccctctaaaa taaggcgaaa ggcaaatgca tcgtgcaaaa    3660
aatgcaaaaa agttatttgt cgagagcata atattgatat gtgccaaagt tgtttctgga    3720
ctgactaata agtataattt gtttctatta tgtataagtt aagctaatta cttattttat    3780
aatacaacat gactgttttt aaagtacaaa ataagtttat ttttgtaaaa gagagaatgt    3840
ttaaaagttt tgttacttta gaagaaattt tgagttttt g tttttttt t a ataaataaat    3900 aaacataaat aaattgtttg ttgaatttat tattagtatg taagtgtaaa tataataaaa    3960
cttaatatct attcaaatta ataaataaac ctcgatatac agaccgataa aaacacatgc    4020
gtcaatttta cgcatgatta tctttaacgt acgtcacaat atgattatct ttctagggtt    4080
aaataatagt ttctaatttt tttattattc agcctgctgt cgtgaatacc gtatatctca    4140
acgctgtctg tgagattgtc gtattctagc ctttttagtt tttcgctcat cgacttgata    4200
ttgtccgaca cattttcgtc gatttgcgtt ttgatcaaag acttgagcag agacacgtta    4260
atcaactgtt caaattgatc catattaacg atatcaaccc gatgcgtata tggtgcgtaa    4320
aatatatttt ttaaccctct tatactttgc actctgcgtt aatacgcgtt cgtgtacaga    4380
cgtaatcatg ttttctttt t tggataaaac tcctactgag tttgacctca tattagaccc    4440
tcacaagttg caaaacgtgg catttttta c caatgaagaa tttaaagtta ttttaaaaaa    4500
tttcatcaca gatttaaaga agaaccaaaa attaaattat ttaatcgacc agttaatcaa    4560
cgtgtacaca gagcgcaaaa aacacgcagc ccgacgtgtt ggctaaaatt attaaatcaa    4620
cttgtgttat agtcacgatt tgccgtccaa cgtgttcctc aaaaagttga agaccaacaa    4680
gtttacggac actagttaat tatttgattt tgccccactt cattttgtgg gatcacaatt    4740
ttgttatatt ttaaacaaag cttggcactg gccgtcgttt tacaacgtcg tgactgggaa    4800
aaccctggcg ttacccaact taatcgcctt gcagcacatc cccctttcgc cagctggcgt    4860
aatagcgaag aggcccgcac cgatcgccct tcccaacagt tgcgcagcct gaatggcgaa    4920
tggcgcctga tgcggtattt tctccttacg catctgtgcg gtatttcaca ccgcatatgg    4980
tgcactctca gtacaatctg ctctgatgcc gcatagttaa gccagccccg acacccgcca    5040
acacccgctg acgcgccctg acgggcttgt ctgctcccgg catccgctta cagacaagct    5100
gtgaccgtct ccgggagctg catgtgtcag aggttttcac cgtcatcacc gaaacgcgcg    5160
agacgaaagg gcctcgtgat acgcctattt ttataggtta atgtcatgat aataatggtt    5220
```

```
tcttagacgt caggtggcac ttttcgggga aatgtgcgcg gaaccccaat ttgtttattt   5280
ttctaaatac attcaaatat gtatccgctc atgagacaat aaccctgata atgcttcaa   5340
taatattgaa aaaggaagag tatgagtatt caacatttcc gtgtcgccct tattcccttt   5400
tttgcggcat tttgccttcc tgttttgct cacccagaaa cgctggtgaa agtaaaagat   5460
gctgaagatc agttgggtgc acgagtgggt tacatcgaac tggatctcaa cagcggtaag   5520
atccttgaga gttttcgccc cgaagaacgt tttccaatga tgagcacttt taaagttctg   5580
ctatgtggcg cggtattatc ccgtattgac gccgggcaag agcaactcgg tcgccgcata   5640
cactattctc agaatgactt ggttgagtac tcaccagtca cagaaaagca tcttacggat   5700
ggcatgacag taagagaatt atgcagtgct gccataacca tgagtgataa cactgcggcc   5760
aacttacttc tgacaacgat cggaggaccg aaggagctaa ccgcttttt gcacaacatg   5820
ggggatcatg taactcgcct tgatcgttgg gaaccggcgc tgaatgaagc cataccaaac   5880
gacgagcgtg acaccacgat gcctgtagca atggcaacaa cgttgcgcaa actattaact   5940
ggcgaactac ttactctagc ttcccggcaa caattaatag actggatgga gcggataaa   6000
gttgcaggac cacttctgcg ctcggccctt ccggctggct ggtttattgc tgataaatct   6060
ggagccggtg agcgtgggtc tcgcggtatc attgcagcac tggggccaga tggtaagccc   6120
tcccgtatcg tagttatcta cacgacgggg agtcaggcaa ctatggatga acgaaataga   6180
cagatcgctg agataggtgc ctcactgatt aagcattggt aactgtcaga ccaagtttac   6240
tcatatatac tttagattga tttaaaactt cattttaat ttaaaaggat ctaggtgaag   6300
atcctttttg ataatctcat gaccaaaatc ccttaacgtg agttttcgtt ccactgagcg   6360
tcagaccccg tagaaaagat caaaggatct tcttgagatc ctttttttct gcgcgtaatc   6420
tgctgcttgc aaacaaaaaa accaccgcta ccagcggtgg tttgtttgcc ggatcaagag   6480
ctaccaactc tttttccgaa ggtaactggc ttcagcagag cgcagatacc aaatactgtc   6540
cttctagtgt agccgtagtt aggccaccac ttcaagaact ctgtagcacc gcctacatac   6600
ctcgctctgc taatcctgtt accagtggct gctgccagtg gcgataagtc gtgtcttacc   6660
gggttggact caagacgata gttaccggat aaggcgcagc ggtcgggctg aacggggggt   6720
tcgtgcacac agcccagctt ggagcgaacg acctacaccg aactgagata cctacagcgt   6780
gagcattgag aaagcgccac gcttcccgaa gggagaaagg cggacaggta tccggtaagc   6840
ggcagggtcg gaacaggaga gcgcacgagg gagcttccag ggggaaacgc ctggtatctt   6900
tatagtcctg tcgggtttcg ccacctctga cttgagcgtc gatttttgtg atgctcgtca   6960
ggggggcgga gcctatggaa aaacgccagc aacgcggcct ttttacggtt cctggccttt   7020
tgctggcctt ttgctcacat gttctttcct gcgttatccc ctgattctgt ggataaccgt   7080
attaccgcct ttgagtgagc tgataccgct cgccgcagcc gaacgaccga gcgcagcgag   7140
tcagtgagcg aggaagcgga agagcgccca atacgcaaac cgcctctccc cgcgcgttgg   7200
ccgattcatt aatgcagctg gcacgacagg tttcccgact ggaaagcggg cagtgagcgc   7260
aacgcaatta atgtgagtta gctcactcat taggcacccc aggctttaca ctttatgctt   7320
ccggctcgta tgttgtgtgg aattgtgagc ggataacaat ttcacacagg aaacagctat   7380
gaccatgatt acgaattcga gctcggtacc cggggatcct ctagagtcga cgctcgcgcg   7440
acttggtttg ccattcttta gcgcgcgtcg cgtcacacag cttggccaca atgtggtttt   7500
tgtcaaacga agattctatg acgtgtttaa agtttaggtc gagtaaagcg caaatctttt   7560
```

```
<210> SEQ ID NO 21
<211> LENGTH: 38
<212> TYPE: DNA
<213> ORGANISM: Artificial Sequence
<220> FEATURE:
<223> OTHER INFORMATION: Description of Artificial
      Sequence:BamHI/XbaI-TTAA-XbaI/BamHI nucleotide
      sequence

<400> SEQUENCE: 21
cctaggagat ctaattgggc ccaattgagt ctcctagg                              38

<210> SEQ ID NO 22
<211> LENGTH: 38
<212> TYPE: DNA
<213> ORGANISM: Artificial Sequence
<220> FEATURE:
<223> OTHER INFORMATION: Description of Artificial
      Sequence:BamHI/XbaI-TTAA-XbaI/BamHI nucleotide
      sequence

<400> SEQUENCE: 22
ggatcctcta gattaacccg ggttaactca gaggatcc                              38
```